United States Patent
Thalladi et al.

(10) Patent No.: US 9,271,965 B2
(45) Date of Patent: Mar. 1, 2016

(54) CRYSTALLINE FORMS OF (R)-3-[N-(3'-CHLOROBIPHENYL-4-YLMETHYL)-N'-(3-HYDROXYISOXAZOLE-5-CARBONYL)HYDRAZINO]-2-HYDROXYPROPRIONIC ACID ISOPROPYL ESTER

(71) Applicants: Venkat R. Thalladi, Foster City, CA (US); Jerry Nzerem, South San Francisco, CA (US); Miroslav Rapta, San Carlos, CA (US)

(72) Inventors: Venkat R. Thalladi, Foster City, CA (US); Jerry Nzerem, South San Francisco, CA (US); Miroslav Rapta, San Carlos, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 360 days.

(21) Appl. No.: 13/851,273

(22) Filed: Mar. 27, 2013

(65) Prior Publication Data

US 2013/0259897 A1    Oct. 3, 2013

Related U.S. Application Data

(60) Provisional application No. 61/616,785, filed on Mar. 28, 2012.

(51) Int. Cl.

| | | |
|---|---|---|
| C07D 231/14 | (2006.01) |
| C07D 401/06 | (2006.01) |
| C07D 261/18 | (2006.01) |
| C07D 249/10 | (2006.01) |
| C07D 471/04 | (2006.01) |
| C07D 257/04 | (2006.01) |
| C07D 263/34 | (2006.01) |
| A61K 31/42 | (2006.01) |
| A61K 45/06 | (2006.01) |
| C07C 215/10 | (2006.01) |
| C07C 213/08 | (2006.01) |
| C07C 229/26 | (2006.01) |
| C07C 227/16 | (2006.01) |

(52) U.S. Cl.
CPC .............. *A61K 31/42* (2013.01); *A61K 45/06* (2013.01); *C07C 213/08* (2013.01); *C07C 215/10* (2013.01); *C07C 227/16* (2013.01); *C07C 229/26* (2013.01); *C07D 261/18* (2013.01)

(58) Field of Classification Search
None
See application file for complete search history.

(56) References Cited

U.S. PATENT DOCUMENTS

2012/0157386 A1    6/2012   Smith et al.

FOREIGN PATENT DOCUMENTS

WO    2010/136474 A2    12/2010

OTHER PUBLICATIONS

Copy of PCT International Search Report for PCT/US2013/034005 dated Jun. 19, 2013.

*Primary Examiner* — Jeffrey S Lundgren
*Assistant Examiner* — Michael Schmitt
(74) *Attorney, Agent, or Firm* — Jeffrey A. Hagenah

(57) ABSTRACT

The invention provides crystalline forms of (R)-3-[N-(3'-chlorobiphenyl-4-ylmethyl)-N'-(3-hydroxyisoxazole-5-carbonyl)hydrazino]-2-hydroxypropionic acid isopropyl ester. This invention also provides pharmaceutical compositions comprising the crystalline compound, processes and intermediates for preparing the crystalline compound, and methods of using the crystalline compound to treat diseases.

46 Claims, 26 Drawing Sheets

CRYSTALLINE FORMS OF (R)-3-[N-(3'-CHLOROBIPHENYL-4-YLMETHYL)-N'-(3-HYDROXYISOXAZOLE-5-CARBONYL)HYDRAZINO]-2-HYDROXYPROPRIONIC ACID ISOPROPYL ESTER

CROSS-REFERENCE TO RELATED APPLICATIONS

This application claims the benefit of U.S. Provisional Application No. 61/616,785, filed on Mar. 28, 2012; the entire disclosure of which is incorporated herein by reference.

BACKGROUND OF THE INVENTION

1. Field of the Invention

The present invention relates to novel crystalline forms of (R)-3-[N-(3'-chlorobiphenyl-4-ylmethyl)-N'-(3-hydroxyisoxazole-5-carbonyl)hydrazino]-2-hydroxypropionic acid isopropyl ester, which are metabolized in vivo to a compound having activity as a neprilysin inhibitor. The invention also relates to pharmaceutical compositions comprising such compound, processes and intermediates for preparing such compound and methods of using the compound to treat diseases such as hypertension, heart failure, pulmonary hypertension, and renal disease.

2. State of the Art

Commonly-assigned U.S. Patent Publication No. 2012/0157386 to Smith et al., filed on Dec. 14, 2011, discloses novel compounds that have activity as neprilysin inhibitors, the disclosure of which is incorporated herein by reference. In particular, the compound, (R)-3-[N-(3'-chlorobiphenyl-4-ylmethyl)-N'-(3-hydroxyisoxazole-5-carbonyl)hydrazino]-2-hydroxypropionic acid isopropyl ester is specifically disclosed in this application.

The chemical structure of (R)-3-[N-(3'-chlorobiphenyl-4-ylmethyl)-N'-(3-hydroxyisoxazole-5-carbonyl)hydrazino]-2-hydroxypropionic acid isopropyl ester is represented by formula I:

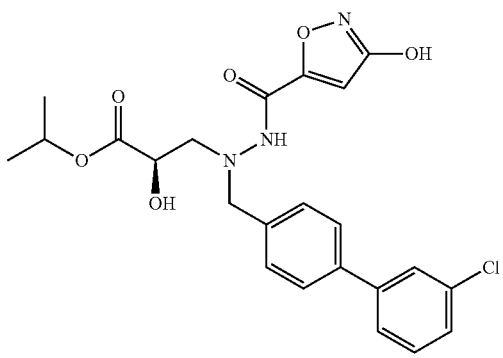

(I)

When preparing compounds for long term storage and when preparing pharmaceutical compositions and formulations, it is often desirable to have a crystalline form of the therapeutic agent that is neither hygroscopic nor deliquescent. It is also advantageous to have a crystalline form that has a relatively high melting point (i.e., greater than about 100° C.), which allows the material to be processed, for example, micronized, without significant decomposition. Accordingly, a need exists for a stable, non-deliquescent form of (R)-3-[N-(3'-chlorobiphenyl-4-ylmethyl)-N'-(3-hydroxyisoxazole-5-carbonyl)hydrazino]-2-hydroxypropionic acid isopropyl ester, which has an acceptable level of hygroscopicity and a relatively high melting point.

SUMMARY OF THE INVENTION

One aspect of the invention relates to crystalline forms of (R)-3-[N-(3'-chlorobiphenyl-4-ylmethyl)-N'-(3-hydroxyisoxazole-5-carbonyl)hydrazino]-2-hydroxypropionic acid isopropyl ester. These crystalline forms are:

a neutral monohydrate Form 1 that is characterized by a powder x-ray diffraction pattern comprising diffraction peaks at 2θ values of 8.26±0.20, 14.68±0.20, 15.64±0.20, 16.36±0.20, 18.52±0.20, 20.40±0.20, 21.08±0.20, 21.48±0.20, 21.68±0.20, 23.18±0.20, 24.50±0.20, 24.80±0.20, 25.34±0.20, and 26.56±0.20;

a neutral Form 2 that is characterized by a powder x-ray diffraction pattern comprising diffraction peaks at 2θ values of 7.48±0.20, 8.02±0.20, 9.38±0.20, 12.24±0.20, 14.86±0.20, 18.72±0.20, 20.94±0.20, 21.34±0.20, 22.32±0.20, and 24.68±0.20;

a neutral solvated Form 2' that is characterized by a powder x-ray diffraction pattern comprising diffraction peaks at 2θ values of 7.26±0.20, 8.05±0.20, 12.20±0.20, 14.48±0.20, 15.84±0.20, 16.22±0.20, 18.78±0.20, 20.60±0.20, 21.29±0.20, 21.74±0.20, 23.10±0.20, 24.16±0.20, and 24.44±0.20;

a neutral anhydrous Form 3 that is characterized by a powder x-ray diffraction pattern comprising diffraction peaks at 2θ values of 8.12±0.20, 8.86±0.20, 11.92±0.20, 13.68±0.20, 16.10±0.20, 18.12±0.20, 18.46±0.20, 19.06±0.20, 19.48±0.20, 20.60±0.20, 21.28±0.20, 24.46±0.20, 25.94±0.20, and 26.40±0.20;

a neutral anhydrous Form 4 that is characterized by a powder x-ray diffraction pattern comprising diffraction peaks at 2θ values of 8.70±0.20, 13.00±0.20, 16.00±0.20, 16.94±0.20, 17.36±0.20, 18.72±0.20, 19.00±0.20, 19.78±0.20, 20.24±0.20, 21.70±0.20, 23.68±0.20, and 27.94±0.20;

a tromethamine salt that is characterized by a powder x-ray diffraction pattern comprising diffraction peaks at 2θ values of 6.94±0.20, 9.00±0.20, 12.36±0.20, 13.74±0.20, 16.58±0.20, 17.12±0.20, 18.32±0.20, 19.86±0.20, 20.28±0.20, 21.36±0.20, 23.82±0.20, and 27.00±0.20;

an L-lysine salt that is characterized by a powder x-ray diffraction pattern comprising diffraction peaks at 2θ values of 3.10±0.20, 9.13±0.20, 10.12±0.20, 12.14±0.20, 18.33±0.20, 18.54±0.20, 20.14±0.20, 20.88±0.20, 21.72±0.20, 23.12±0.20, and 24.58±0.20; and a meglumine salt that is characterized by a powder x-ray diffraction pattern comprising diffraction peaks at 2θ values of 6.10±0.20, 8.72±0.20, 10.20±0.20, 12.24±0.20, 15.32±0.20, 17.04±0.20, 18.46±0.20, 19.40±0.20, 20.46±0.20, 21.12±0.20, 23.12±0.20, and 25.96±0.20.

Other aspects of the invention relate to processes for preparing these crystalline forms and pharmaceutical compositions comprising a pharmaceutically acceptable carrier and one of these crystalline forms. Another aspect of the invention relates to a process for purifying (R)-3-[N-(3'-chlorobiphenyl-4-ylmethyl)-N'-(3-hydroxyisoxazole-5-carbonyl)hydrazino]-2-hydroxypropionic acid isopropyl ester comprising forming one of these crystalline forms.

(R)-3-[N-(3'-chlorobiphenyl-4-ylmethyl)-N'-(3-hydroxyisoxazole-5-carbonyl)hydrazino]-2-hydroxypropionic acid isopropyl ester is a prodrug of (R)-3-[N-(3'-chlorobiphenyl-4-ylmethyl)-N'-(3-hydroxyisoxazole-5-carbonyl)hydrazino]-2-hydroxypropionic acid, which possesses neprilysin (NEP) enzyme inhibition activity. Therefore, crystalline forms of this prodrug are expected to be useful as a therapeutic agent for treating patients suffering from a disease or disorder that is treated by inhibiting the NEP enzyme or by increasing the levels of its peptide substrates, for example, hypertension, heart failure, and renal disease.

Yet another aspect of the invention relates to the use of the crystalline compounds of the invention for the manufacture of a medicament, especially for the manufacture of a medicament useful for treating hypertension, heart failure, or renal disease. Other aspects and embodiments of the invention are disclosed herein.

BRIEF DESCRIPTION OF THE DRAWINGS

Various aspects of the present invention are illustrated by reference to the accompanying drawings for the various crystalline forms of (R)-3-[N-(3'-chlorobiphenyl-4-ylmethyl)-N'-(3-hydroxyisoxazole-5-carbonyl)hydrazino]-2-hydroxypropionic acid isopropyl ester.

In FIG. 18, the peak at ~32.5° in 2θ is an artifact arising from the sample holder.

DETAILED DESCRIPTION OF THE INVENTION

Figure 1:
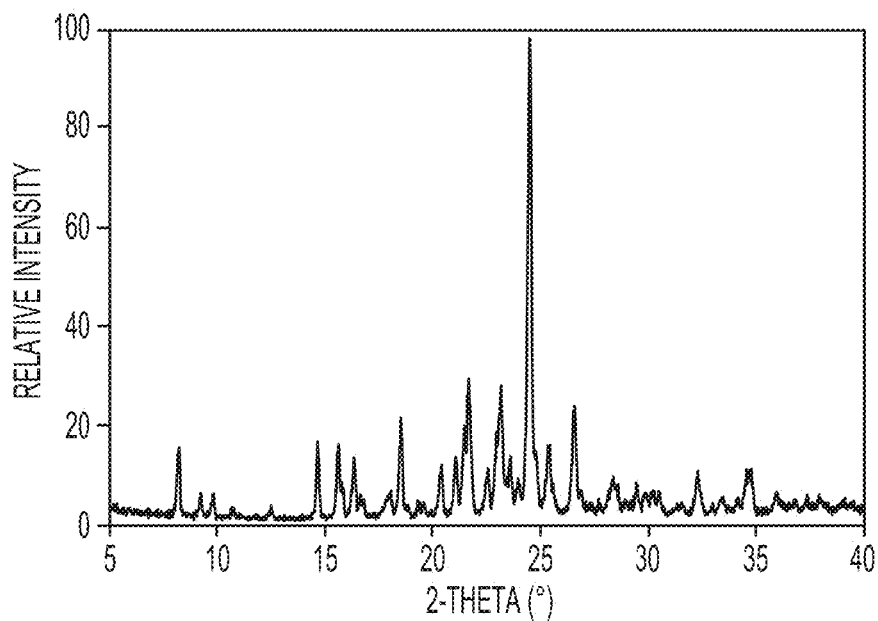
FIG. 1 shows a powder x-ray diffraction (PXRD) pattern of the crystalline neutral monohydrate Form 1.

This invention provides crystalline forms of (R)-3-[N-(3'-chlorobiphenyl-4-ylmethyl)-N'-(3-hydroxyisoxazole-5-carbonyl)hydrazino]-2-hydroxypropionic acid isopropyl ester.

This compound contains two chiral centers and has the (R) configuration. However, it will be understood by those skilled in the art that minor amounts of the (S) stereoisomer, for example, may be present in the compositions of the invention unless otherwise indicated, provided that the utility of the composition as a whole is not eliminated by the presence of such stereoisomer.

The compound of formula I is a prodrug of (R)-3-[N-(3'-chlorobiphenyl-4-ylmethyl)-N'-(3-hydroxyisoxazole-5-carbonyl)hydrazino]-2-hydroxypropionic acid, which has activity as a neprilysin inhibitor. Crystalline forms of the compound of formula I are expected to have the same activity in vivo and thus the same utility in treating diseases such as hypertension, heart failure, and renal disease. Therefore, among other uses, the crystalline forms of the invention are useful for preparing pharmaceutical compositions for treating such diseases.

DEFINITIONS

When describing the compounds, compositions, methods and processes of the invention, the following terms have the following meanings unless otherwise indicated. Additionally, as used herein, the singular forms "a," "an," and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

As used herein, the phrase "having the formula" or "having the structure" is not intended to be limiting and is used in the same way that the term "comprising" is commonly used. For example, if one structure is depicted, it is understood that all stereoisomer and tautomer forms are encompassed, unless stated otherwise.

The term "mono" as used herein is intended to mean that the crystalline form typically contains about 1.0 molar equivalents of compound (the compound of formula I) per about 1.0±0.15 molar equivalent of counterion or solvent; and in one embodiment, about 1.0 molar equivalents of compound per about 1.0 molar equivalent of counterion or solvent. For example, the crystalline neutral monohydrate Form 1 generally contains about 1.0 molar equivalents of compound per about 1.0±0.15 molar equivalent of water; and in one embodiment, about 1.0 molar equivalents of compound per about 1.0 molar equivalent water.

The term "melting point" or "melting endotherm" as used herein means the temperature at which the maximum endothermic heat flow is observed by differential scanning calorimetry, for the thermal transition that corresponds to the solid-to-liquid phase change.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug administration.

As used herein, the term "prodrug" is intended to mean an inactive (or significantly less active) precursor of a drug that is converted into its active form in the body under physiological conditions, for example, by normal metabolic processes. Such compounds may not necessarily possess pharmacological activity at NEP, but may be administered orally or parenterally and thereafter metabolized in the body to form a compound that is pharmacologically active at NEP.

The term "therapeutically effective amount" means an amount sufficient to effect treatment when administered to a patient in need thereof, that is, the amount of drug needed to obtain the desired therapeutic effect. For example, a therapeutically effective amount for treating hypertension is an amount of compound needed to, for example, reduce, suppress, eliminate, or prevent the symptoms of hypertension, or to treat the underlying cause of hypertension. In one embodiment, a therapeutically effective amount is that amount of drug needed to reduce blood pressure or the amount of drug needed to maintain normal blood pressure. On the other hand, the term "effective amount" means an amount sufficient to obtain a desired result, which may not necessarily be a therapeutic result. For example, when studying a system comprising a NEP enzyme, an "effective amount" may be the amount needed to inhibit the enzyme.

The term "treating" or "treatment" as used herein means the treating or treatment of a disease or medical condition (such as hypertension) in a patient, such as a mammal (particularly a human) that includes one or more of the following: (a) preventing the disease or medical condition from occurring, i.e., preventing the reoccurrence of the disease or medical condition or prophylactic treatment of a patient that is pre-disposed to the disease or medical condition; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient. For example, the term "treating hypertension" would include preventing hypertension from occurring, ameliorating hypertension, suppressing hypertension, and alleviating the symptoms of hypertension (for example, lowering blood pressure). The term "patient" is intended to include those mammals, such as humans, that are in need of treatment or disease prevention or that are presently being treated for disease prevention or treatment of a specific disease or medical condition, as well as test subjects in which the crystalline compound is being evaluated or being used in an assay, for example an animal model.

All other terms used herein are intended to have their ordinary meaning as understood by those of ordinary skill in the art to which they pertain.

General Synthetic Procedures

The crystalline compounds of the invention can be synthesized from readily available starting materials as described below and in the Examples. It will be appreciated that where typical or preferred process conditions (i.e., reaction temperatures, times, mole ratios of reactants, solvents, pressures, etc.) are given, other process conditions can also be used unless otherwise stated. It will be appreciated that while specific process conditions (i.e., crystallization temperatures, times, mole ratios of reactants, solvents, pressures, etc.) are given, other process conditions can also be used unless otherwise stated. In some instances, reactions or crystallizations were conducted at room temperature and no actual temperature measurement was taken. It is understood that room temperature can be taken to mean a temperature within the range commonly associated with the ambient temperature in a laboratory environment, and will typically be in the range of about 15° C. to about 30° C. In other instances, reactions or crystallizations were conducted at room temperature and the temperature was actually measured and recorded.

Generally, the crystallization is conducted in a suitable inert diluent, examples of which include, but are not limited to, acetone, acetonitrile, ethyl acetate, methyl ethyl ketone, methanol, ethanol, isopropanol, isobutanol, dichloromethane, methyl t-butyl ether, cyclopentyl methyl ether, hexanes, and the like, and mixtures thereof, optionally containing water. Mixtures of inert diluents (also referred to as solvent systems) include acetone with water, acetonitrile with water, ethanol and ethyl acetate, ethyl acetate and hexanes, and lower alcohols ($C_{1-6}$alkyl-OH) with water, for example, methanol and water and isopropanol and water. Particularly suitable solvent systems include ethyl acetate/hexanes and lower alcohol/water. Upon completion of the crystallization, the crystalline compound can be isolated from the reaction mixture by any conventional means such as precipitation, filtration, concentration, centrifugation, dried in vacuo, and the like.

The (R)-3-[N-(3'-chlorobiphenyl-4-ylmethyl)-N'-(3-hydroxyisoxazole-5-carbonyl)-hydrazino]-2-hydroxypropionic acid isopropyl ester starting materials can be prepared by techniques that are well known in the art, and specific examples are provided herein.

The molar ratios described in the methods of the invention can be readily determined by various methods available to those skilled in the art. For example, such molar ratios can be readily determined by $^1$H NMR. Alternatively, elemental analysis and HPLC methods can be used to determine the molar ratio.

Crystalline Neutral Monohydrate Form 1

In one embodiment, the crystalline neutral monohydrate Form 1 can be prepared by (a) treating amorphous (R)-3-[N-(3'-chlorobiphenyl-4-ylmethyl)-N'-(3-hydroxyisoxazole-5-carbonyl)hydrazino]-2-hydroxypropionic acid isopropyl ester with methanol and water or acetonitrile and water; (b) heating then cooling the resulting slurry; (c) optionally stirring or sonicating to complete dissolution; and allowing solids to form and isolating the solids to yield the crystalline neutral monohydrate Form 1. In one embodiment step (a) is conducted by first treating the ester with methanol, and subsequently adding water as an anti-solvent to form a slurry. In another embodiment, step (a) is conducted by first treating the ester with acetonitrile, and subsequently immersing the reaction vessel in water, generally warm water. Step (b) generally involves heating the slurry to a temperature within the range of about 55-75° C., and in one embodiment to about 70° C. The cooling in step (b) is generally to about room temperature.

Figure 15:
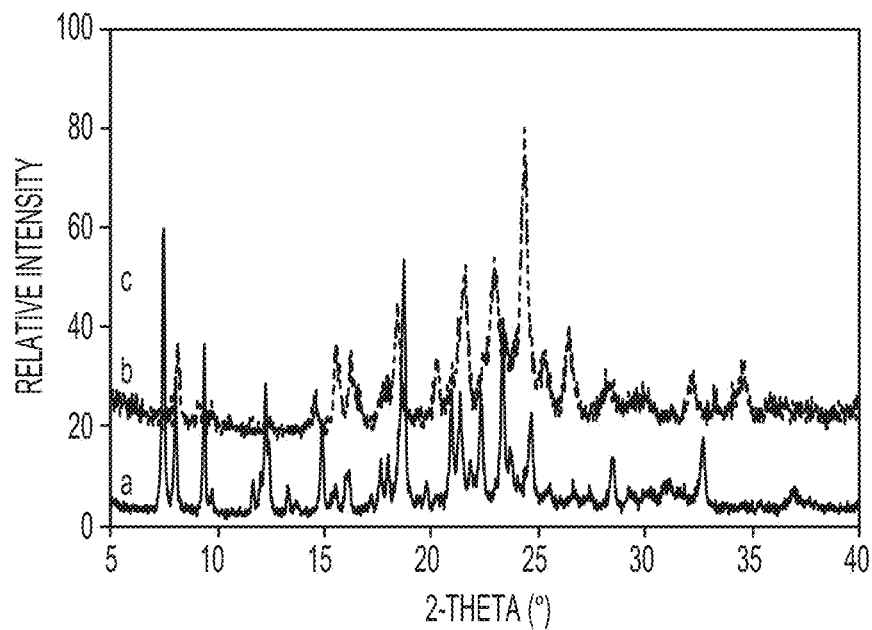
FIG. 15 and FIG. 16 show the PXRD patterns for Form 2 that has been exposed to 84% relative humidity (FIG. 15-b) and reslurried in water (FIG. 16-b); for comparison purposes the PXRD patterns for Form 2 (FIG. 15-a and FIG. 16-a) and Form 1 (FIG. 15-c and FIG. 16-c) are included.

The total quantity of water (3.5-3.6%) taken up by Form 2 in the DMS experiment was close to the expected water content (3.66%) in a monohydrate, which suggested that Form 2 might convert to Form 1 at high relative humidities. In one experiment, a sample of Form 2 was exposed to 84% RH for seven days. Analysis of this moisture-exposed sample by PXRD (FIG. 15-b) showed that Form 2 converts to Form 1 at high humidities. This experiment established that Form 2 is metastable to the monohydrate Form 1 in high relative humidities (>75% RH). Accordingly, in another embodiment, the crystalline neutral monohydrate Form 1 can be prepared by (a') exposing the crystalline neutral Form 2 to high humidity; and in one embodiment exposing Form 2 to about >75% relative humidity, typically for about 5-7 days.

Figure 16:
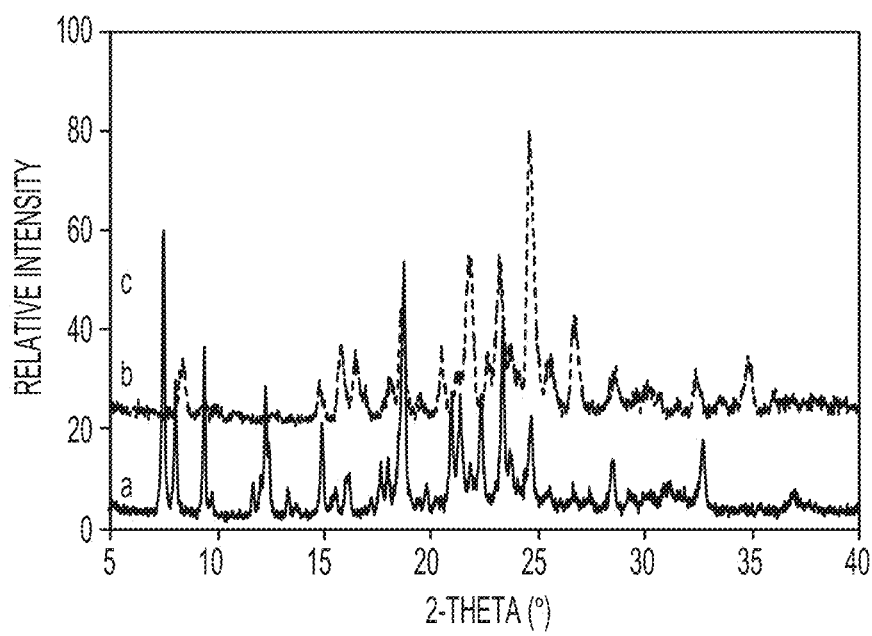

In one experiment, a sample of Form 2 was slurried in water (e.g., deionized water) for five days, and the resultant solid showed a PXRD pattern consistent with Form 1 (FIG. 16-b). This experiment established that Form 2 is metastable to the monohydrate Form 1 in solutions containing water. Thus, in yet another embodiment, the crystalline neutral monohydrate Form 1 can be prepared by (a") reslurrying the crystalline neutral Form 2 in water or an aqueous solution; (b") heating then cooling the resulting slurry; (c") optionally stirring or sonicating to complete dissolution; and allowing solids to form and isolating the solids to yield the crystalline neutral monohydrate Form 1. Step (a") is typically conducted by first treating the ester with methanol, and subsequently adding water as an anti-solvent to form a slurry. Step (a") is typically conducted by first treating Form 2 with methanol, and subsequently adding water as an anti-solvent to form a slurry. Step (b") generally involves heating the slurry to a temperature within the range of about 55-75° C., and in one embodiment to about 60° C. The cooling in step (b") is generally to about room temperature.

Crystalline Neutral Form 2

In one embodiment, the crystalline neutral Form 2 can be prepared by solution crystallization. Generally, this involves (a) treating amorphous (R)-3-[N-(3'-chlorobiphenyl-4-ylmethyl)-N'-(3-hydroxyisoxazole-5-carbonyl)hydrazino]-2-hydroxypropionic acid isopropyl ester with methylene chloride and an aqueous $NH_4Cl$ solution; (b) optionally stirring or sonicating to complete dissolution; and allowing solids to form and isolating the solids to yield the crystalline neutral Form 2.

In another embodiment, the crystalline neutral Form 2 can be prepared by (a') reacting (R)-3-{N-(3'-chlorobiphenyl-4-ylmethyl)-N'-[3-(4-methoxybenzyloxy)isoxazole-5-carbonyl]hydrazino}-2-hydroxypropionic acid isopropyl ester with anisole and trifluoroacetic acid in a suitable solvent; (b') optionally stirring or sonicating to complete dissolution; ('c) adding an inert diluent and seed crystals of Form 2; and allowing solids to form and isolating the solids to yield the crystalline neutral Form 2. The solvent in step (a') can be dichloromethane. The inert diluent in step (c') can be diisopropyl ether. This process is generally conducted at about room temperature.

Crystalline Neutral Solvated Form 2'

When samples of amorphous (R)-3-[N-(3'-chlorobiphenyl-4-ylmethyl)-N'-(3-hydroxyisoxazole-5-carbonyl)hydrazino]-2-hydroxypropionic acid isopropyl ester were slurried in a solution of ethyl acetate and hexanes or in ethyl acetate alone, solids were produced that showed a PXRD pattern and DSC profile similar to the PXRD pattern and DSC profile of Form 2. However, the TGA profile showed much larger weight loss compared to Form 2. This solid is an isostructural solvate of Form 2 and is referred to as Form-2', because it has a PXRD pattern similar to Form 2 but contains a greater amount of lattice solvent.

Thus, in one embodiment, the crystalline neutral solvated Form 2' can be prepared by (a) treating amorphous (R)-3-[N-(3'-chlorobiphenyl-4-ylmethyl)-N'-(3-hydroxyisoxazole-5-carbonyl)hydrazino]-2-hydroxypropionic acid isopropyl ester with an inert diluent; (b) heating then cooling the resulting slurry; (c) optionally stirring or sonicating to complete dissolution; and (d) allowing solids to form and isolating the solids to yield the crystalline neutral solvated Form 2'. In one embodiment, the inert diluent is ethyl acetate, alone or in combination with hexanes. Step (b) generally involves heating the slurry to a temperature within the range of about 55-75° C., and in one embodiment to about 60° C., and in another embodiment to about 70° C. The cooling in step (b) is generally to about room temperature.

Crystalline Neutral Anhydrous Form 3

The crystalline neutral anhydrous Form 3 is formed at temperatures above 100° C. and is produced by the temperature-induced phase transition of Form 2 when it is heated and then cooled. Thus, in one embodiment, the crystalline neutral anhydrous Form 3 can be prepared by (a) heating the crystalline neutral anhydrous Form 2 to about 105-120° C.; (b) cooling to about room temperature; and (c) isolating the solids to yield the crystalline neutral anhydrous Form 3. In one embodiment, step (a) involves heating the sample to a temperature in the range of about 110-120° C., and in another embodiment, the sample is heated to temperature in the range of about 105-110° C.

Crystalline Neutral Anhydrous Form 4

The crystalline neutral anhydrous Form 4 is formed at temperatures above 100° C. and is produced by the temperature-induced phase transition of Form 1 when it is heated and then cooled. Thus, in one embodiment, the crystalline neutral anhydrous Form 4 can be prepared by (a) heating the crystalline neutral monohydrate Form 1 to about 120° C.; (b) cooling to about room temperature; and (c) isolating the solids to yield the crystalline neutral anhydrous Form 4.

Crystalline Tromethamine Salt

In one embodiment, the crystalline tromethamine salt can be prepared by (a) treating (R)-3-[N-(3'-chlorobiphenyl-4-ylmethyl)-N'-(3-hydroxyisoxazole-5-carbonyl)hydrazino]-2-hydroxypropionic acid isopropyl ester with tromethamine in an inert diluent; (b) optionally heating, stirring, and/or sonicating to complete dissolution; and (c) allowing solids to form and isolating the solids to yield the crystalline tromethamine salt.

Generally, the ester and tromethamine are each dissolved in a suitable inert diluent, and the two solutions are subsequently combined. In one embodiment, the inert diluent in each solution is ethanol. Once mixed, the solutions can be heated to facilitate dissolution, typically in the range of about 40-60°.

Crystalline L-lysine Salt

In one embodiment, the crystalline L-lysine salt can be prepared by (a) treating (R)-3-[N-(3'-chlorobiphenyl-4-ylmethyl)-N'-(3-hydroxyisoxazole-5-carbonyl)hydrazino]-2-hydroxypropionic acid isopropyl ester with L-lysine in an inert diluent; (b) optionally heating, stirring, and/or sonicating to complete dissolution; and (c) allowing solids to form and isolating the solids to yield the crystalline L-lysine salt.

Generally, the ester and L-lysine are each dissolved in a suitable inert diluent, and the two solutions are subsequently combined. In one embodiment, the inert diluent in the ester solution is ethanol and the inert diluent in the L-lysine solution is an ethanol/water mixture. Once mixed, the solutions can be heated to facilitate dissolution, typically in the range of about 40-60°.

Crystalline Meglumine Salt

In one embodiment, the crystalline meglumine salt can be prepared by (a) treating (R)-3-[N-(3'-chlorobiphenyl-4-ylmethyl)-N'-(3-hydroxyisoxazole-5-carbonyl)hydrazino]-2-hydroxypropionic acid isopropyl ester with meglumine in an inert diluent; (b) optionally heating, stirring, and/or sonicating to complete dissolution; and (c) allowing solids to form and isolating the solids to yield the crystalline meglumine salt.

Generally, the ester and meglumine are each dissolved in a suitable inert diluent, and the two solutions are subsequently combined. In one embodiment, the inert diluent is ethanol. Once mixed, the solutions can be heated to facilitate dissolution, typically in the range of about 40-60°.

In all of these processes, the final step involves allowing solids to form and after a suitable amount of time, crystals will be observed. After crystals are observed, the volume of the mother liquor can be reduced and the crystals isolated and dried. In one embodiment, the crystals are air dried under ambient conditions.

Crystalline Properties

Among other advantages, it has been discovered that forming a crystalline form of (R)-3-[N-(3'-chlorobiphenyl-4-ylmethyl)-N'-(3-hydroxyisoxazole-5-carbonyl)hydrazino]-2-hydroxypropionic acid isopropyl ester, is useful for purifying the compound itself.

As is well known in the field of powder x-ray diffraction, relative peak heights of powder x-ray diffraction (PXRD) patterns are dependent on a number of factors relating to sample preparation and instrument geometry, while peak positions are relatively insensitive to experimental details. PXRD patterns and differential scanning calorimetry (DSC) thermograms were obtained, and thermogravimetric analysis (TGA) and dynamic moisture sorption (DMS) assessment (also known as a moisture sorption-desorption profile) were performed as described herein. Thus, in one embodiment, the crystalline compounds are characterized by a PXRD pattern having certain peak positions. In another embodiment, the crystalline compounds are characterized by a DSC thermogram. In yet another embodiment, the crystalline compounds are characterized by a TGA trace. In still other embodiments, the crystalline compounds are characterized by a polarized light microscopic (PLM) analysis.

Crystalline Neutral Monohydrate Form 1

The crystalline neutral monohydrate Form 1 is characterized by a PXRD pattern in which the peak positions are substantially in accordance with those shown in FIG. 1. Peaks above 5% relative height are listed in the table below. This pattern shows three peaks in the range 7.5-10° on 2θ scale with the most intense peak appearing at ≈24.5°. These and other peaks in the diffraction patterns can be used to distinguish Form 1 from the other forms described herein. Different batches of Form 1 showed complete correspondence of diffraction profiles throughout the data collection window (2-40° on 2θ scale). The clear distinction between the diffraction peaks and the background all the way up to 35° on 2θ scale, despite the fibrous morphologies and small sizes of the crystals, indicates the long range crystalline order within the particles of Form 1.

| 2θ | d (Å) | Height[1] | H %[2] | * |
|---|---|---|---|---|
| 8.26 | 10.70 | 187 | 14.4 | * |
| 9.26 | 9.54 | 62 | 4.8 | |
| 9.82 | 9.00 | 64 | 5.0 | |
| 14.68 | 6.03 | 215 | 16.6 | * |
| 15.64 | 5.66 | 200 | 15.4 | * |
| 16.36 | 5.41 | 160 | 12.4 | * |
| 18.06 | 4.91 | 69 | 5.3 | |
| 18.52 | 4.79 | 273 | 21.1 | * |
| 20.40 | 4.35 | 139 | 10.7 | * |
| 21.08 | 4.21 | 158 | 12.2 | * |
| 21.48 | 4.13 | 244 | 18.8 | * |
| 21.68 | 4.10 | 375 | 28.9 | * |
| 22.58 | 3.94 | 98 | 7.6 | |
| 23.18 | 3.83 | 333 | 25.7 | * |
| 23.61 | 3.77 | 122 | 9.4 | |
| 24.50 | 3.63 | 1297 | 100.0 | * |
| 24.80 | 3.59 | 140 | 10.8 | * |
| 25.34 | 3.51 | 170 | 13.1 | * |
| 26.56 | 3.35 | 294 | 22.7 | * |
| 28.36 | 3.15 | 86 | 6.6 | |

-continued

| 2θ | d (Å) | Height[1] | H %[2] | * |
|---|---|---|---|---|
| 29.42 | 3.03 | 65 | 5.0 | |
| 32.28 | 2.77 | 118 | 9.1 | |
| 34.76 | 2.58 | 118 | 9.1 | |

[1]Peak height from base line
[2]Percent peak height compared to highest peak
* Indicates peaks that are important to identify this form Thus, in one embodiment, the crystalline neutral monohydrate Form 1 is characterized by PXRD pattern comprising diffraction peaks at 2θ values of 2θ values of 8.26±0.20, 14.68±0.20, 15.64±0.20, 16.36±0.20, 18.52±0.20, 20.40±0.20, 21.08±0.20, 21.48±0.20, 21.68±0.20, 23.18±0.20, 24.50±0.20, 24.80±0.20, 25.34±0.20, and 26.56±0.20; and further characterized by having one or more additional diffraction peaks at 2θ values selected from 2θ values of 9.26±0.20, 9.82±0.20, 18.06±0.20, 22.58±0.20, 23.61±0.20, 28.36±0.20, 29.42±0.20, 32.28±0.20, and 34.76±0.20.

Figure 2:
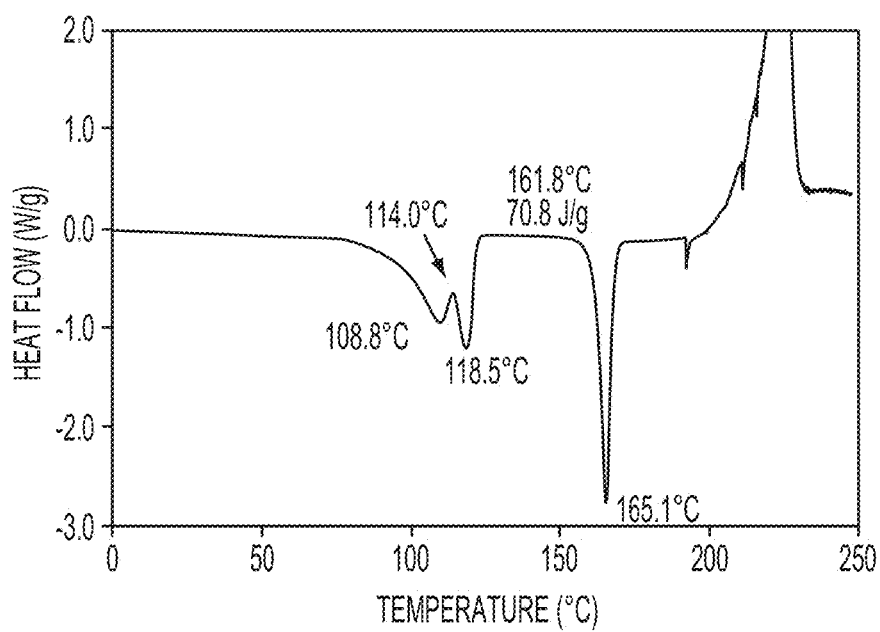
FIG. 2 shows a differential scanning calorimetry (DSC) thermogram.

In one embodiment, the crystalline neutral monohydrate Form 1 is characterized by the DSC thermogram in FIG. 2. The DSC thermogram showed an endotherm that spanned 75-125° C., which corresponds to the dehydration of lattice water. Interestingly, an exotherm overlapped (peaking at 114° C.) with the dehydration endotherm. This exotherm may correspond to a recrystallization or to another phase transition event. The interplay between these two thermal events resulted in small variations in the appearance of dehydration endotherm in different batches. Despite these two overlapping thermal events, Form 1 typically melted within the range of about 160-166° C., and in one embodiment within the range of about 162-165° C., with sharp melting endotherms in DSC. Form 1 did not lose lattice water when exposed to ambient conditions for more than a month and when placed in high vacuum for more than 24 hours. This suggests that the water in this hydrate form is strongly bound and does not easily escape the lattice. Form 1 does lose lattice water in the temperature range 100-125° C.

Figure 3:
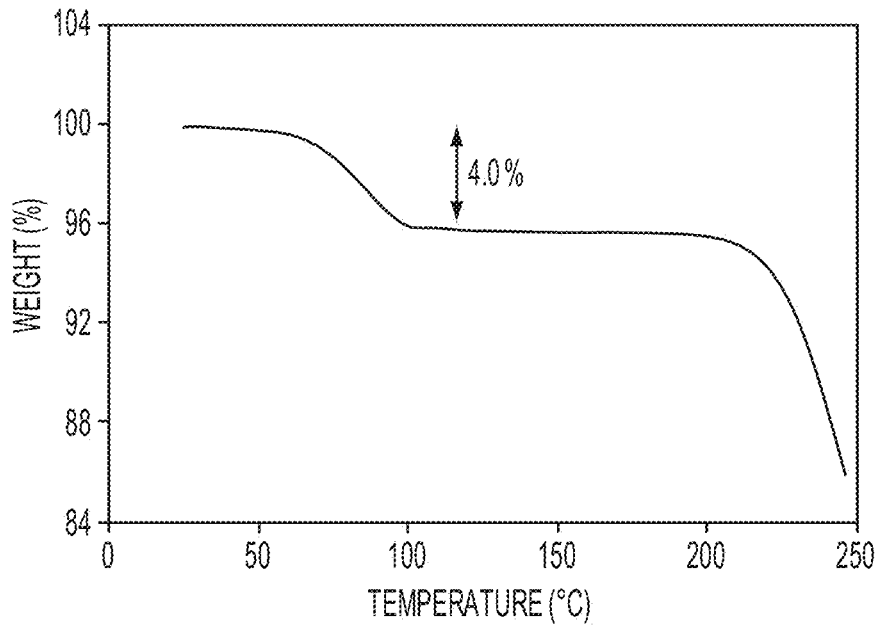
FIG. 3 shows a thermal gravimetric analysis (TGA) trace for this form.

In one embodiment, the crystalline neutral monohydrate Form 1 is characterized by the TGA profile in FIG. 3. The TGA profile showed a weight loss of about 4% in the range 60-100° C. Other batches of Form 1 showed weight losses in the range 3.5-4.3%. These differences are possibly due to incomplete drying of the sample and surface or interstitial adherence of solvents of crystallization. Karl-Fisher analysis showed that Form 1 contained 3.58% water. The expected water content in a monohydrate is 3.66%. These observations confirmed that Form 1 is a monohydrate. Both the DSC and TGA showed heat induced decomposition of Form 1 after 175° C.

Figure 4:
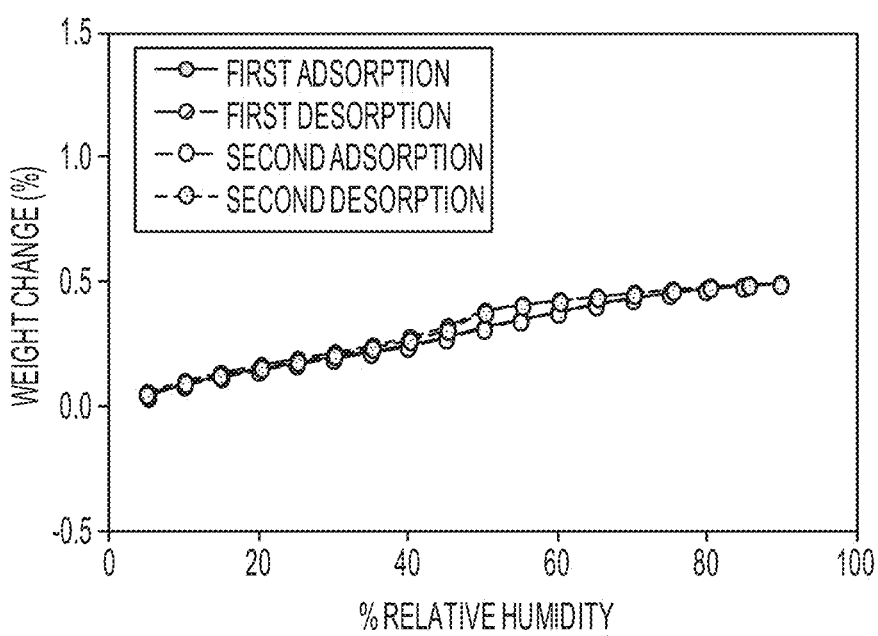
FIG. 4 shows a dynamic moisture sorption (DMS) profile.
Figure 5:
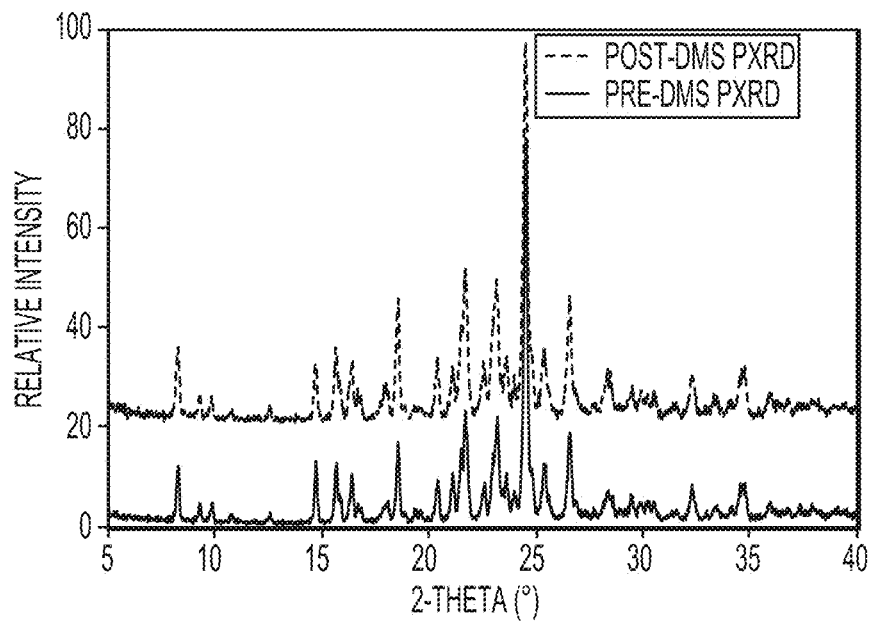
FIG. 5 shows the overlay of the PXRD patterns of the sample before and after being subjected to the moisture sorption-desorption experiment for this form.

In one embodiment, the crystalline neutral monohydrate Form 1 is characterized by the DMS profile in FIG. 4. Samples of Form 1 were subjected to isothermal moisture sorption analysis at 25° C. The amount of water adsorbed by Form 1 showed a small increase with increasing relative humidity up to 90% RH. The step-like profile at 40-60% RH may indicate capillary condensation. At 90% RH, the total moisture uptake was ~0.5%. Form 1 did not show hysteresis between two cycles of water sorption and desorption, and the initial and final mass content at 5% RH remained similar. Form 1 is slightly hygroscopic according to the classification of the European Pharmacopoeia Technical Guide. The relatively low amount of moisture sorbed and the reversibility of the adsorption-desorption process indicates that Form 1 is a desirable crystalline form. The materials obtained after the DMS analysis did not show any change in their PXRD pattern (FIG. 4), indicating that moisture sorption and desorption does not lead to any phase transition. These findings suggest that under the storage conditions (and the maximal drying or maximal moisture exposure) expected for drug substance and drug products, Form 1 can remain stable and retain its lattice structure.

Figure 6:
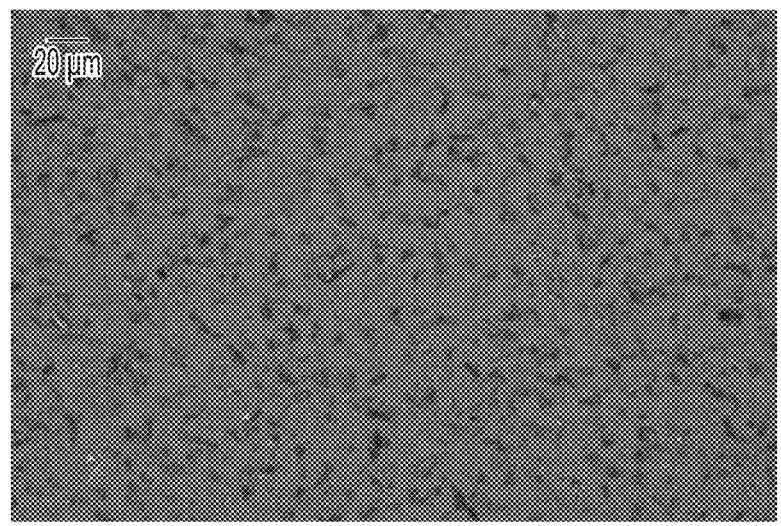
FIG. 6 and FIG. 7 are polarized light microscopic (PLM) images of this form.
Figure 7:
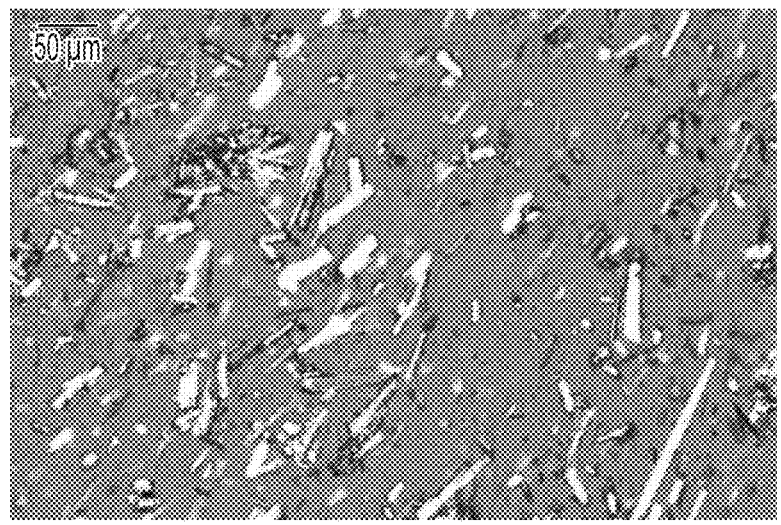

The crystalline neutral monohydrate Form 1 is a white solid with thin fibrous particles having sizes in the range of 0.5-10 μm, and under agitated conditions, can be characterized by the PLM image in FIG. 6 (using material of Example 2). When crystallized under undisturbed conditions, Form 1 can be characterized by the PLM image in FIG. 7 (using material of Example 3), which shows this crystalline compound as being birefringent (suggesting their crystallinity) with slightly larger crystals with sizes in the range 10-50 μm and with plate-like morphology.

Crystalline Neutral Form 2

Figure 8:
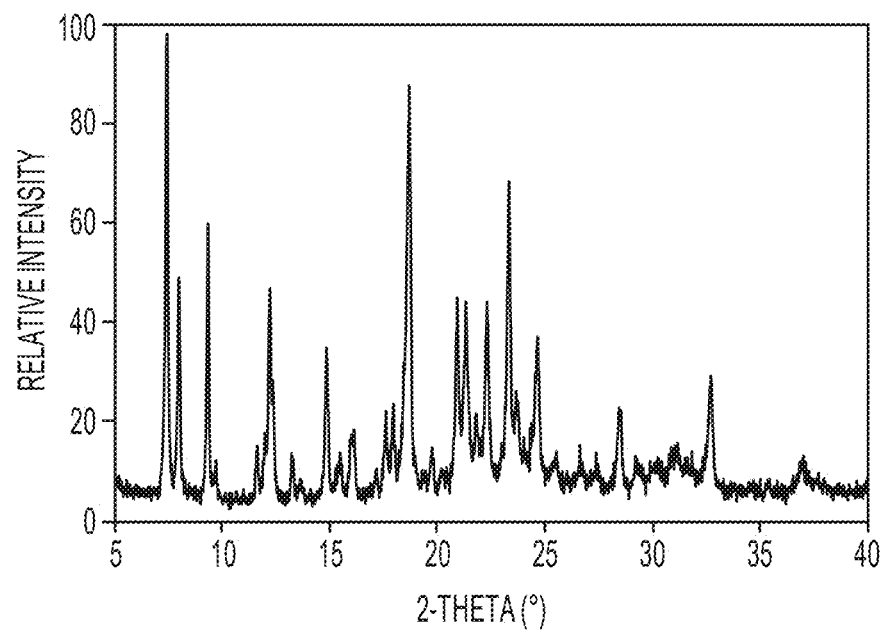
FIG. 8 shows a PXRD pattern of the crystalline neutral Form 2.

The neutral Form 2 is characterized by a PXRD pattern in which the peak positions are substantially in accordance with those shown in FIG. 8. Peaks above 8% relative height are listed in the table below. This pattern show three peaks in the range 7-10° on 2θ scale with the most intense peak appearing at ~7.5°. These and other peaks in the diffraction patterns can be used to distinguish Form 2 from the other forms described herein. Different batches of Form 2 showed complete correspondence of diffraction profiles throughout the data collection window (2-40° on 2θ scale). The clear distinction between the diffraction peaks and the background all the way up to 35° on 2θ scale, despite the thin plate-like morphologies and small sizes of the crystals, indicates the long range crystalline order within the particles of Form 2.

| 2θ | d (Å) | Height[1] | H %[2] | * |
|---|---|---|---|---|
| 7.48 | 11.82 | 717 | 100.0 | * |
| 8.02 | 11.01 | 337 | 47.0 | * |
| 9.38 | 9.42 | 426 | 59.4 | * |
| 9.74 | 9.08 | 58 | 8.1 | |
| 11.66 | 7.59 | 83 | 11.5 | |
| 12.00 | 7.37 | 103 | 14.4 | |
| 12.24 | 7.23 | 329 | 45.8 | * |
| 13.26 | 6.67 | 70 | 9.7 | |
| 14.86 | 5.96 | 229 | 31.9 | * |
| 15.50 | 5.71 | 65 | 9.1 | |
| 16.14 | 5.49 | 96 | 13.5 | |
| 17.64 | 5.03 | 108 | 15.0 | |
| 17.98 | 4.93 | 111 | 15.5 | |
| 18.72 | 4.74 | 610 | 85.1 | * |
| 19.78 | 4.49 | 60 | 8.3 | |
| 20.94 | 4.24 | 299 | 41.7 | * |
| 21.34 | 4.16 | 248 | 34.6 | * |
| 21.82 | 4.07 | 68 | 9.5 | |
| 22.32 | 3.98 | 255 | 35.5 | * |
| 23.34 | 3.81 | 442 | 61.7 | |
| 23.66 | 3.76 | 109 | 15.2 | |
| 24.68 | 3.61 | 199 | 27.7 | * |
| 26.62 | 3.35 | 62 | 8.6 | |
| 28.46 | 3.13 | 126 | 17.5 | |

[1]Peak height from base line
[2]Percent peak height compared to highest peak
* Indicates peaks that are important to identify this form Thus, in one embodiment, the crystalline neutral Form 2 is characterized by a PXRD pattern comprising diffraction peaks at 2θ values of 7.48±0.20, 8.02±0.20, 9.38±0.20, 12.24±0.20, 14.86±0.20, 18.72±0.20, 20.94±0.20, 21.34±0.20, 22.32±0.20, and 24.68±0.20; and further characterized by having one or more additional diffraction peaks at 2θ values selected from 9.74±0.20, 11.66±0.20, 12.00±0.20, 13.26±0.20, 15.50±0.20, 16.14±0.20, 17.64±0.20, 17.98±0.20, 19.78±0.20, 21.82±0.20, 23.34±0.20, 23.66±0.20, 26.62±0.20, and 28.46±0.20.

Figure 9:
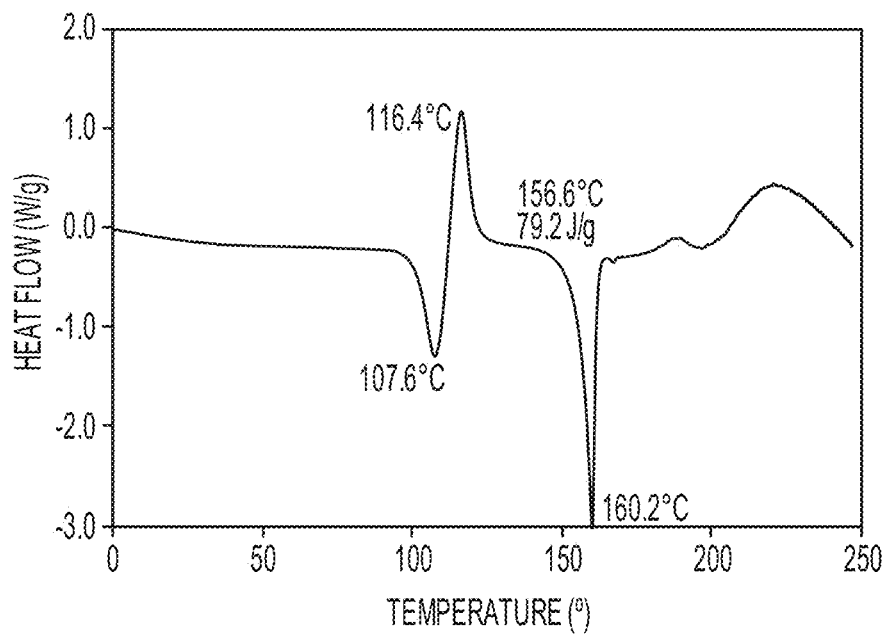
FIG. 9 shows a DSC thermogram.

In one embodiment, the crystalline neutral Form 2 is characterized by the DSC thermogram in FIG. 9. The DSC thermogram showed a melting endotherm with onset and peak temperatures at 156.6° C. and 160.2° C. The enthalpy of fusion is 79.2 J/g. The melting event is preceded by two closely spaced thermal events: an endotherm in the range 100-110° C. and an exotherm in the range 110-120° C.

Figure 10:
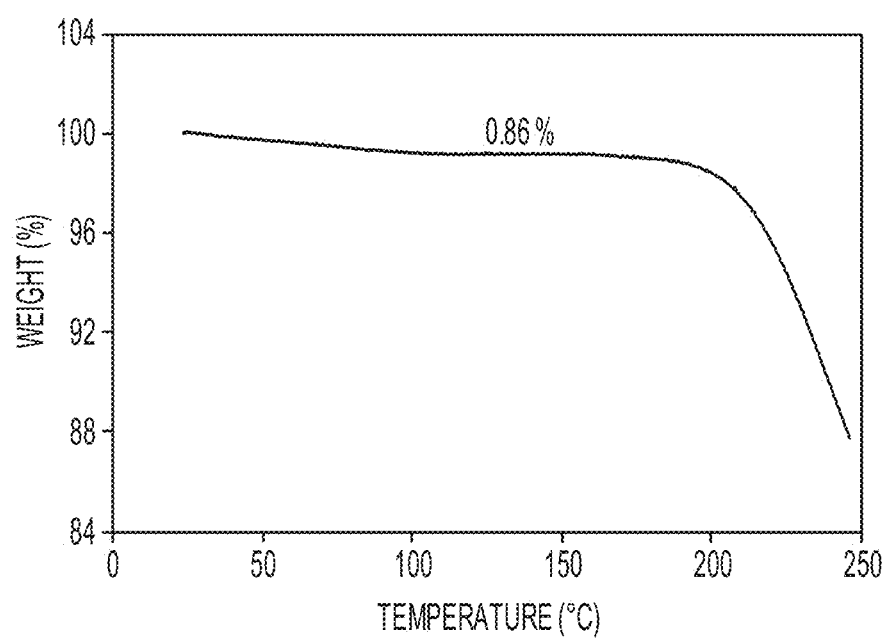
FIG. 10 shows a TGA trace for this form.

In one embodiment, the crystalline neutral Form 2 is characterized by the TGA profile in FIG. 10. The TGA profile showed a weight loss of about 0.86% between 30-110° C. Other batches of Form-2 examined with TGA showed weight losses in the range 0.41-0.93%. Karl-Fisher analysis showed that showed that Form 2 contained 0.67% water. The expected water content in a quarter-hydrate is 0.94%. These observations indicate that Form 2 is either an anhydrous form with some surface adsorbed water or is a quarter (or partial) hydrate. Confirmation can readily be obtained with further studies such as single crystal X-ray diffraction analysis. It is understood however, that Form 2 may be referred to as being an anhydrous form, with the understanding that the solid does contain a small amount of water. Both the DSC and TGA showed heat induced decomposition of Form 2 after 175° C.

Figure 11:
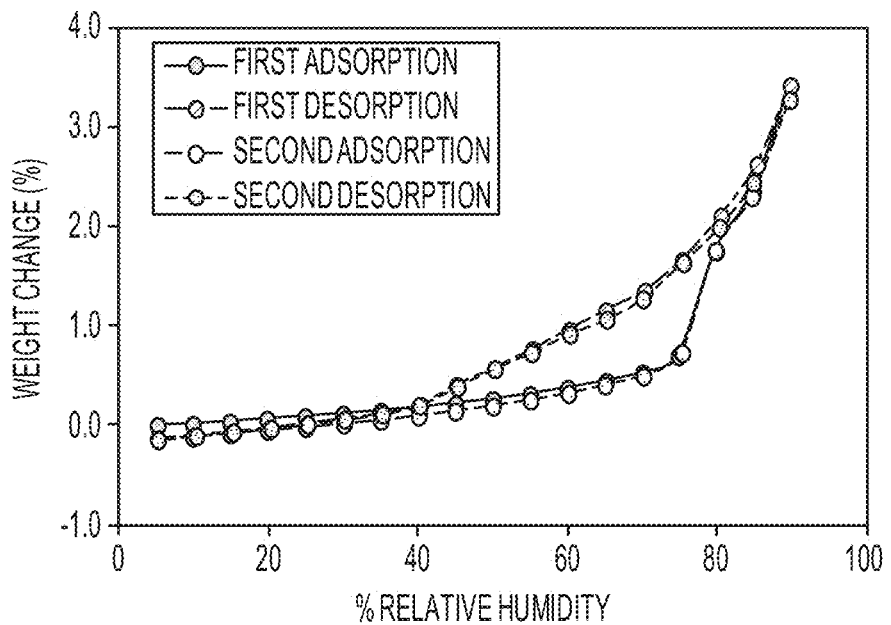
FIG. 11 shows a DMS profile.
Figure 12:
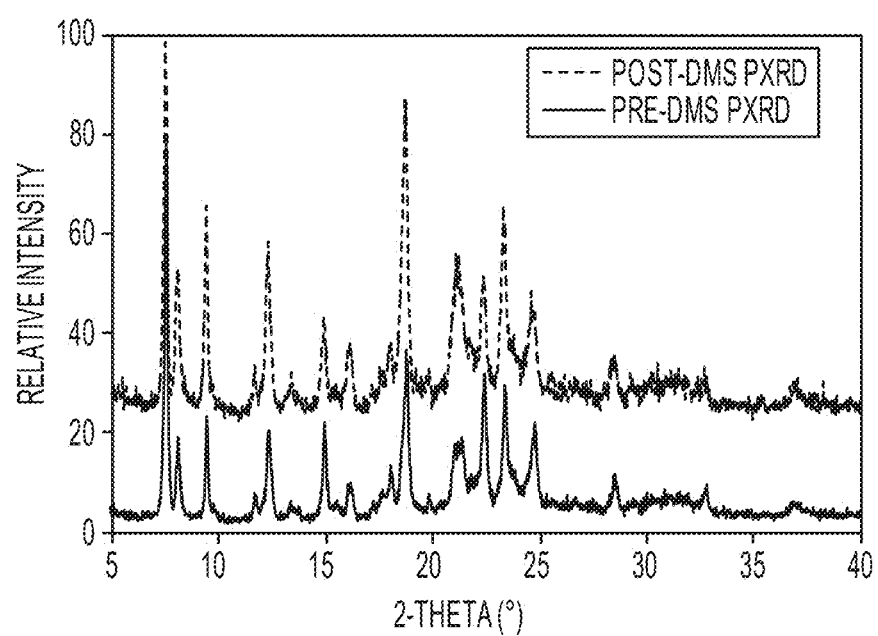
FIG. 12 shows the overlay of the PXRD patterns of the sample before and after being subjected to the moisture sorption-desorption experiment for this form.

In one embodiment, the crystalline neutral Form 2 is characterized by the DMS profile in FIG. 11. Samples of Form 2 were subjected to isothermal moisture sorption analysis at 25° C. With increasing relative humidity, the amount of water adsorbed by the solid increased gradually up to 75% RH and steeply between 75%-90% RH (FIG. 9). The adsorption and desorption segments showed distinct hysteresis, indicating different relative rates of moisture sorption and desorption. The first and second adsorption-desorption cycles, however, showed overlaid profiles, indicating that under these experimental conditions Form 2 adsorbs and loses water in a reproducible manner. The product obtained after the completion of adsorption and desorption showed a PXRD pattern that matched with the starting material (FIG. 12). This matching suggests that Form 2, though takes-up significant moisture, returns to the same solid-state structure after full desorption. Form 2 was found to be hygroscopic.

Figure 13:
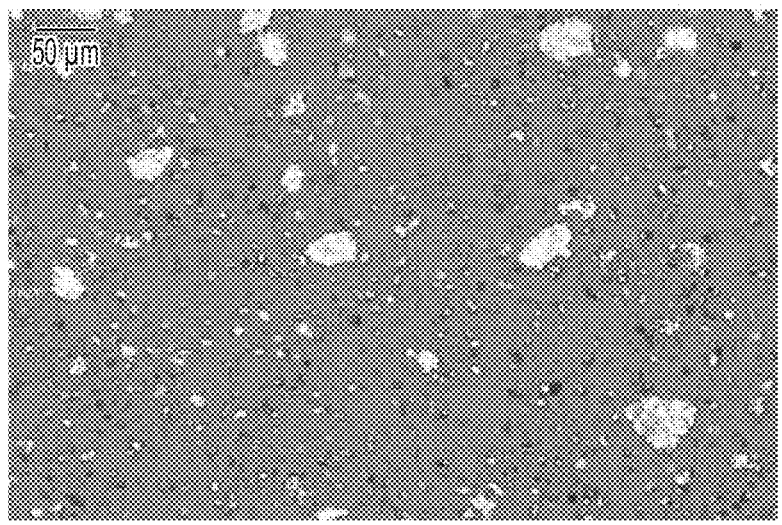
FIG. 13.
Figure 14:
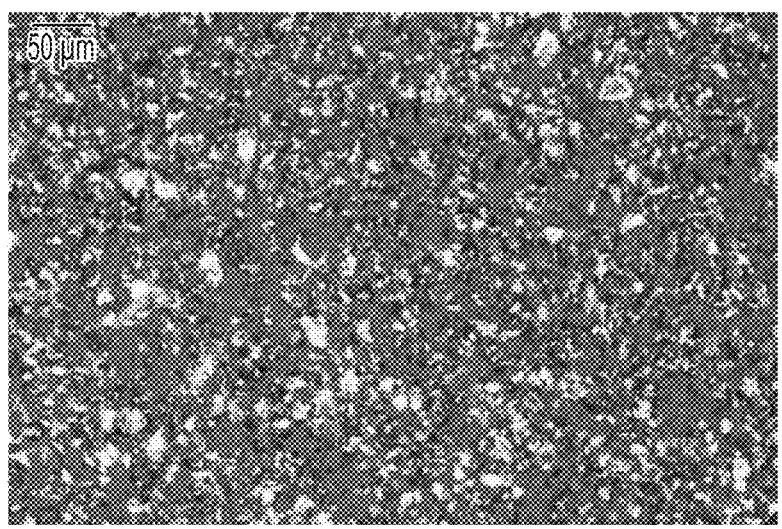
FIG. 14 are PLM images of this form.

The crystalline neutral Form 2 is a white solid with plate-like particles having sizes in the range of 1-30 μm. The particles are birefringent under cross-polarized light suggesting their crystallinity. Form 2 has only been crystallized under agitated conditions, which has led to particles with broken edges. Form 2 can be characterized by the PLM image in FIG. 13 (using material of Example 5) and FIG. 14 (using material of Example 6).

Crystalline Neutral Solvated Form 2'

Figure 17:
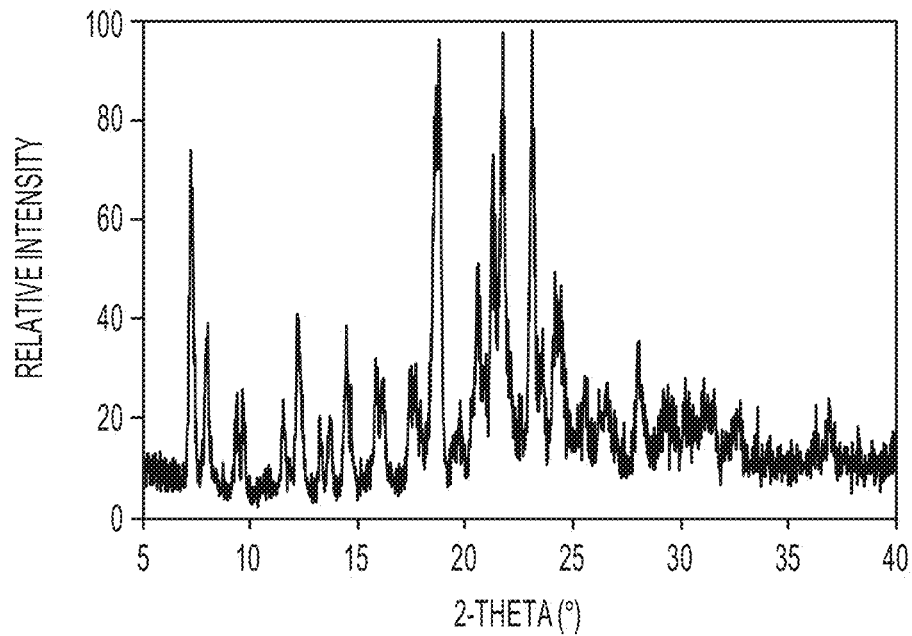
FIG. 17 and FIG. 18 show PXRD patterns of the crystalline neutral solvated Form 2' obtained from ethyl acetate/hexanes and ethyl acetate, respectively.

The crystalline neutral solvated Form 2' is characterized by a PXRD pattern in which the peak positions are substantially in accordance with those shown in FIG. 17 (crystalline neutral solvated Form 2' obtained from ethyl acetate/hexanes) and 18 (crystalline neutral solvated Form 2' obtained from ethyl acetate). Peaks above 15% relative height are listed in the table below.

| 2θ | d (Å) | Height[1] | H %[2] | * |
|---|---|---|---|---|
| 2.20 | 40.14 | 105 | 27.4 | |
| 7.26 | 12.16 | 293 | 76.5 | * |
| 8.05 | 10.97 | 138 | 36.1 | * |
| 9.41 | 9.39 | 87 | 22.6 | |
| 9.66 | 9.15 | 91 | 23.7 | |
| 12.20 | 7.25 | 156 | 40.7 | * |
| 13.25 | 6.67 | 67 | 17.5 | |
| 13.72 | 6.45 | 66 | 17.3 | |
| 14.48 | 6.11 | 146 | 38.2 | * |
| 15.84 | 5.59 | 112 | 29.3 | * |
| 16.22 | 5.46 | 93 | 24.2 | * |
| 17.42 | 5.09 | 91 | 23.7 | |
| 18.78 | 4.72 | 383 | 100 | * |
| 19.75 | 4.49 | 62 | 16.3 | |
| 20.60 | 4.31 | 183 | 47.8 | * |
| 21.29 | 4.17 | 221 | 57.8 | * |
| 21.74 | 4.09 | 339 | 88.4 | * |
| 23.10 | 3.85 | 362 | 94.6 | * |
| 23.60 | 3.77 | 98 | 25.6 | |
| 24.16 | 3.68 | 138 | 36.0 | * |
| 24.44 | 3.64 | 134 | 35.0 | * |
| 26.56 | 3.35 | 64 | 16.8 | |
| 28.06 | 3.18 | 101 | 26.3 | |
| 31.54 | 2.83 | 61 | 16.0 | |
| 32.75 | 2.73 | 61 | 15.9 | |
| 36.86 | 2.44 | 58 | 15.1 | |

[1]Peak height from base line
[2]Percent peak height compared to highest peak
* Indicates peaks that are important to identify this form Thus, in one embodiment, the crystalline neutral solvated Form 2' is characterized by a PXRD pattern comprising diffraction peaks at 2θ values of 7.26±0.20, 8.05±0.20, 12.20±0.20, 14.48±0.20, 15.84±0.20, 16.22±0.20, 18.78±0.20, 20.60±0.20, 21.29±0.20, 21.74±0.20, 23.10±0.20, 24.16±0.20, and 24.44±0.20; and further characterized by having one or more additional diffraction peaks at 2θ values selected from 2.20±0.20, 9.41±0.20, 9.66±0.20, 13.25±0.20, 13.72±0.20, 17.42±0.20, 19.75±0.20, 23.60±0.20, 26.56±0.20, 28.06±0.20, 31.54±0.20, 32.75±0.20, and 36.86±0.20.

Figure 19:
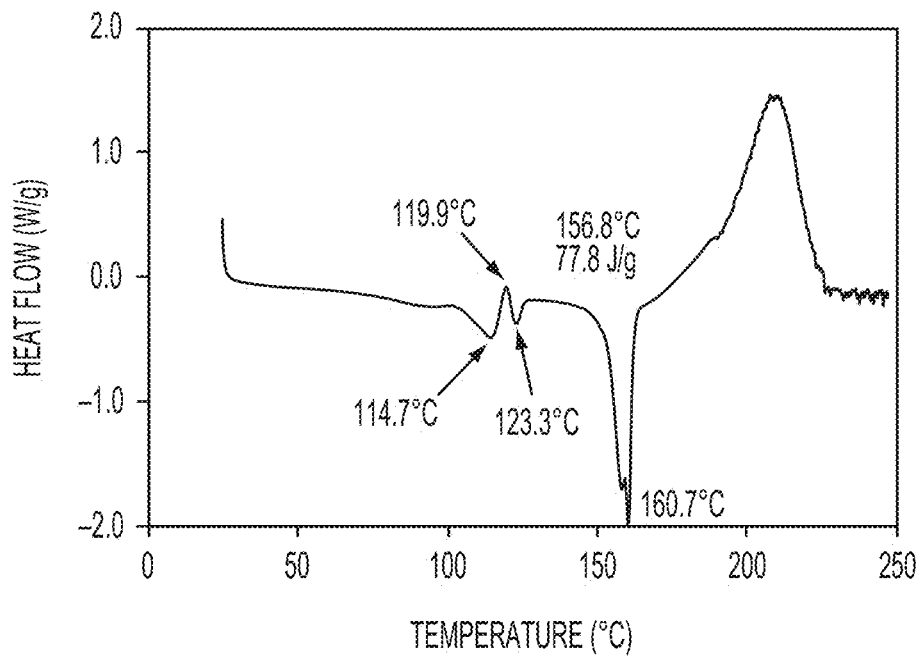
FIG. 19 and FIG. 20 show DSC thermograms.
Figure 20:
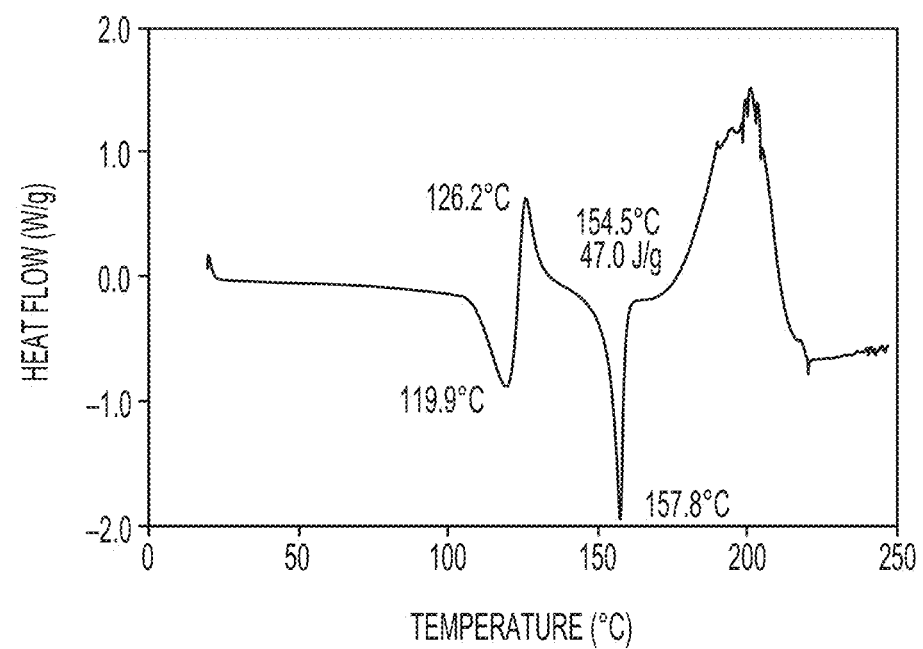

In one embodiment, the crystalline neutral solvated Form 2' is obtained from ethyl acetate/hexanes and is characterized by the DSC thermogram in FIG. 19; and in another embodiment, the crystalline neutral solvated Form 2' is obtained from ethyl acetate and is characterized by the DSC thermogram in FIG. 20. The DSC thermograms demonstrates that this crystalline compound exhibits a melting endotherm onset within the range of about 157-161° C.

Figure 21:
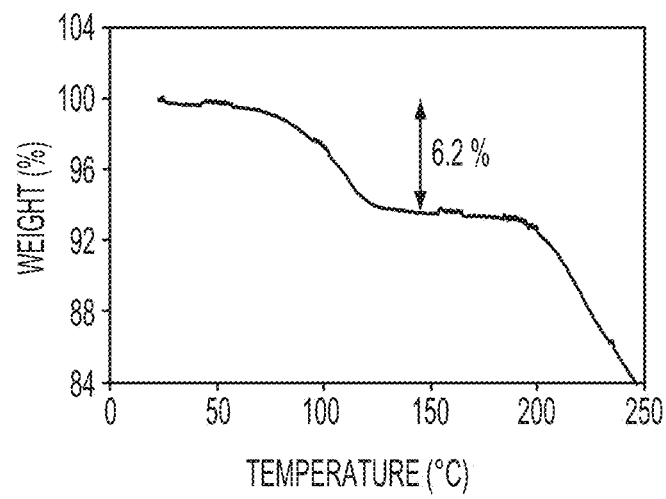
FIG. 21 and FIG. 22 show TGA traces for this form obtained from ethyl acetate/hexanes and ethyl acetate, respectively.
Figure 22:
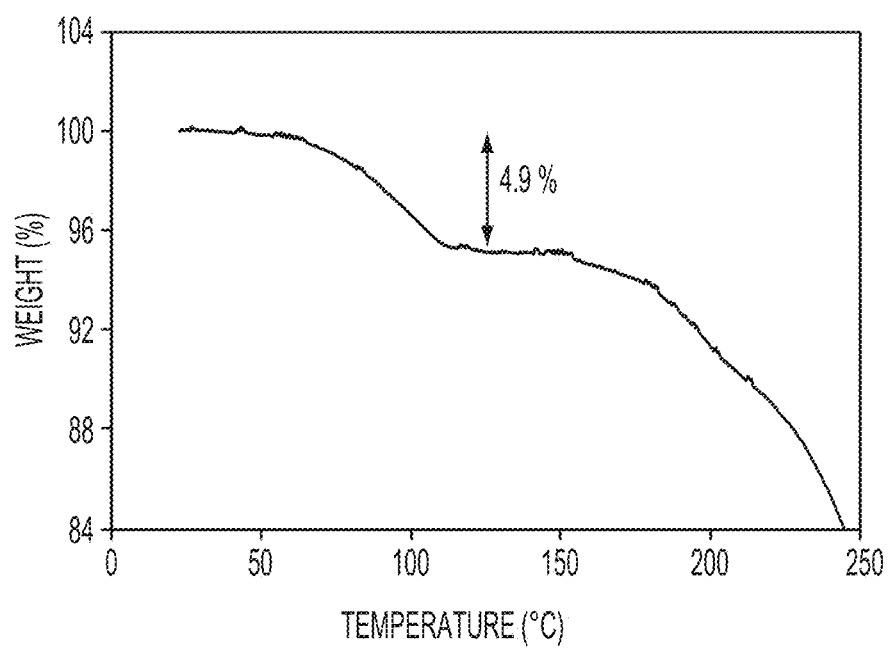

In one embodiment, the crystalline neutral solvated Form 2' is obtained from ethyl acetate/hexanes and is characterized by the TGA profile in FIG. 21; and in another embodiment, the crystalline neutral solvated Form 2' is obtained from ethyl acetate and is characterized by the TGA profile in FIG. 22. The crystalline neutral solvated Form 2' is isostructural to the crystalline neutral anhydrous Form 2 because it has a PXRD pattern and DSC thermogram similar to Form 2 but contains a greater amount of lattice solvent, as evidenced by the TGA profile. The TGA profile of Form 2' showed a much larger weight loss (6.2% for Form 2' obtained from ethyl acetate/hexanes, FIG. 21, and 4.9% for Form 2' obtained from ethyl acetate) compared to the 0.86% found in Form 2 (FIG. 10).

Figure 23:
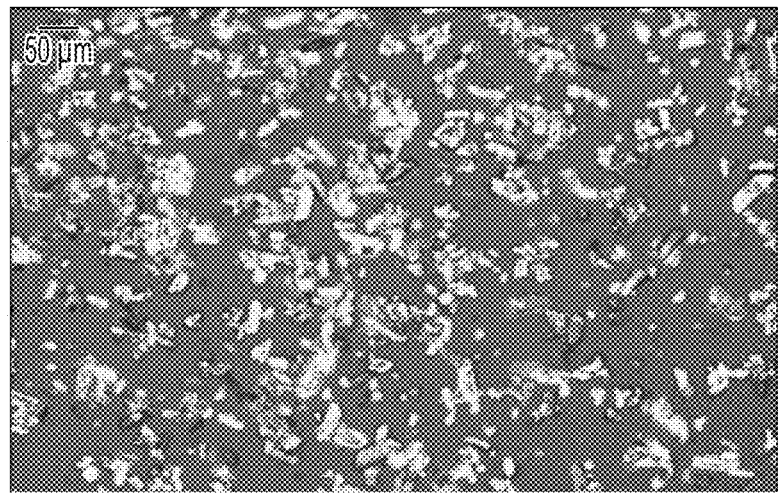
FIG. 23 and FIG. 24 are PLM images of this form obtained from ethyl acetate/hexanes and ethyl acetate, respectively.
Figure 24:
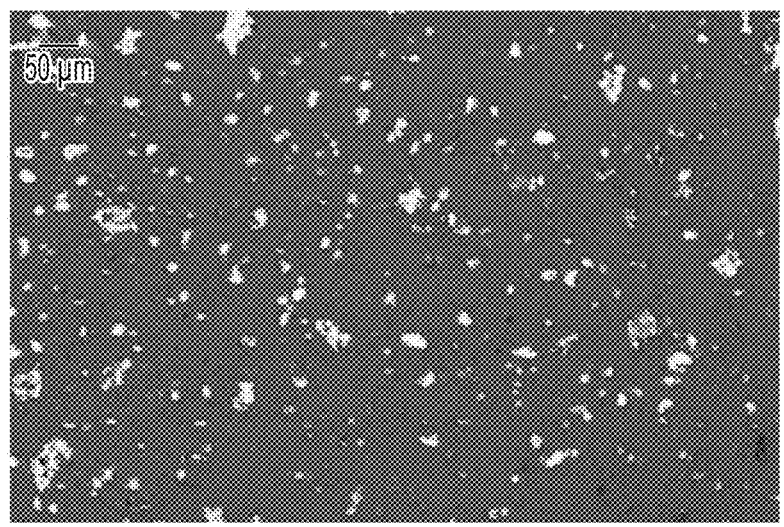

In another embodiment, the crystalline neutral solvated Form 2' is characterized by the PLM image in FIG. 23 for Form 2' obtained from ethyl acetate/hexanes and FIG. 24 for Form 2' obtained from ethyl acetate.

Crystalline Neutral Anhydrous Form 3

Figure 25:
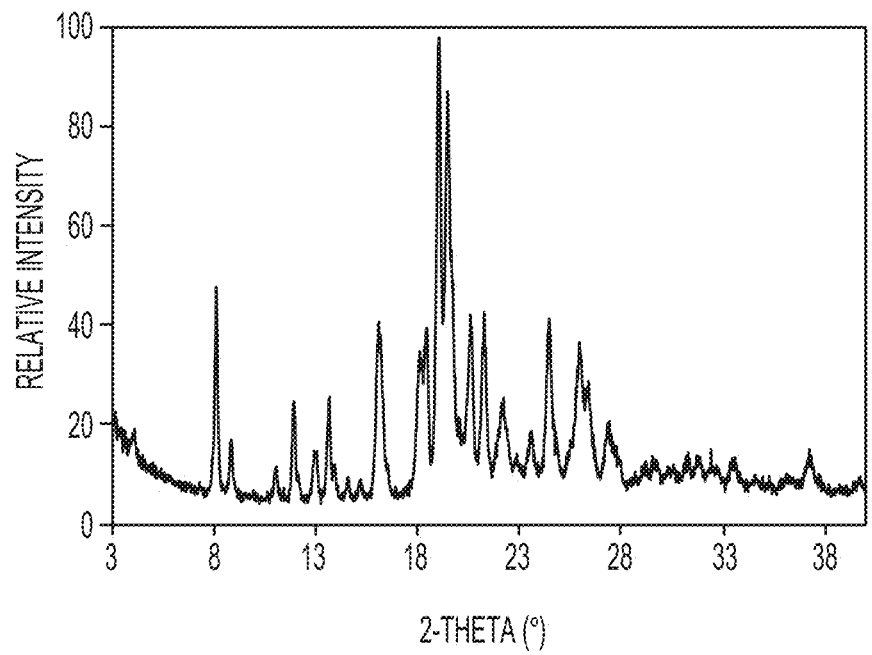
FIG. 25 shows a PXRD pattern of the crystalline neutral anhydrous Form 3.

The crystalline neutral anhydrous Form 3 is characterized by a PXRD pattern in which the peak positions are substantially in accordance with those shown in FIG. 25. All peaks are listed in the table below.

| 2θ | d (Å) | Height[1] | H %[2] | * |
|---|---|---|---|---|
| 8.12 | 10.88 | 183.0 | 49.9 | * |
| 8.86 | 9.97 | 48.0 | 13.1 | * |
| 11.06 | 7.99 | 27.0 | 7.4 | |
| 11.92 | 7.42 | 85.0 | 23.2 | * |
| 12.94 | 6.84 | 41.0 | 11.1 | |
| 13.68 | 6.47 | 89.0 | 24.1 | * |
| 13.94 | 6.35 | 28.0 | 7.6 | |
| 16.10 | 5.50 | 156.0 | 42.5 | * |
| 18.12 | 4.89 | 128.0 | 34.8 | * |
| 18.46 | 4.80 | 119.0 | 32.3 | * |
| 19.06 | 4.65 | 368.0 | 100 | * |
| 19.48 | 4.55 | 317.0 | 86.2 | * |
| 20.60 | 4.31 | 117.0 | 31.9 | * |
| 21.28 | 4.17 | 135.0 | 36.7 | * |
| 22.12 | 4.02 | 60.0 | 16.4 | |
| 23.58 | 3.77 | 37.0 | 9.9 | |
| 24.46 | 3.64 | 137.0 | 37.2 | * |
| 25.94 | 3.43 | 117.0 | 31.8 | * |
| 26.40 | 3.37 | 76.0 | 20.7 | * |
| 27.32 | 3.26 | 48.0 | 13.1 | |
| 32.40 | 2.76 | 26.0 | 7.1 | |
| 33.46 | 2.68 | 24.0 | 6.6 | |
| 37.24 | 2.41 | 34.0 | 9.3 | |

[1]Peak height from base line
[2]Percent peak height compared to highest peak
* Indicates peaks that are important to identify this form Thus, in one embodiment, the crystalline neutral anhydrous Form 3 is characterized by a PXRD pattern comprising diffraction peaks at 2θ values of 8.12±0.20, 8.86±0.20, 11.92±0.20, 13.68±0.20, 16.10±0.20, 18.12±0.20, 18.46±0.20, 19.06±0.20, 19.48±0.20, 20.60±0.20, 21.28±0.20, 24.46±0.20, 25.94±0.20, and 26.40±0.20; and further characterized by having one or more additional diffraction peaks at 2θ values selected from 11.06±0.20, 12.94±0.20, 13.94±0.20, 22.12±0.20, 23.58±0.20, 27.32±0.20, 32.40±0.20, 33.46±0.20, and 37.24±0.20.

Figure 26:
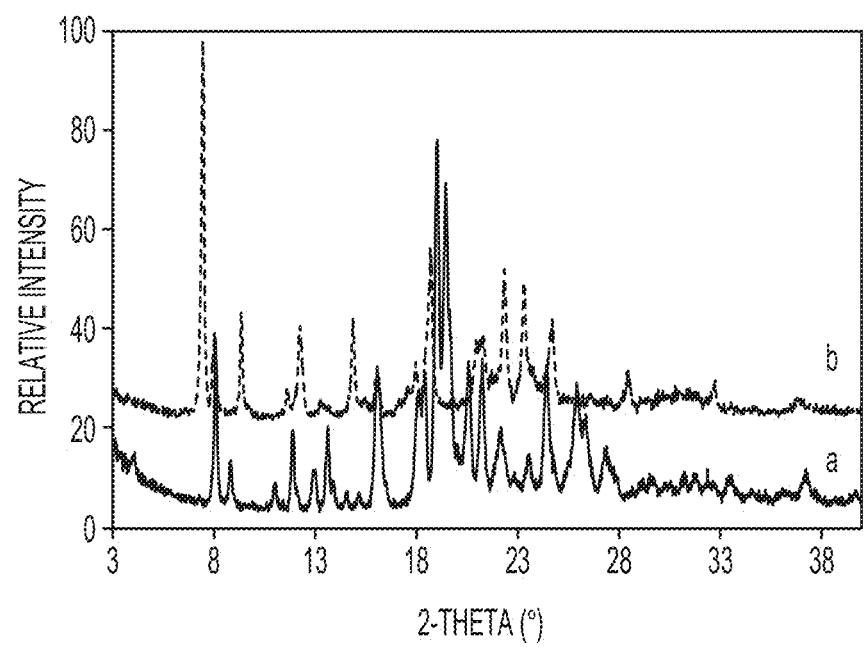
FIG. 26 depicts the PXRD pattern of the crystalline neutral anhydrous Form 3 (FIG. 26-a) compared to that of Form 2 (FIG. 26-b).

Comparison of the PXRD patterns of heat-cooled samples of Form 3 (FIG. 26-a) with the starting material Form 2 (FIG. 26-b) showed differences in peak positions and intensities throughout the diffraction window, suggesting the change in phase structure.

Figure 27:
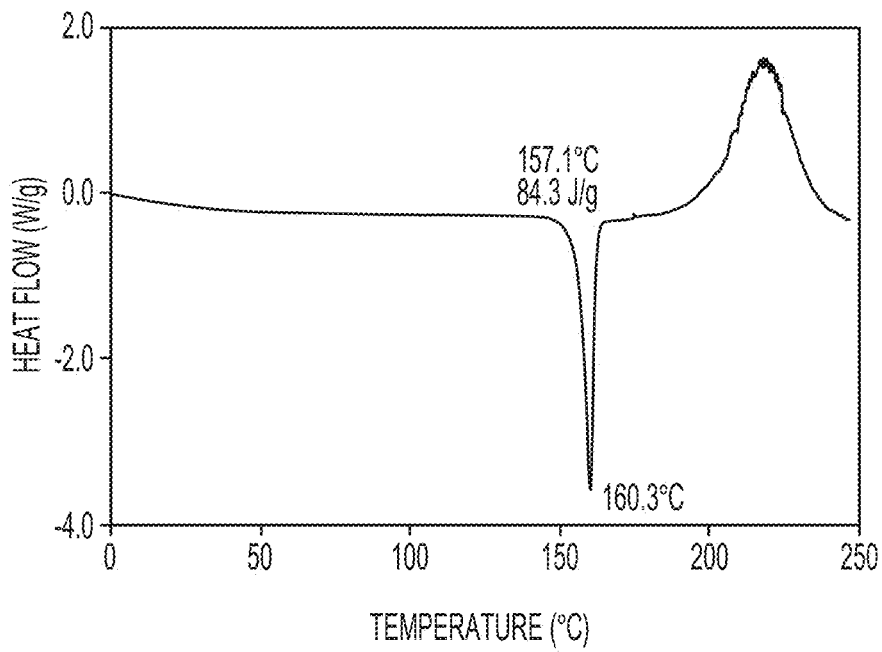
FIG. 27 shows a DSC thermogram.
Figure 28:
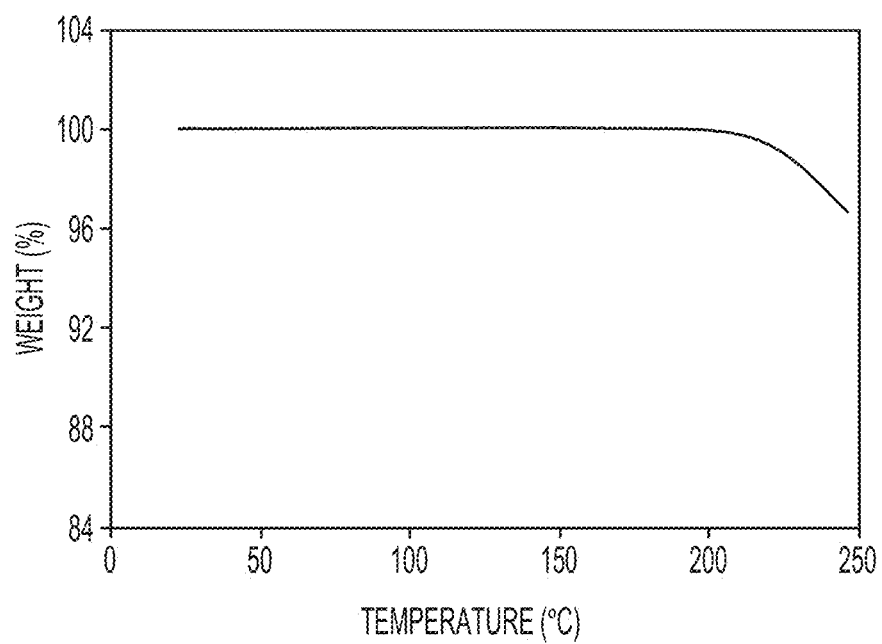
FIG. 28 shows a TGA trace for this form.

In one embodiment, the crystalline neutral anhydrous Form 3 is characterized by the DSC thermogram in FIG. 27. The DSC thermogram demonstrates that this crystalline compound exhibits a melting endotherm onset at about 157.0° C. and endotherm peak at about 160.3° C. (melting point), thus having a melting point within the range of about 157-161° C., with a melting enthalpy of 86.0 J/g. No other thermal events prior to the melting transition were observed. In one embodiment, the crystalline neutral anhydrous Form 3 is characterized by the TGA profile in FIG. 28. The TGA trace shows no weight loss until after the melting temperature. These results indicate that Form 3 is an anhydrous form.

Figure 29:
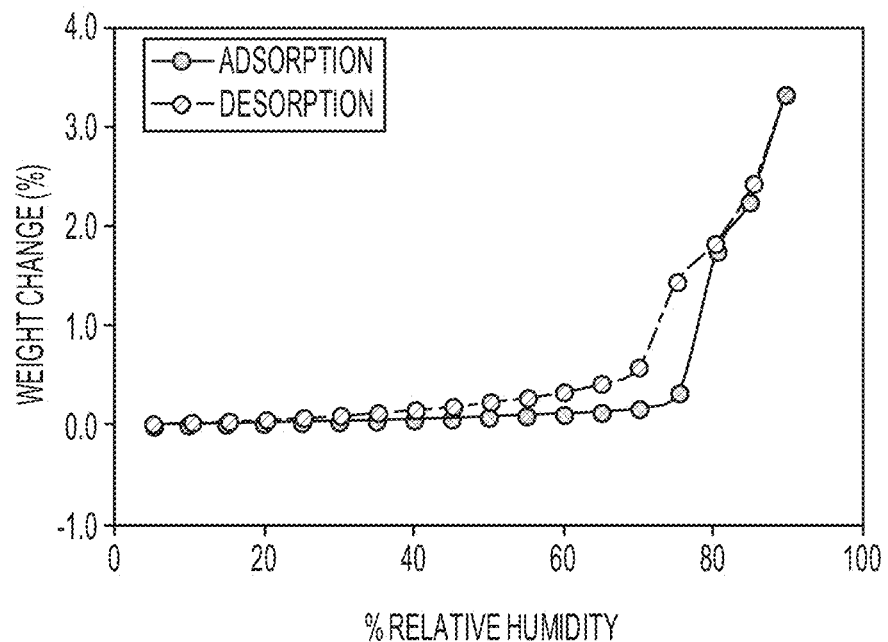
FIG. 29 shows a DMS profile.
Figure 30:
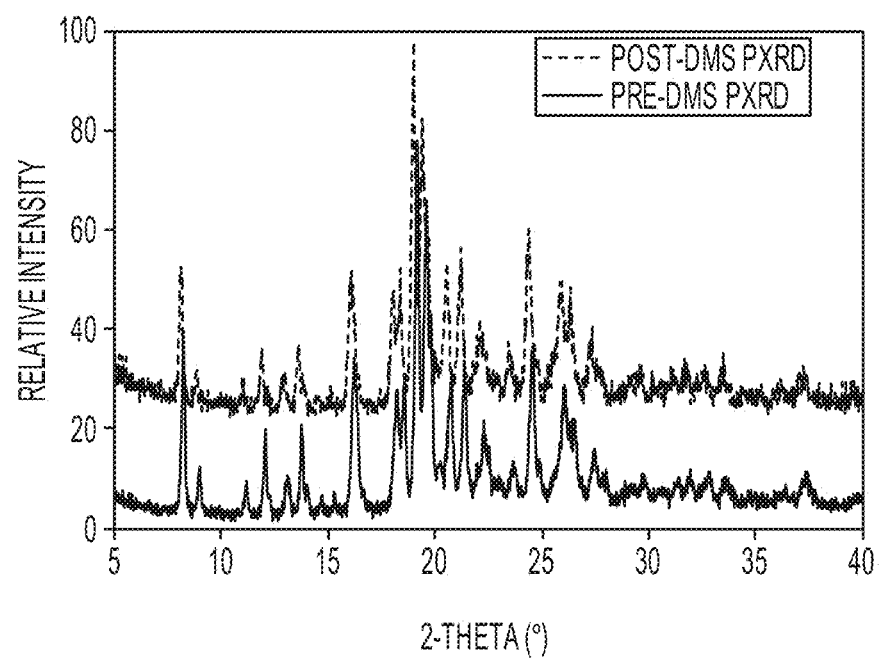
FIG. 30 shows the overlay of the PXRD patterns of the sample before and after being subjected to the moisture sorption-desorption experiment for this form.

In one embodiment, the crystalline neutral anhydrous Form 3 is characterized by the DMS profile in FIG. 29. The DMS thermogram of Form 3 is similar to that of Form 2 (FIG. 11). At up to 75% RH, Form 3 does not take-up much water, but between 75% RH and 90% RH it takes up about 3.5% water, indicating that it is potentially converting to a hydrate form. The sample, however, loses the adsorbed water during desorption segment and returns to an anhydrous state. Overlay of the PXRD patterns of the sample before and after it was subjected the moisture sorption-desorption experiment is shown in FIG. 30. Under the conditions employed in the DMS experiment, Form 3 returns to the same solid form after moisture sorption and desorption. Form 3, like Form 2, is hygroscopic.

Figure 31:
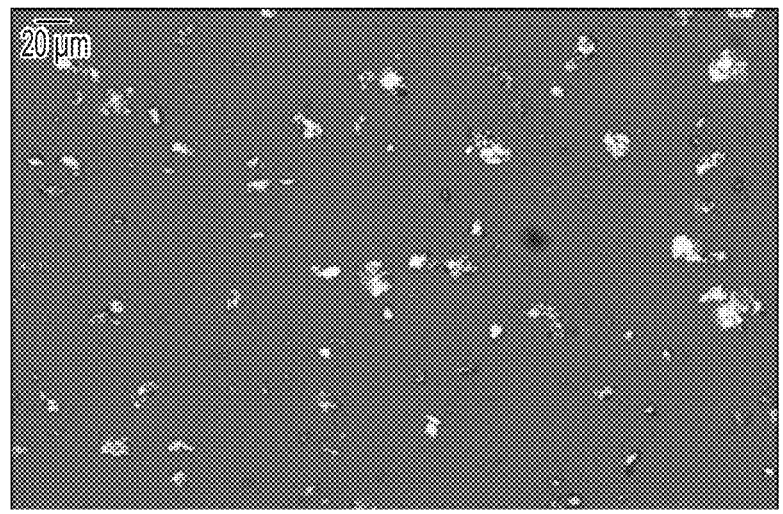
FIG. 31 and FIG. 32 are PLM images of this form.
Figure 32:
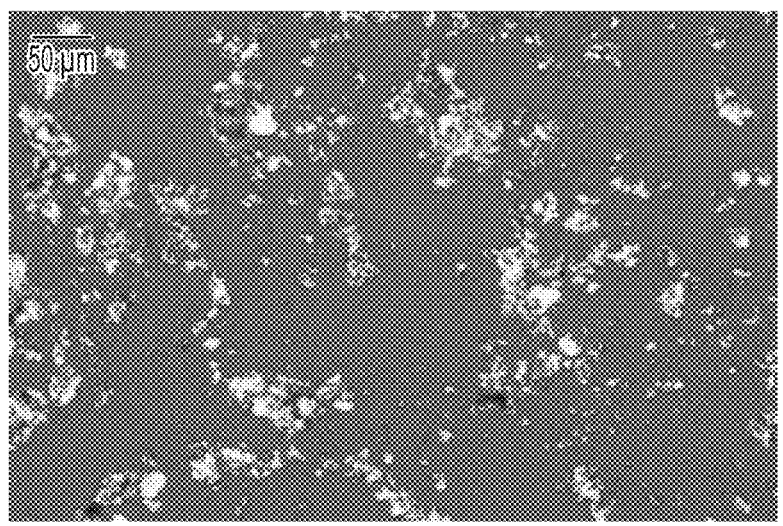

In another embodiment, the crystalline neutral anhydrous Form 3 is characterized by the PLM images in FIG. 31 (using material of Example 10) and FIG. 32 (using material of Example 11), which show these particles as being birefringent, suggesting their crystallinity.

Crystalline Neutral Anhydrous Form 4

Figure 33:
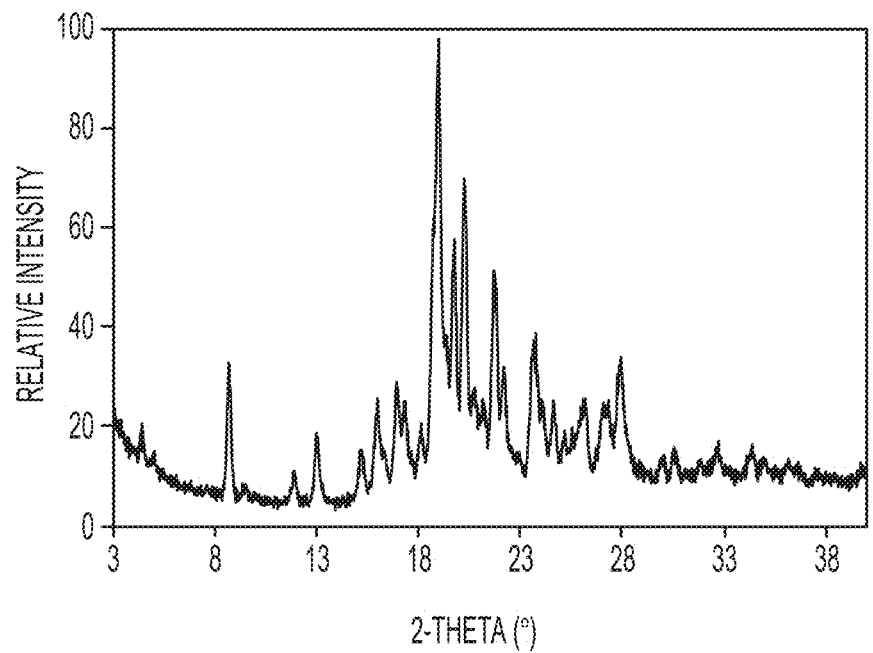
FIG. 33 shows a PXRD pattern of the crystalline neutral anhydrous Form 4.

The crystalline neutral anhydrous Form 4 is characterized by a PXRD pattern in which the peak positions are substantially in accordance with those shown in FIG. 33. Peaks above 5% relative height are listed in the table below.

| 2θ | d (Å) | Height[1] | H %[2] | * |
|---|---|---|---|---|
| 4.44 | 19.87 | 26 | 7.8 | |
| 8.70 | 10.16 | 104 | 31.5 | * |
| 11.90 | 7.43 | 25 | 7.5 | |
| 13.00 | 6.80 | 55 | 16.7 | * |
| 15.18 | 5.83 | 34 | 10.4 | |
| 16.00 | 5.54 | 67 | 20.5 | * |
| 16.34 | 5.42 | 22 | 6.8 | |
| 16.94 | 5.23 | 74 | 22.4 | * |
| 17.36 | 5.11 | 56 | 17.1 | * |
| 18.14 | 4.89 | 29 | 8.8 | |
| 18.72 | 4.74 | 191 | 58.1 | * |
| 19.00 | 4.67 | 329 | 100.0 | * |
| 19.78 | 4.49 | 108 | 32.9 | * |
| 20.24 | 4.38 | 167 | 50.9 | * |
| 20.77 | 4.27 | 18 | 5.5 | |
| 21.20 | 4.19 | 18 | 5.6 | |
| 21.70 | 4.09 | 132 | 40.3 | * |
| 22.20 | 4.00 | 65 | 19.8 | |
| 23.68 | 3.76 | 95 | 28.9 | * |
| 24.10 | 3.69 | 49 | 14.8 | |
| 24.62 | 3.61 | 41 | 12.3 | |
| 25.66 | 3.47 | 20 | 6.2 | |
| 26.18 | 3.40 | 49 | 14.9 | |
| 27.08 | 3.29 | 37 | 11.2 | |
| 27.94 | 3.19 | 68 | 20.7 | * |
| 30.54 | 2.93 | 23 | 7.0 | |
| 32.74 | 2.73 | 24 | 7.3 | |
| 34.40 | 2.61 | 25 | 7.6 | |

[1]Peak height from base line
[2]Percent peak height compared to highest peak
* Indicates peaks that are important to identify this form Thus, in one embodiment, the crystalline neutral anhydrous Form 4 is characterized by a PXRD pattern comprising diffraction peaks at 2θ values of 8.70±0.20, 13.00±0.20, 16.00±0.20, 16.94±0.20, 17.36±0.20, 18.72±0.20, 19.00±0.20, 19.78±0.20, 20.24±0.20, 21.70±0.20, 23.68±0.20, and 27.94±0.20; and further characterized by having one or more additional diffraction peaks at 2θ values selected from 4.44±0.20, 11.90±0.20, 15.18±0.20, 16.34±0.20, 18.14±0.20, 20.77±0.20, 21.20±0.20, 22.20±0.20, 24.10±0.20, 24.62±0.20, 25.66±0.20, 26.18±0.20, 27.08±0.20, 30.54±0.20, 32.74±0.20, and 34.40±0.20.

Figure 34:
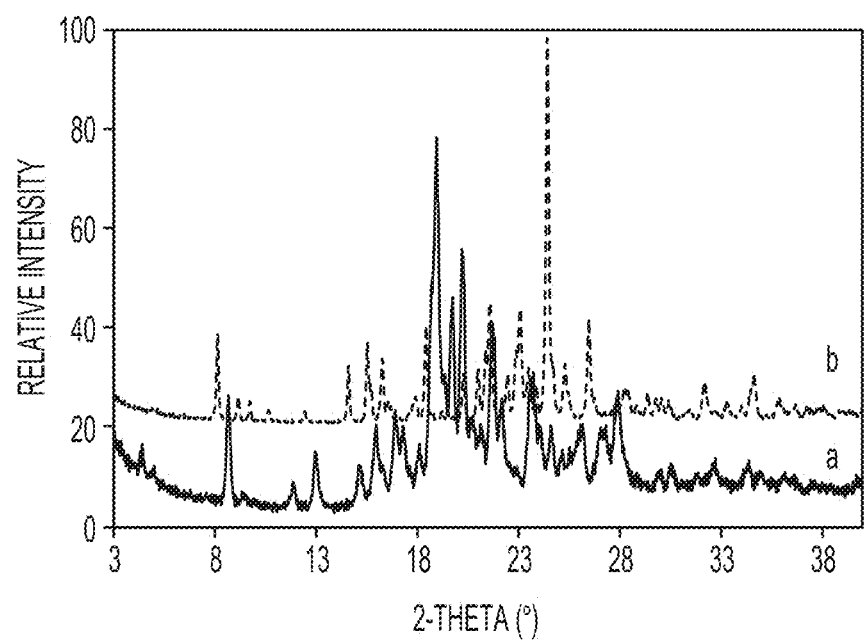
FIG. 34 depicts the PXRD pattern of the crystalline neutral anhydrous Form 4 (FIG. 34-a) compared to that of Form 1 (FIG. 34-b).

Comparison of the PXRD patterns of heat-cooled samples of Form 4 (FIG. 34-a) with the starting material Form 1 (FIG. 34-b) showed differences in peak positions and intensities throughout the diffraction window, suggesting the change in phase structure.

Figure 35:
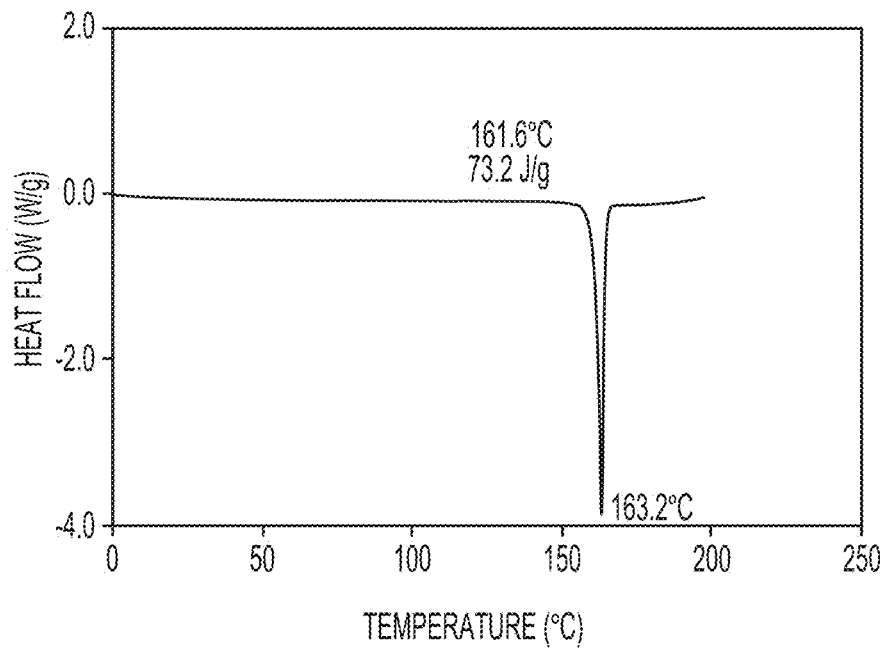
FIG. 35 shows a DSC thermogram.
Figure 36:
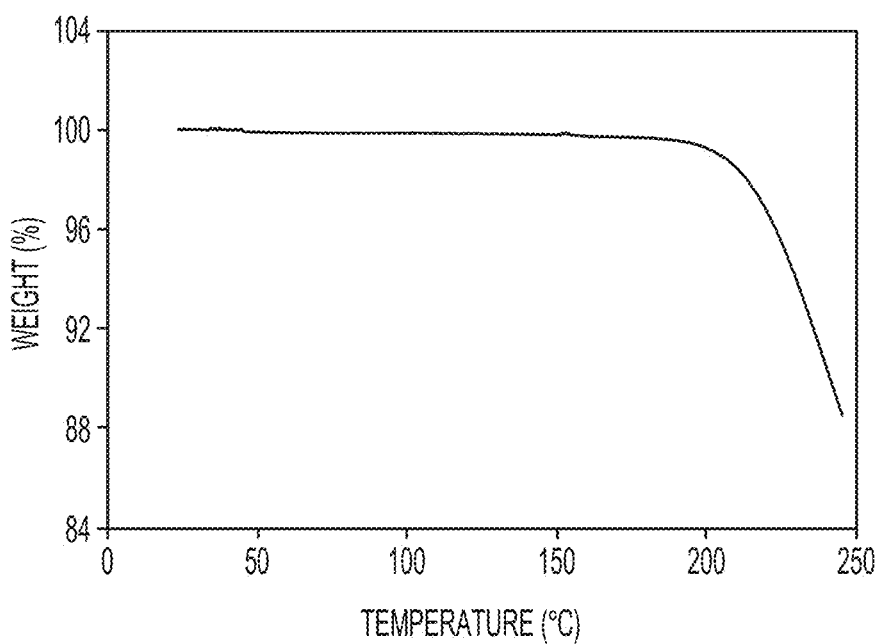
FIG. 36 shows a TGA trace for this form.

In one embodiment, the crystalline neutral anhydrous Form 4 is characterized by the DSC thermogram in FIG. 35. The DSC thermogram demonstrates that this crystalline compound exhibits a melting endotherm onset at about 161.6° C. and endotherm peak at about 163.2° C. (melting point), thus having a melting point within the range of about 161-164° C., with a melting enthalpy of 73.2 J/g. No other thermal events prior to the melting endotherm were observed. In one embodiment, the crystalline neutral anhydrous Form 4 is characterized by the TGA profile in FIG. 36. The TGA trace shows no weight loss until after the melting temperature. These results indicate that Form 4 is an anhydrous form.

Figure 37:
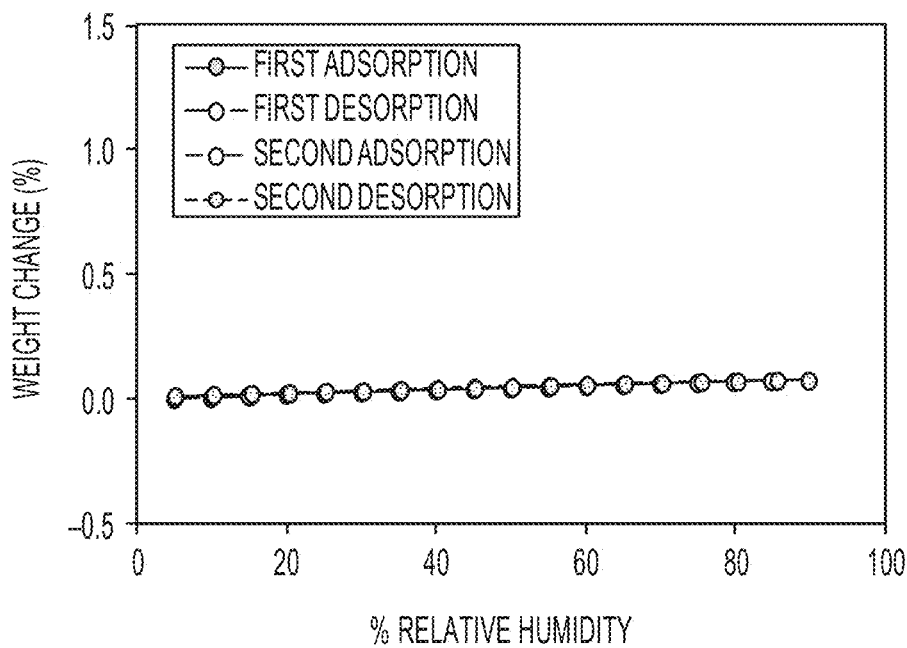
FIG. 37 shows a DMS profile.

In one embodiment, the crystalline neutral anhydrous Form 4 is characterized by the DMS profile in FIG. 37. The DMS thermogram of Form 4 showed that Form 4 takes up less than 0.1% by weight of water when exposed up to 90% RH. Form-4 is non-hygroscopic. Two successive cycles of adsorption and desorption showed no hysteresis and the sample retained its solid-state structure after the DMS experiment. Form 4, which is obtained from the monohydrate Form 1, is non-hygroscopic, whereas Form 3, which is obtained from anhydrous Form 2, is hygroscopic. On the other hand, Form 2 itself is hygroscopic, whereas Form 1 is only slightly hygroscopic. Overlay of the PXRD patterns of the sample before and after it was subjected the moisture sorption-desorption experiment is shown in FIG. 30. Under the conditions employed in the DMS experiment, Form 4 returns to the same solid form after moisture sorption and desorption.

Figure 39:
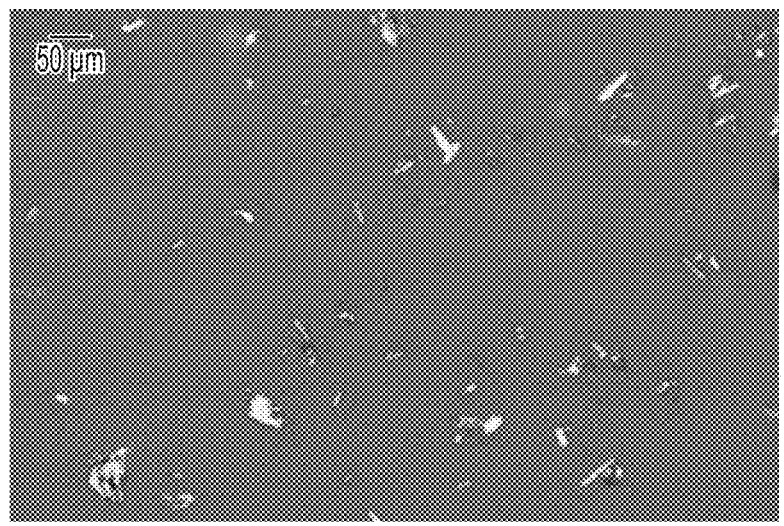
FIG. 39 and FIG. 40 are PLM images of this form.
Figure 40:
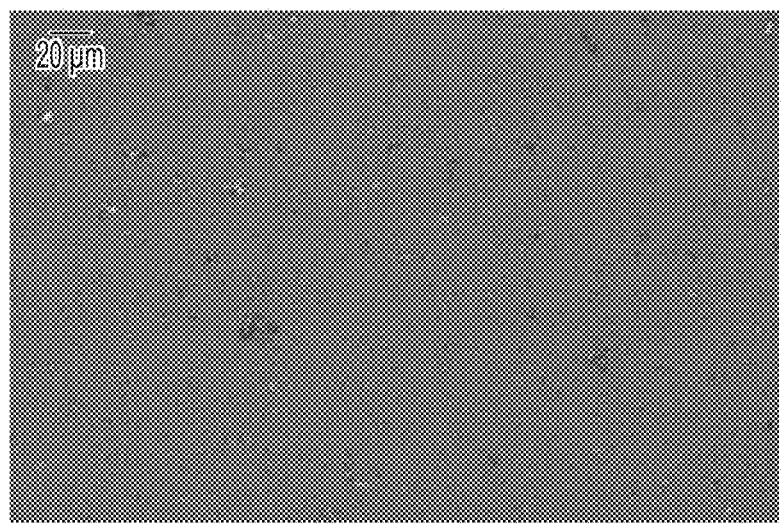

In another embodiment, the crystalline neutral anhydrous Form 4 is characterized by the PLM images in FIG. 39 (using material of Example 12) and FIG. 40 (using material of Example 13), which show these particles as being birefringent, suggesting their crystallinity.

Crystalline Tromethamine Salt

Figure 41:
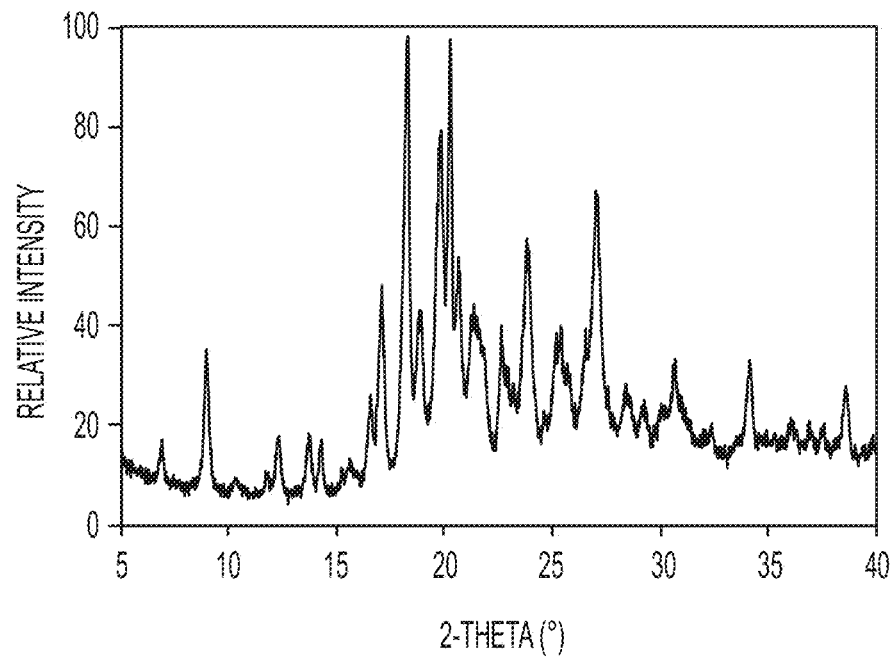
FIG. 41 shows a PXRD pattern of the crystalline tromethamine salt.

The crystalline tromethamine salt is characterized by a PXRD pattern in which the peak positions are substantially in accordance with those shown in FIG. 41. Peaks above 10% relative height are listed in the table below.

| 2θ | d (Å) | Height[1] | H %[2] | * |
|---|---|---|---|---|
| 6.94 | 12.73 | 29 | 10.4 | * |
| 9.00 | 9.82 | 96 | 34.8 | * |
| 12.36 | 7.16 | 41 | 15.0 | * |
| 13.74 | 6.44 | 42 | 15.3 | * |
| 14.32 | 6.18 | 36 | 13.1 | |
| 16.58 | 5.34 | 54 | 19.6 | * |
| 17.12 | 5.18 | 125 | 45.0 | * |
| 18.32 | 4.84 | 277 | 100.0 | * |
| 18.86 | 4.70 | 78 | 28.2 | |
| 19.86 | 4.47 | 183 | 66.2 | * |
| 20.28 | 4.38 | 246 | 89.1 | * |
| 20.66 | 4.30 | 64 | 23.1 | |
| 21.36 | 4.16 | 62 | 22.4 | * |
| 21.76 | 4.08 | 49 | 17.8 | |
| 22.64 | 3.92 | 72 | 26.2 | |
| 23.82 | 3.73 | 121 | 43.8 | * |
| 25.20 | 3.53 | 66 | 23.9 | |
| 25.70 | 3.46 | 42 | 15.2 | |
| 26.54 | 3.36 | 61 | 21.9 | |
| 27.00 | 3.30 | 161 | 58.2 | * |
| 28.42 | 3.14 | 33 | 11.9 | |
| 30.70 | 2.91 | 53 | 19.1 | |
| 34.12 | 2.63 | 58 | 20.9 | |
| 38.58 | 2.33 | 49 | 17.7 | |

[1]Peak height from base line
[2]Percent peak height compared to highest peak
* Indicates peaks that are important to identify this form Thus, in one embodiment, the crystalline tromethamine salt is characterized by a PXRD pattern comprising diffraction peaks at 2θ values of 6.94±0.20, 9.00±0.20, 12.36±0.20, 13.74±0.20, 16.58±0.20, 17.12±0.20, 18.32±0.20, 19.86±0.20, 20.28±0.20, 21.36±0.20, 23.82±0.20, and 27.00±0.20; and further characterized by having one or more additional diffraction peaks at 2θ values selected from 14.32±0.20, 18.86±0.20, 20.66±0.20, 21.76±0.20, 22.64±0.20, 25.20±0.20, 25.70±0.20, 26.54±0.20, 28.42±0.20, 30.70±0.20, 34.12±0.20, and 38.58±0.20.

Figure 42:
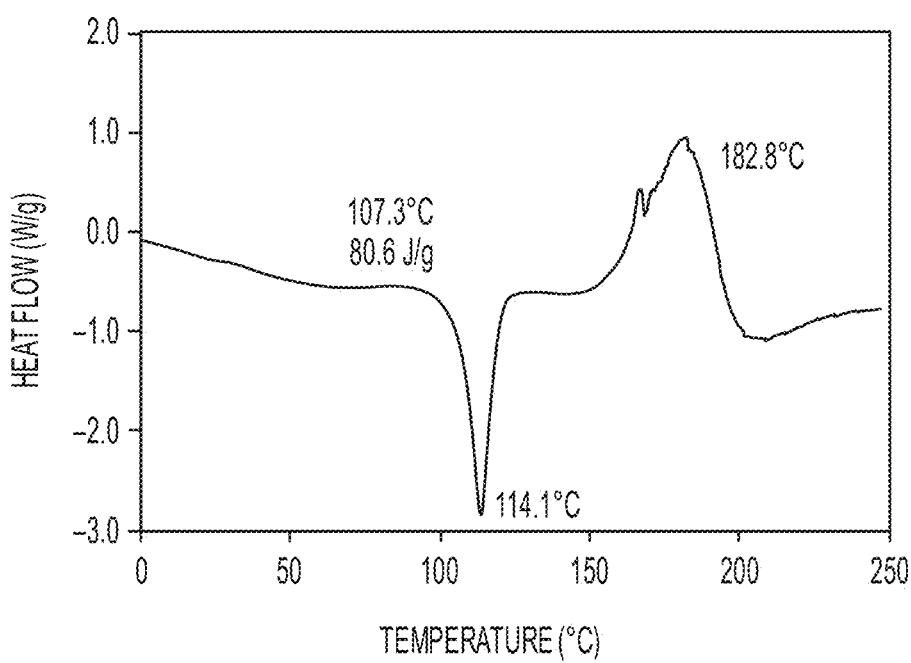
FIG. 42 shows a DSC thermogram.
Figure 43:
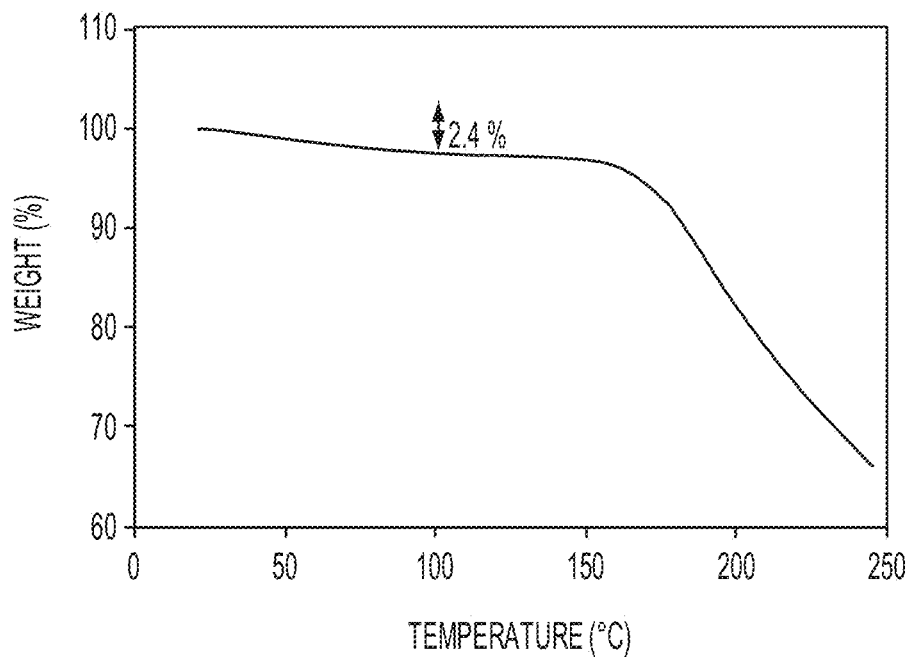
FIG. 43 shows a TGA trace for this form.

In one embodiment, the crystalline tromethamine salt is characterized by the DSC thermogram in FIG. 42. The DSC thermogram showed a melting endotherm with onset and peak temperatures at 107.3° C. and 114.1° C., thus having a melting point within the range of about 114-115° C. In one embodiment, the crystalline tromethamine salt is characterized by the TGA profile in FIG. 43. The TGA profile showed a weight loss of about 2.4%.

Figure 44:
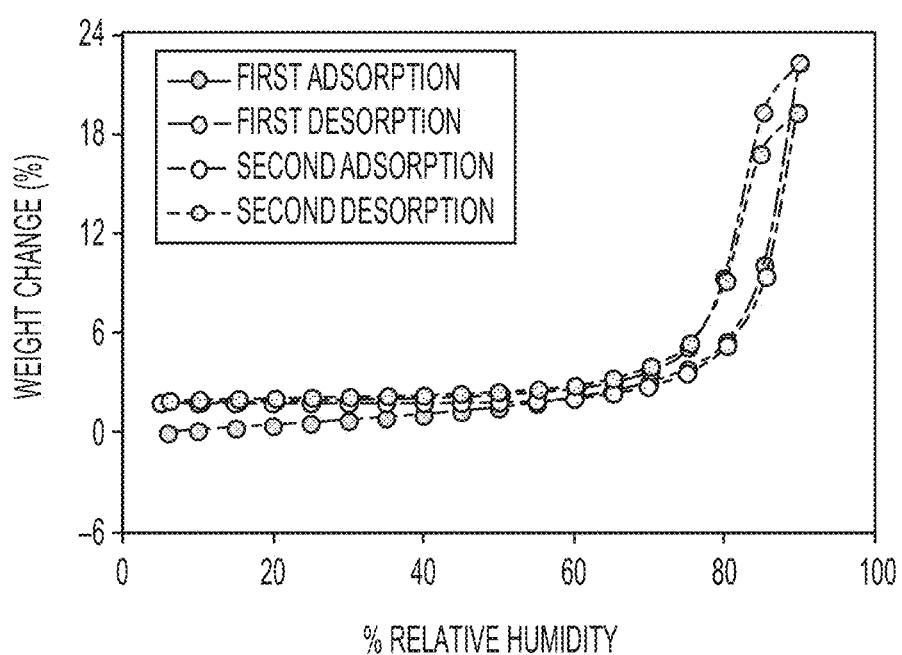
FIG. 44 shows a DMS profile.
Figure 45:
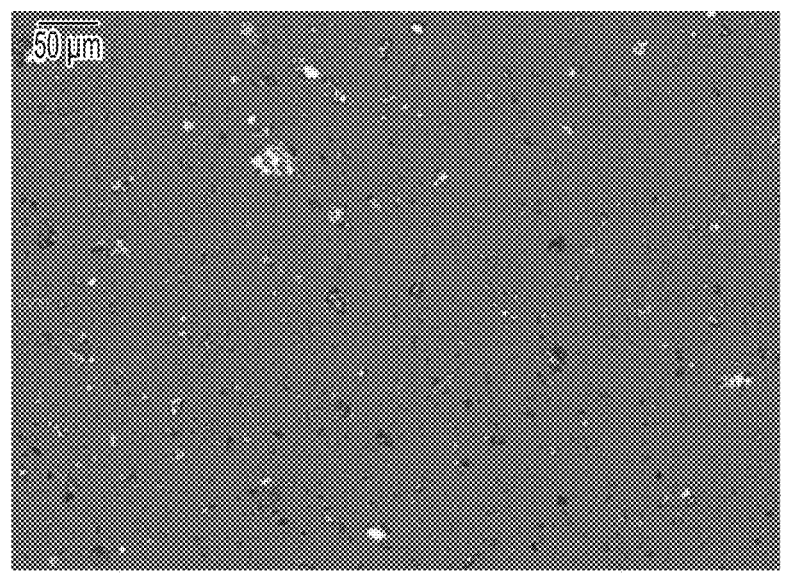
FIG. 45 is a PLM image of this form.

In one embodiment, the crystalline tromethamine salt is characterized by the DMS profile in FIG. 44. In another embodiment, the crystalline tromethamine salt of the invention is characterized by the PLM image in FIG. 45.

Crystalline L-lysine Salt

Figure 46:
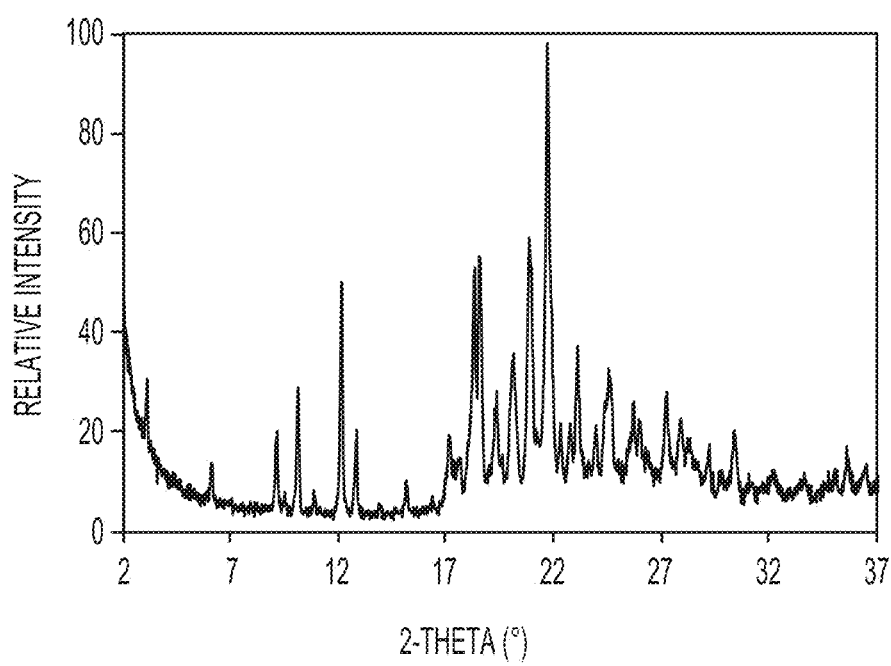
FIG. 46 shows a PXRD pattern of the crystalline L-lysine salt.

The crystalline L-lysine salt is characterized by a PXRD pattern in which the peak positions are substantially in accordance with those shown in FIG. 46. Peaks above 10% relative height are listed in the table below.

| 2θ | d (Å) | Height[1] | H %[2] | * |
|---|---|---|---|---|
| 3.10 | 28.50 | 123 | 24.8 | * |
| 9.13 | 9.67 | 95 | 19.3 | * |
| 10.12 | 8.74 | 149 | 30.2 | * |
| 12.14 | 7.29 | 281 | 56.8 | * |
| 12.84 | 6.89 | 100 | 20.3 | |
| 17.14 | 5.17 | 90 | 18.1 | |
| 17.62 | 5.03 | 63 | 12.7 | |
| 18.33 | 4.84 | 257 | 52.0 | * |
| 18.54 | 4.78 | 268 | 54.2 | * |
| 19.36 | 4.58 | 102 | 20.7 | |
| 20.14 | 4.41 | 151 | 30.5 | * |
| 20.88 | 4.25 | 272 | 55.1 | * |
| 21.72 | 4.09 | 494 | 100.0 | * |
| 22.34 | 3.98 | 55 | 11.2 | |
| 22.78 | 3.90 | 61 | 12.4 | |
| 23.12 | 3.84 | 153 | 30.9 | * |
| 23.98 | 3.71 | 50 | 10.0 | |
| 24.58 | 3.62 | 125 | 25.2 | * |
| 25.74 | 3.46 | 86 | 17.4 | |
| 25.98 | 3.43 | 65 | 13.2 | |
| 27.28 | 3.27 | 90 | 18.3 | |
| 27.94 | 3.19 | 69 | 13.9 | |
| 29.25 | 3.05 | 53 | 10.7 | |
| 30.42 | 2.94 | 77 | 15.5 | |
| 35.64 | 2.52 | 53 | 10.7 | |

[1]Peak height from base line
[2]Percent peak height compared to highest peak
* Indicates peaks that are important to identify this form Thus, in one embodiment, the crystalline L-lysine salt is characterized by a PXRD pattern comprising diffraction peaks at 2θ values of 3.10±0.20, 9.13±0.20, 10.12±0.20, 12.14±0.20, 18.33±0.20, 18.54±0.20, 20.14±0.20, 20.88±0.20, 21.72±0.20, 23.12±0.20, and 24.58±0.20; and further characterized by having one or more additional diffraction peaks at 2θ values selected from 12.84±0.20, 17.14±0.20, 17.62±0.20, 19.36±0.20, 22.34±0.20, 22.78±0.20, 23.98±0.20, 25.74±0.20, 25.98±0.20, 27.28±0.20, 27.94±0.20, 29.25±0.20, 30.42±0.20, and 35.64±0.20.

Figure 47:
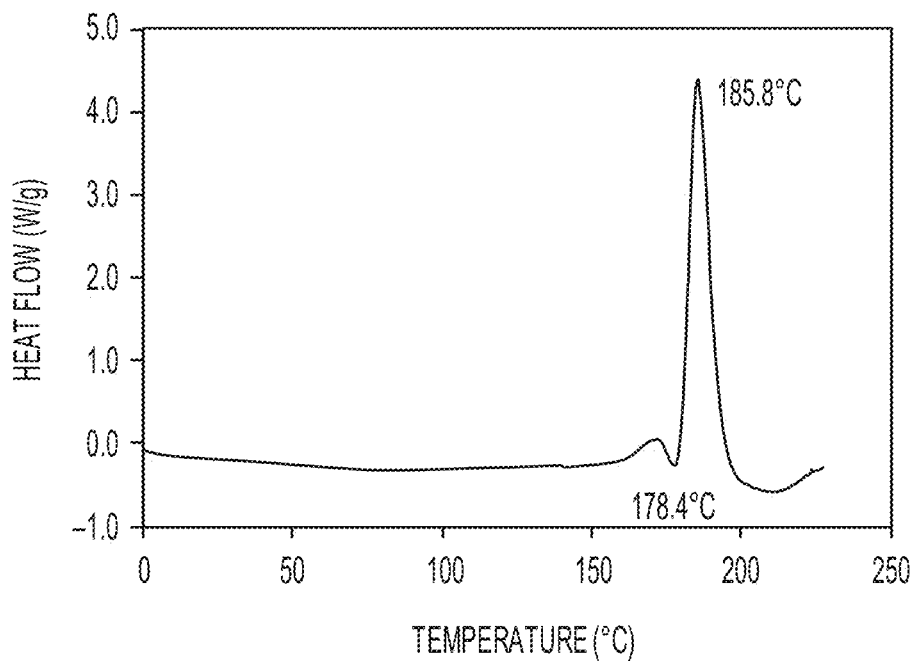
FIG. 47 shows a DSC thermogram.

In one embodiment, the crystalline L-lysine salt is characterized by the DSC thermogram in FIG. 47. The DSC thermogram showed a melting point within the range of about 178-179° C.

Figure 48:
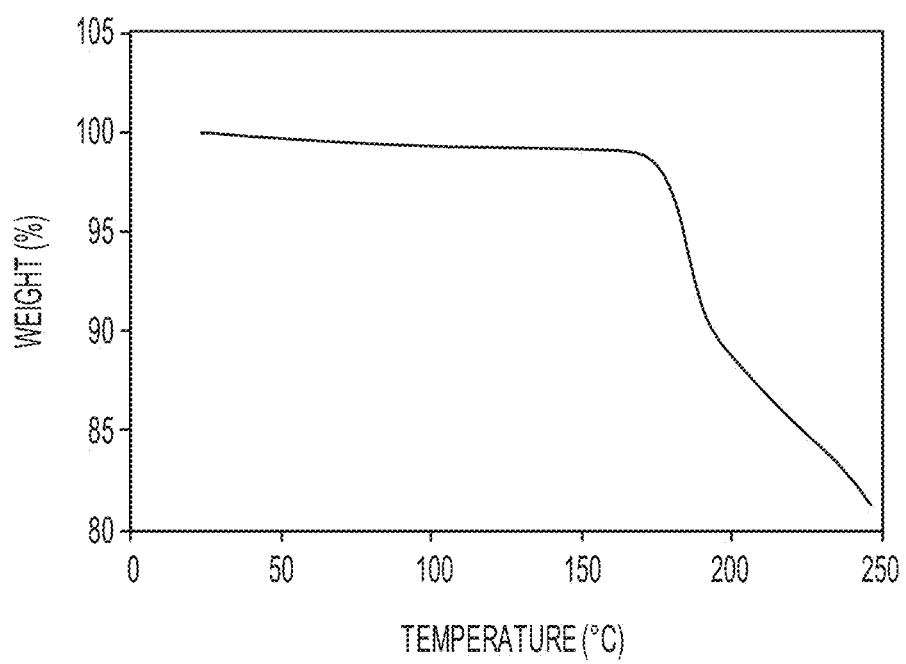
FIG. 48 shows a TGA trace for this form.
Figure 49:
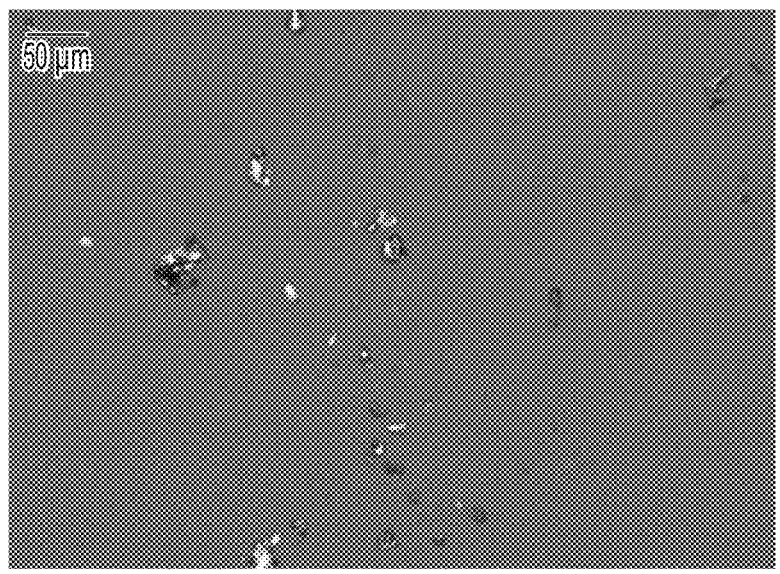
FIG. 49 is a PLM image of this form.

In one embodiment, the crystalline L-lysine salt is characterized by the TGA profile in FIG. 48. In another embodiment, the crystalline L-lysine salt is characterized by the PLM image in FIG. 49.

Crystalline Meglumine Salt

Figure 50:
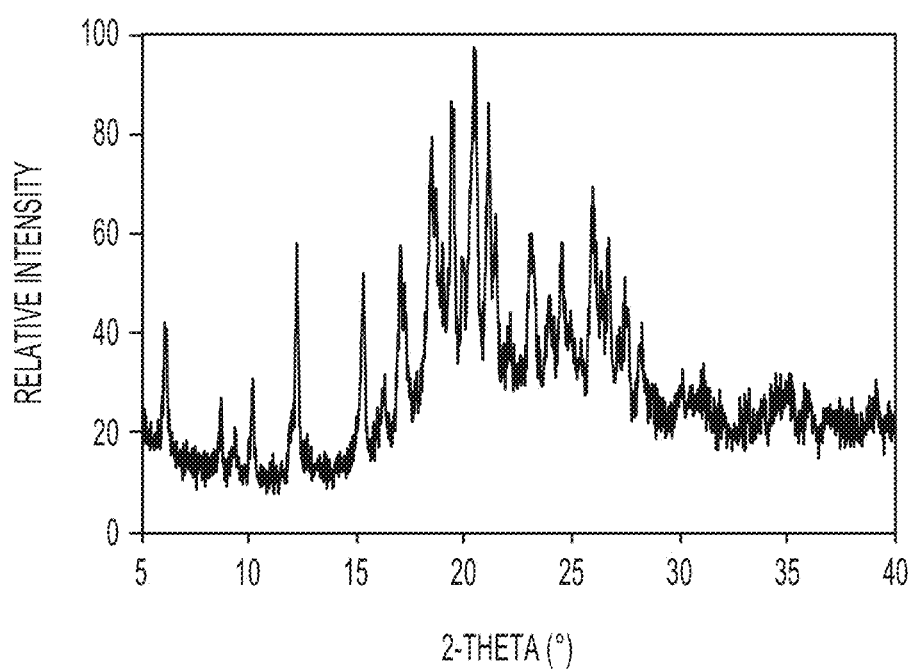
FIG. 50 shows a powder x-ray diffraction (PXRD) pattern of the crystalline meglumine salt.

The crystalline meglumine salt is characterized by a PXRD pattern in which the peak positions are substantially in accordance with those shown in FIG. 50. All peaks are listed in the table below.

| 2θ | d (Å) | Height[1] | H %[2] | * |
|---|---|---|---|---|
| 6.10 | 14.47 | 59.0 | 35.8 | * |
| 8.72 | 10.14 | 34.0 | 20.6 | * |
| 10.20 | 8.67 | 45.0 | 27.4 | * |
| 12.00 | 7.37 | 28.0 | 17.4 | |
| 12.24 | 7.23 | 106.0 | 65.1 | * |
| 15.32 | 5.78 | 82.0 | 50.2 | * |
| 16.31 | 5.43 | 31.0 | 19.2 | |
| 17.04 | 5.20 | 78.0 | 47.6 | * |
| 17.24 | 5.14 | 63.0 | 38.3 | |
| 18.46 | 4.80 | 96.0 | 58.8 | * |
| 18.98 | 4.67 | 52.0 | 31.9 | |
| 19.40 | 4.57 | 105.0 | 64.3 | * |
| 19.89 | 4.46 | 37.0 | 22.8 | |
| 20.46 | 4.34 | 132.0 | 80.6 | * |
| 21.12 | 4.20 | 108.0 | 66.2 | * |
| 21.46 | 4.14 | 62.0 | 37.9 | |
| 23.12 | 3.84 | 65.0 | 39.9 | * |
| 23.96 | 3.71 | 33.0 | 20.3 | |
| 24.52 | 3.63 | 61.0 | 37.4 | |
| 25.96 | 3.43 | 88.0 | 53.8 | * |
| 26.36 | 3.38 | 49.0 | 29.8 | |
| 26.70 | 3.34 | 65.0 | 39.9 | |
| 27.58 | 3.23 | 35.0 | 21.3 | |
| 34.46 | 2.60 | 26.0 | 15.9 | |

[1]Peak height from base line
[2]Percent peak height compared to highest peak
* Indicates peaks that are important to identify this form Thus, in one embodiment, the crystalline meglumine salt is characterized by a PXRD pattern comprising diffraction peaks at 2θ values of 6.10±0.20, 8.72±0.20, 10.20±0.20, 12.24±0.20, 15.32±0.20, 17.04±0.20, 18.46±0.20, 19.40±0.20, 20.46±0.20, 21.12±0.20, 23.12±0.20, and 25.96±0.20; and further characterized by having one or more additional diffraction peaks at 2θ values selected from 12.00±0.20, 16.31±0.20, 17.24±0.20, 18.98±0.20, 19.89±0.20, 21.46±0.20, 23.96±0.20, 24.52±0.20, 26.36±0.20, 26.70±0.20, 27.58±0.20, and 34.46±0.20.

Figure 51:
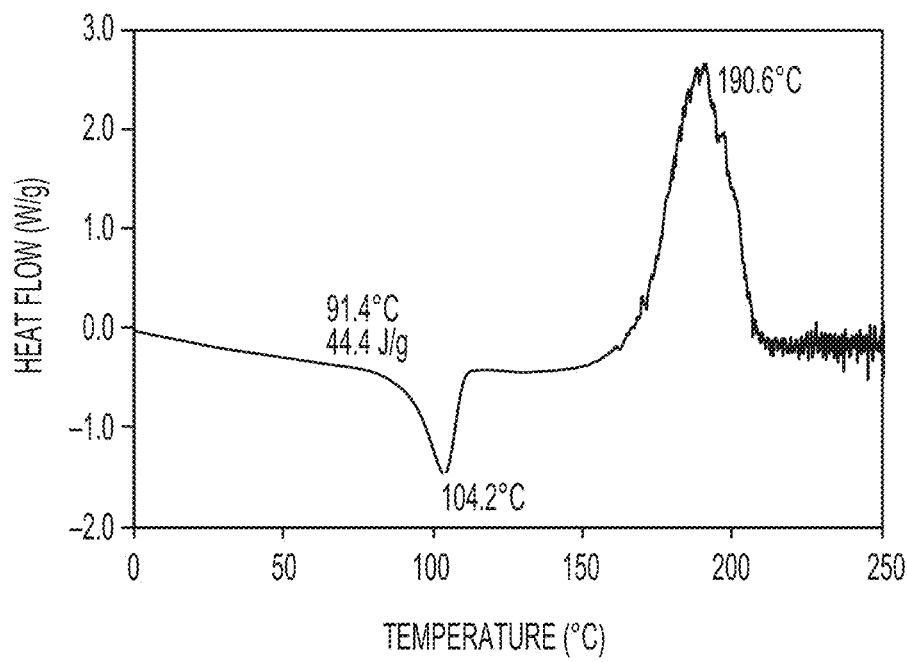
FIG. 51 shows a DSC thermogram.

In one embodiment, the crystalline meglumine salt is characterized by the DSC thermogram in FIG. 51. The DSC thermogram showed a melting endotherm with onset and peak temperatures at 91.4° C. and 104.2° C., thus having a melting point within the range of about 104-105° C.

Figure 52:
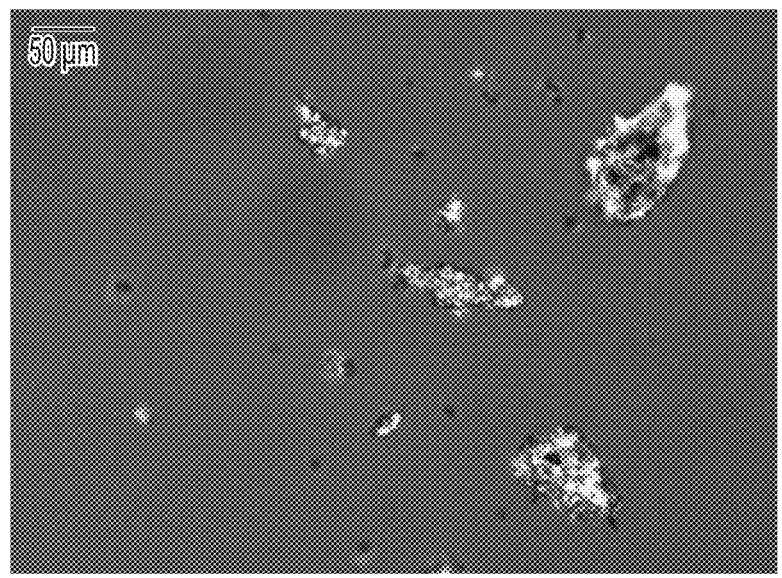
FIG. 52 is a PLM image of this form.

In another embodiment, the crystalline meglumine salt is characterized by the PLM image in FIG. 52.

These properties of the various crystalline compounds of the invention are further illustrated in the Examples below.

Utility (R)-3-[N-(3'-chlorobiphenyl-4-ylmethyl)-N'-(3-hydroxyisoxazole-5-carbonyl)hydrazino]-2-hydroxypropionic acid has activity as a neprilysin inhibitor. Thus, this compound, as well its prodrug, (R)-3-[N-(3'-chlorobiphenyl-4-ylmethyl)-N'-(3-hydroxyisoxazole-5-carbonyl)hydrazino]-2-hydroxypropionic acid isopropyl ester, and crystalline forms thereof, are expected to have therapeutic utility as neprilysin inhibitors. Thus, when discussing the activity of the crystalline compounds of the invention, it is understood that these crystalline prodrugs have the expected activity once metabolized.

Exemplary assays include by way of illustration and not limitation, assays that measure NEP inhibition. Useful secondary assays include assays to measure ACE inhibition and aminopeptidase P (APP) inhibition (e.g., as described in Sulpizio et al. (2005) *JPET* 315:1306-1313). A pharmacodynamic assay to assess the in vivo inhibitory potencies for ACE and NEP in anesthetized rats is described in Seymour et al. (1985) *Hypertension* 7(Suppl I):I-35-1-42 and Wigle et al. (1992) *Can. J. Physiol. Pharmacol.* 70:1525-1528), where ACE inhibition is measured as the percent inhibition of the angiotensin I pressor response and NEP inhibition is measured as increased urinary cyclic guanosine 3',5'-monophosphate (cGMP) output.

There are also many in vivo assays that can be used. The conscious spontaneously hypertensive rat (SHR) model is a renin dependent hypertension model. See for example, Intengan et al. (1999) *Circulation* 100(22):2267-2275 and Badyal et al. (2003) *Indian Journal of Pharmacology* 35:349-362. The conscious desoxycorticosterone acetate-salt (DOCA-salt) rat model is a volume dependent hypertension model that is useful for measuring NEP activity. See for example, Trapani et al. (1989) *J. Cardiovasc. Pharmacol.* 14:419-424, Intengan et al. (1999) *Hypertension* 34(4):907-913, and Badyal et al. (2003) supra). The DOCA-salt model is particularly useful for evaluating the ability of a test compound to reduce blood pressure as well as to measure a test compound's ability to prevent or delay a rise in blood pressure. The Dahl salt-sensive (DSS) hypertensive rat model is a model of hypertension that is sensitive to dietary salt (NaCl), and is described, for example, in Rapp (1982) *Hypertension* 4:753-763. The rat monocrotaline model of pulmonary arterial hypertension described, for example, in Kato et al. (2008) *J. Cardiovasc. Pharmacol.* 51(1):18-23, is a reliable predictor of clinical efficacy for the treatment of pulmonary arterial hypertension. Heart failure animal models include the DSS rat model for heart failure and the aorto-caval fistula model (AV shunt), the latter of which is described, for example, in Norling et al. (1996) *J. Amer. Soc. Nephrol.* 7:1038-1044. Other animal models, such as the hot plate, tail-flick and formalin tests, can be used to measure the analgesic properties of a compound, as well as the spinal nerve ligation (SNL) model of neuropathic pain. See, for example, Malmberg et al. (1999) *Current Protocols in Neuroscience* 8.9.1-8.9.15. Other properties and utilities of the compounds can be demonstrated using various in vitro and in vivo assays well known to those skilled in the art.

The crystalline compounds are expected to be useful for the treatment and/or prevention of medical conditions responsive to NEP inhibition. Thus it is expected that patients suffering from a disease or disorder that is treated by inhibiting the NEP enzyme or by increasing the levels of its peptide substrates, can be treated by administering a therapeutically effective amount of a crystalline compound. For example, by inhibiting NEP, the crystalline compound are expected to potentiate the biological effects of endogenous peptides that are metabolized by NEP, such as the natriuretic peptides, bombesin, bradykinins, calcitonin, endothelins, enkephalins, neurotensin, substance P and vasoactive intestinal peptide. Thus, the crystalline compounds are expected to have other physiological actions, for example, on the renal, central nervous, reproductive and gastrointestinal systems.

Cardiovascular Diseases

By potentiating the effects of vasoactive peptides like the natriuretic peptides and bradykinin, the crystalline compounds are expected to find utility in treating and/or preventing medical conditions such as cardiovascular diseases. See, for example, Rogues et al. (1993) *Pharmacol. Rev.* 45:87-146 and Dempsey et al. (2009)*Amer. J. of Pathology* 174(3):782-796. Cardiovascular diseases of particular interest include hypertension and heart failure. Hypertension includes, by way of illustration and not limitation: primary hypertension, which is also referred to as essential hypertension or idiopathic hypertension; secondary hypertension; hypertension with accompanying renal disease; severe hypertension with or without accompanying renal disease; pulmonary hypertension, including pulmonary arterial hypertension; and resistant hypertension. Heart failure includes, by way of illustration and not limitation: congestive heart failure; acute heart failure; chronic heart failure, for example with reduced left ventricular ejection fraction (also referred to as systolic heart failure) or with preserved left ventricular ejection fraction (also referred to as diastolic heart failure); and acute and chronic decompensated heart failure, with or without accompanying renal disease. Thus, one embodiment of the invention relates to a method for treating hypertension, particularly primary hypertension or pulmonary arterial hypertension, comprising administering to a patient a therapeutically effective amount of a crystalline compound.

For treatment of primary hypertension, the therapeutically effective amount is typically the amount that is sufficient to lower the patient's blood pressure. This would include both mild-to-moderate hypertension and severe hypertension. When used to treat hypertension, the crystalline compounds may be administered in combination with other therapeutic agents such as aldosterone antagonists, angiotensin-converting enzyme inhibitors and dual-acting angiotensin-converting enzyme/neprilysin inhibitors, angiotensin-converting enzyme 2 (ACE2) activators and stimulators, angiotensin-II vaccines, anti-diabetic agents, anti-lipid agents, anti-thrombotic agents, $AT_1$ receptor antagonists and dual-acting $AT_1$ receptor antagonist/neprilysin inhibitors, $\beta_1$-adrenergic receptor antagonists, dual-acting $\beta$-adrenergic receptor antagonist/$\alpha_1$-receptor antagonists, calcium channel blockers, diuretics, endothelin receptor antagonists, endothelin converting enzyme inhibitors, neprilysin inhibitors, natriuretic peptides and their analogs, natriuretic peptide clearance receptor antagonists, nitric oxide donors, non-steroidal anti-inflammatory agents, phosphodiesterase inhibitors (specifically PDE-V inhibitors), prostaglandin receptor agonists, renin inhibitors, soluble guanylate cyclase stimulators and activators, and combinations thereof. In one particular embodiment of the invention, a crystalline compound is combined with an $AT_1$ receptor antagonist, a diuretic, a calcium channel blocker, or a combination thereof, and used to treat primary hypertension. In another particular embodiment of the invention, a crystalline compound is combined with an $AT_1$ receptor antagonist, and used to treat hypertension with accompanying renal disease.

For treatment of pulmonary arterial hypertension, the therapeutically effective amount is typically the amount that is sufficient to lower the pulmonary vascular resistance. Other goals of therapy are to improve a patient's exercise capacity. For example, in a clinical setting, the therapeutically effective amount can be the amount that improves a patient's ability to walk comfortably for a period of 6 minutes (covering a distance of approximately 20-40 meters). When used to treat pulmonary arterial hypertension a crystalline compound may be administered in combination with other therapeutic agents such as $\alpha$-adrenergic antagonists, $\beta_1$-adrenergic receptor antagonists, $\beta_2$-adrenergic receptor agonists, angiotensin-converting enzyme inhibitors, anticoagulants, calcium channel blockers, diuretics, endothelin receptor antagonists, PDE-V inhibitors, prostaglandin analogs, selective serotonin reuptake inhibitors, and combinations thereof. In one particular embodiment of the invention, the crystalline compound is combined with a PDE-V inhibitor or a selective serotonin reuptake inhibitor and used to treat pulmonary arterial hypertension.

Another embodiment of the invention relates to a method for treating heart failure, in particular congestive heart failure (including both systolic and diastolic congestive heart failure), comprising administering to a patient a therapeutically effective amount of the crystalline compound. Typically, the therapeutically effective amount is the amount that is sufficient to lower blood pressure and/or improve renal functions. In a clinical setting, the therapeutically effective amount can be the amount that is sufficient to improve cardiac hemodynamics, like for instance reduction in wedge pressure, right atrial pressure, filling pressure, and vascular resistance. In one embodiment, a crystalline compound is administered as an intravenous dosage form. When used to treat heart failure, a crystalline compound may be administered in combination with other therapeutic agents such as adenosine receptor antagonists, advanced glycation end product breakers, aldosterone antagonists, $AT_1$ receptor antagonists, $\beta_1$-adrenergic receptor antagonists, dual-acting $\beta$-adrenergic receptor antagonist/$\alpha_1$-receptor antagonists, chymase inhibitors, digoxin, diuretics, endothelin converting enzyme (ECE) inhibitors, endothelin receptor antagonists, natriuretic peptides and their analogs, natriuretic peptide clearance receptor antagonists, nitric oxide donors, prostaglandin analogs, PDE-V inhibitors, soluble guanylate cyclase activators and stimulators, and vasopressin receptor antagonists. In one particular embodiment of the invention, a crystalline compound is combined with an aldosterone antagonist, a $\beta_1$-adrenergic receptor antagonist, an $AT_1$ receptor antagonist, or a diuretic, and used to treat congestive heart failure.

Diarrhea

As a NEP inhibitor, the crystalline compounds are expected to inhibit the degradation of endogenous enkephalins and thus may also find utility for the treatment of diarrhea, including infectious and secretory/watery diarrhea. See, for example, Baumer et al. (1992) *Gut* 33:753-758; Farthing (2006) *Digestive Diseases* 24:47-58; and Marçais-Collado (1987) *Eur. J. Pharmacol.* 144(2):125-132. When used to treat diarrhea, a crystalline compound may be combined with one or more additional antidiarrheal treatments.

Renal Diseases

By potentiating the effects of vasoactive peptides like the natriuretic peptides and bradykinin, the crystalline compounds are expected to enhance renal function (see Chen et al. (1999) *Circulation* 100:2443-2448; Lipkin et al. (1997) *Kidney Int.* 52:792-801; and Dussaule et al. (1993) *Clin. Sci.* 84:31-39) and find utility in treating and/or preventing renal diseases. Renal diseases of particular interest include diabetic nephropathy, chronic kidney disease, proteinuria, and particularly acute kidney injury or acute renal failure (see Sharkovska et al. (2011) *Clin. Lab.* 57:507-515 and Newaz et al. (2010) *Renal Failure* 32:384-390). When used to treat renal disease, a crystalline compound may be administered in combination with other therapeutic agents such as angiotensin-converting enzyme inhibitors, $AT_1$ receptor antagonists, and diuretics.

Preventative Therapy

By potentiating the effects of the natriuretic peptides, the crystalline compounds are also expected to be useful in preventative therapy, due to the antihypertrophic and antifibrotic effects of the natriuretic peptides (see Potter et al. (2009) *Handbook of Experimental Pharmacology* 191:341-366), for example in preventing the progression of cardiac insufficiency after myocardial infarction, preventing arterial restenosis after angioplasty, preventing thickening of blood vessel walls after vascular operations, preventing atherosclerosis, and preventing diabetic angiopathy.

Glaucoma

By potentiating the effects of the natriuretic peptides, the crystalline compounds are expected to be useful to treat glaucoma. See, for example, Diestelhorst et al. (1989) *International Ophthalmology* 12:99-101. When used to treat glaucoma, a crystalline compound may be combined with one or more additional anti-glaucoma agents.

Pain Relief

As a NEP inhibitor, the crystalline compounds are expected to inhibit the degradation of endogenous enkephalins and thus such compounds may also find utility as analgesics. See, for example, Rogues et al. (1980) *Nature* 288: 286-288 and Thanawala et al. (2008) *Current Drug Targets* 9:887-894. When used to treat pain, a crystalline compound may be combined with one or more additional antinociceptive drugs such as aminopeptidase N or dipeptidyl peptidase III inhibitors, non-steroidal anti-inflammatory agents, monoamine reuptake inhibitors, muscle relaxants, NMDA receptor antagonists, opioid receptor agonists, 5-$HT_{1D}$ serotonin receptor agonists, and tricyclic antidepressants.

Other Utilities

Due to its NEP inhibition properties, the crystalline compounds are also expected to be useful as an antitussive agent, as well as find utility in the treatment of portal hypertension associated with liver cirrhosis (see Sansoe et al. (2005) *J. Hepatol.* 43:791-798), cancer (see Vesely (2005) *J. Investigative Med.* 53:360-365), depression (see Noble et al. (2007) *Exp. Opin. Ther. Targets* 11:145-159), menstrual disorders, preterm labor, pre-eclampsia, endometriosis, reproductive disorders (for example, male and female infertility, polycystic ovarian syndrome, implantation failure), and male and female sexual dysfunction, including male erectile dysfunction and female sexual arousal disorder. More specifically, the crystalline compounds are expected to be useful in treating female sexual dysfunction (see Pryde et al. (2006) *J. Med. Chem.* 49:4409-4424), which is often defined as a female patient's difficulty or inability to find satisfaction in sexual expression. This covers a variety of diverse female sexual disorders including, by way of illustration and not limitation, hypoactive sexual desire disorder, sexual arousal disorder, orgasmic disorder and sexual pain disorder. When used to treat such disorders, especially female sexual dysfunction, a crystalline compound may be combined with one or more of the following secondary agents: PDE-V inhibitors, dopamine agonists, estrogen receptor agonists and/or antagonists, androgens, and estrogens. Due to its NEP inhibition properties, the crystalline c compounds are also expected to have anti-inflammatory properties, and is expected to have utility as such, particularly when used in combination with statins.

Recent studies suggest that NEP plays a role in regulating nerve function in insulin-deficient diabetes and diet induced obesity (Coppey et al. (2011) *Neuropharmacology* 60:259-266). Therefore, due to its NEP inhibition property, the crystalline compounds are also expected to be useful in providing protection from nerve impairment caused by diabetes or diet induced obesity.

The amount of crystalline compound administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the compound and any secondary agents being administered, and the like. Treatment of a patient suffering from a disease or medical condition (such as hypertension) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating hypertension, blood pressure measurements may be used to determine the effectiveness of treatment. Similar indicators for other diseases and conditions described herein, are well known and are readily available to the treating physician. Continuous monitoring by the physician will insure that the optimal amount of the crystalline compound will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Research Tools

Since the crystalline compounds of the invention are metabolized in vivo to compounds having activity as neprilysin inhibitors, they are also useful as a research tools for investigating or studying biological systems or samples having a NEP enzyme, for example to study diseases where the NEP enzyme or its peptide substrates plays a role. Accordingly, one aspect of the invention relates to a method of using a crystalline compound of the invention as a research tool, comprising conducting a biological assay using a crystalline compound of the invention. Any suitable biological system or sample having a NEP enzyme may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention, NEP enzyme activity in a mammal is inhibited by administering a NEP-inhibiting amount of a crystalline compound of the invention. These crystalline compounds can also be used as research tools by conducting biological assays using such compounds.

When used as a research tool, a biological system or sample comprising a NEP enzyme is typically contacted with a NEP enzyme-inhibiting amount of a crystalline compound.

After the biological system or sample is exposed to the compound, the effects of inhibiting the NEP enzyme are determined using conventional procedures and equipment, such as by measuring receptor binding in a binding assay or measuring ligand-mediated changes in a functional assay. Exposure encompasses contacting cells or tissue with the compound, administering a crystalline compound to a mammal, for example by i.p., p.o., i.v., s.c., or inhaled administration, and so forth. This determining step can involve measuring a response (a quantitative analysis) or can involve making an observation (a qualitative analysis). Measuring a response involves, for example, determining the effects of the crystalline compound on the biological system or sample using conventional procedures and equipment, such as enzyme activity assays and measuring enzyme substrate or product mediated changes in functional assays. The assay results can be used to determine the activity level as well as the amount of crystalline compound necessary to achieve the desired result, that is, a NEP enzyme-inhibiting amount. Typically, the determining step will involve determining the effects of inhibiting the NEP enzyme.

Additionally, the crystalline compounds can be used as research tools for evaluating other chemical compounds, and thus are also useful in screening assays to discover, for example, new compounds having NEP-inhibiting activity. Thus another aspect of the invention relates to a method of evaluating a test compound in a biological assay, comprising: (a) conducting a biological assay with a test compound to provide a first assay value; (b) conducting the biological assay with a crystalline compound of the invention to provide a second assay value; wherein step (a) is conducted either before, after or concurrently with step (b); and (c) comparing the first assay value from step (a) with the second assay value from step (b). Exemplary biological assays include a NEP enzyme inhibition assay. In this manner, the crystalline compounds are used as standards in an assay to allow comparison of the results obtained with a test compound and with the crystalline compound to identify those test compounds that have about equal or superior activity, if any. For example, $pK_i$ data for a test compound or a group of test compounds is compared to the $pK_i$ data for a crystalline compound to identify those test compounds that have the desired properties, for example, test compounds having a $pK_i$ value about equal or superior to the crystalline compound, if any. This aspect of the invention includes, as separate embodiments, both the generation of comparison data (using the appropriate assays) and the analysis of test data to identify test compounds of interest.

Still another aspect of the invention relates to a method of studying a biological system or sample comprising a NEP enzyme, the method comprising: (a) contacting the biological system or sample with a crystalline compound of the invention; and (b) determining the effects caused by the compound on the biological system or sample.

Pharmaceutical Compositions and Formulations

The crystalline compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal), ocular, and parenteral modes of administration. However, it will be understood by those skilled in the art that, once a crystalline compound has been formulated, it may no longer be in crystalline form, i.e., it may be dissolved in a suitable carrier. Further, the crystalline compounds may be administered, for example orally, in multiple doses per day (for example, two, three, or four times daily), in a single daily dose or a single weekly dose.

Accordingly, in one embodiment, the invention relates to a pharmaceutical composition comprising a pharmaceutically acceptable carrier and a crystalline compound. The compositions may contain other therapeutic and/or formulating agents if desired. When discussing compositions, a "crystalline compound of the invention" may also be referred to herein as the "active agent," to distinguish it from other components of the formulation, such as the carrier.

The pharmaceutical compositions of the invention typically contain a therapeutically effective amount of a crystalline compound. Those skilled in the art will recognize, however, that a pharmaceutical composition may contain more than a therapeutically effective amount, such as in bulk compositions, or less than a therapeutically effective amount, that is, individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent.

Any conventional carrier or excipient may be used in the pharmaceutical composition. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in *Remington: The Science and Practice of Pharmacy*, 20$^{th}$ Edition, Lippincott Williams & White, Baltimore, Md. (2000); and H. C. Ansel et al., *Pharmaceutical Dosage Forms and Drug Delivery Systems*, 7$^{th}$ Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

In one embodiment, the pharmaceutical compositions are suitable for oral administration. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (capsules, tablets, pills and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in microencapsulated form, optionally with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (for example, cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, that is, each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's air-stream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, glycerin, and sodium lauryl sulfate. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

The crystalline compounds can also be administered parenterally (for example, by subcutaneous, intravenous, intramuscular, or intraperitoneal injection). For such administration, the active agent is provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. Parenteral formulations may also contain one or more anti-oxidants, solubilizers, stabilizers, preservatives, wetting agents, emulsifiers, and dispersing agents. Surfactants, additional stabilizing agents or pH-adjusting agents (acids, bases or buffers) and anti-oxidants are particularly useful to provide stability to the formulation, for example, to minimize or avoid hydrolysis of ester and amide linkages, or dimerization of thiols that may be present in the compound. These formulations may be rendered sterile by use of a sterile injectable medium, a sterilizing agent, filtration, irradiation, or heat. In one particular embodiment, the parenteral formulation comprises an aqueous cyclodextrin solution as the pharmaceutically acceptable carrier. Suitable cyclodextrins include cyclic molecules containing six or more α-D-glucopyranose units linked at the 1,4 positions by a linkages as in amylase, β-cyclodextrin or cycloheptaamylose. Exemplary cyclodextrins include cyclodextrin derivatives such as hydroxypropyl and sulfobutyl ether cyclodextrins such as hydroxypropyl-β-cyclodextrin and sulfobutyl ether β-cyclodextrin. Exemplary buffers for such formulations include carboxylic acid-based buffers such as citrate, lactate and maleate buffer solutions.

The crystalline compounds can also be administered transdermally using known transdermal delivery systems and excipients. For example, the compound can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

Secondary Agents

The crystalline compounds of the invention may be useful as the sole treatment of a disease or may be combined with one or more other therapeutic agents in order to obtain the desired therapeutic effect. Thus, in one embodiment, pharmaceutical compositions of the invention contain other drugs that are co-administered with a crystalline compound. For example, the composition may further comprise one or more drugs (also referred to as "secondary agents(s)"). Such therapeutic agents are well known in the art, and include adenosine receptor antagonists, α-adrenergic receptor antagonists, $β_1$-adrenergic receptor antagonists, $β_2$-adrenergic receptor agonists, dual-acting β-adrenergic receptor antagonist/$α_1$-receptor antagonists, advanced glycation end product breakers, aldosterone antagonists, aldosterone synthase inhibitors, aminopeptidase N inhibitors, androgens, angiotensin-converting enzyme inhibitors and dual-acting angiotensin-converting enzyme/neprilysin inhibitors, angiotensin-converting enzyme 2 activators and stimulators, angiotensin-II vaccines, anticoagulants, anti-diabetic agents, antidiarrheal agents, anti-glaucoma agents, anti-lipid agents, antinociceptive agents, anti-thrombotic agents, $AT_1$ receptor antagonists and dual-acting $AT_1$ receptor antagonist/neprilysin inhibitors and multifunctional angiotensin receptor blockers, bradykinin receptor antagonists, calcium channel blockers, chymase inhibitors, digoxin, diuretics, dopamine agonists, endothelin converting enzyme inhibitors, endothelin receptor antagonists, HMG-CoA reductase inhibitors, estrogens, estrogen receptor agonists and/or antagonists, monoamine reuptake inhibitors, muscle relaxants, natriuretic peptides and their analogs, natriuretic peptide clearance receptor antagonists, neprilysin inhibitors, nitric oxide donors, non-steroidal anti-inflammatory agents, N-methyl d-aspartate receptor antagonists, opioid receptor agonists, phosphodiesterase inhibitors, prostaglandin analogs, prostaglandin receptor agonists, renin inhibitors, selective serotonin reuptake inhibitors, sodium channel blocker, soluble guanylate cyclase stimulators and activators, tricyclic antidepressants, vasopressin receptor antagonists, and combinations thereof. Specific examples of these agents are detailed herein.

Accordingly, in yet another aspect of the invention, a pharmaceutical composition comprises the crystalline compound, a second active agent, and a pharmaceutically acceptable carrier. Third, fourth etc. active agents may also be included in the composition. In combination therapy, the amount of the crystalline compound that is administered, as well as the amount of secondary agents, may be less than the amount typically administered in monotherapy.

The crystalline compounds may be physically mixed with the second active agent to form a composition containing both agents; or each agent may be present in separate and distinct compositions which are administered to the patient simultaneously or at separate times. For example, a crystalline compound can be combined with a second active agent using conventional procedures and equipment to form a combination of active agents comprising a crystalline compound and a second active agent. Additionally, the active agents may be combined with a pharmaceutically acceptable carrier to form a pharmaceutical composition comprising a crystalline compound, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of the crystalline compound, ranging anywhere from concurrent with administration of the crystalline compound to about 24 hours post-dose. This is also referred to as sequential administration. Thus, the crystalline compound can be orally administered simultaneously or sequentially with another active agent using two tablets, with one tablet for each active agent, where sequential may mean being administered immediately after administration of t the crystalline compound or at some predetermined time later (for example, one hour later or three hours later). It is also contemplated that the secondary agent may be administered more than 24 hours after administration of the crystalline compound. Alternatively, the combination may be administered by different routes of administration, that is, one orally and the other by inhalation.

In one embodiment, the kit comprises a first dosage form comprising the crystalline compound and at least one additional dosage form comprising one or more of the secondary agents set forth herein, in quantities sufficient to carry out the methods of the invention. The first dosage form and the second (or third, etc.) dosage form together comprise a therapeutically effective amount of active agents for the treatment or prevention of a disease or medical condition in a patient.

Secondary agent(s), when included, are present in a therapeutically effective amount such that they are typically administered in an amount that produces a therapeutically beneficial effect when co-administered with a crystalline compound. The secondary agent can be in the form of a pharmaceutically acceptable salt, solvate, optically pure stereoisomer, and so forth. The secondary agent may also be in the form of a prodrug, for example, a compound having a carboxylic acid group that has been esterified. Thus, secondary agents listed herein are intended to include all such forms, and are commercially available or can be prepared using conventional procedures and reagents.

In one embodiment, the crystalline compounds are administered in combination with an adenosine receptor antagonist, representative examples of which include, but are not limited to, naxifylline, rolofylline, SLV-320, theophylline, and tonapofylline.

In one embodiment, the crystalline compounds are administered in combination with an α-adrenergic receptor antagonist, representative examples of which include, but are not limited to, doxazosin, prazosin, tamsulosin, and terazosin.

The crystalline compounds may also be administered in combination with a $\beta_1$-adrenergic receptor antagonist ("$\beta_1$-blockers"). Representative $\beta_1$-blockers include, but are not limited to, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, bubridine, butofilolol, carazolol, carteolol, carvedilol, celiprolol, cetamolol, cloranolol, dilevalol, epanolol, esmolol, indenolol, labetolol, levobunolol, mepindolol, metipranolol, metoprolol such as metoprolol succinate and metoprolol tartrate, moprolol, nadolol, nadoxolol, nebivalol, nipradilol, oxprenolol, penbutolol, perbutolol, pindolol, practolol, pronethalol, propranolol, sotalol, sufinalol, talindol, tertatolol, tilisolol, timolol, toliprolol, xibenolol, and combinations thereof. In one particular embodiment, the $\beta_1$-antagonist is selected from atenolol, bisoprolol, metoprolol, propranolol, sotalol, and combinations thereof. Typically, the $\beta_1$-blocker will be administered in an amount sufficient to provide from about 2-900 mg per dose.

In one embodiment, the crystalline compounds are administered in combination with a $\beta_2$-adrenergic receptor agonist, representative examples of which include, but are not limited to, albuterol, bitolterol, fenoterol, formoterol, indacaterol, isoetharine, levalbuterol, metaproterenol, pirbuterol, salbutamol, salmefamol, salmeterol, terbutaline, vilanterol, and the like Typically, the $\beta_2$-adrenergic receptor agonist will be administered in an amount sufficient to provide from about 0.05-500 µg per dose.

In one embodiment, the crystalline compounds are administered in combination with an advanced glycation end product (AGE) breaker, examples of which include, by way of illustration and not limitation, alagebrium (or ALT-711), and TRC4149.

In another embodiment, the crystalline compounds are administered in combination with an aldosterone antagonist, representative examples of which include, but are not limited to, eplerenone, spironolactone, and combinations thereof. Typically, the aldosterone antagonist will be administered in an amount sufficient to provide from about 5-300 mg per day.

In one embodiment, the crystalline compounds are administered in combination with an aminopeptidase N or dipeptidyl peptidase III inhibitor, examples of which include, by way of illustration and not limitation, bestatin and PC18 (2-amino-4-methylsulfonyl butane thiol, methionine thiol).

The crystalline compounds can also be administered in combination with an angiotensin-converting enzyme (ACE) inhibitor. Representative ACE inhibitors include, but are not limited to, accupril, alacepril, benazepril, benazeprilat, captopril, ceranapril, cilazapril, delapril, enalapril, enalaprilat, fosinopril, fosinoprilat, imidapril, lisinopril, moexipril, monopril, moveltopril, pentopril, perindopril, quinapril, quinaprilat, ramipril, ramiprilat, saralasin acetate, spirapril, temocapril, trandolapril, zofenopril, and combinations thereof. In a particular embodiment, the ACE inhibitor is selected from: benazepril, captopril, enalapril, lisinopril, ramipril, and combinations thereof. Typically, the ACE inhibitor will be administered in an amount sufficient to provide from about 1-150 mg per day.

In one embodiment, the crystalline compounds are administered in combination with a dual-acting agent, such as an angiotensin-converting enzyme/neprilysin (ACE/NEP) inhibitor, examples of which include, but are not limited to: AVE-0848 ((4S,7S,12bR)-7-[3-methyl-2(S)-sulfanylbutyramido]-6-oxo-1,2,3,4,6,7,8,12b-octahydropyrido[2,1-a][2]-benzazepine-4-carboxylic acid); AVE-7688 (ilepatril) and its parent compound; BMS-182657 (2-[2-oxo-3 (S)-[3-phenyl-2 (S)-sulfanylpropionamido]-2,3,4,5-tetrahydro-1H-1-benzazepin-1-yl]acetic acid); CGS-35601 (N-[1-[4-methyl-2(S)-sulfanylpentanamido]cyclopentylcarbonyl]-L-tryptophan); fasidotril; fasidotrilate; enalaprilat; ER-32935 ((3R,6S,9aR)-6-[3(S)-methyl-2(S)-sulfanylpentanamido]-5-oxoperhydrothiazolo[3,2-a]azepine-3-carboxylic acid); gempatrilat; MDL-101264 ((4S,7S,12bR)-7-[2(S)-(2-morpholinoacetylthio)-3-phenylpropionamido]-6-oxo-1,2,3,4,6,7,8,12b-octahydropyrido[2,1-a][2]benzazepine-4-carboxylic acid); MDL-101287 ([4S-[4α,7α(R*), 12bβ]]-7-[2-(carboxymethyl)-3-phenylpropionamido]-6-oxo-1,2,3,4,6,7,8,12b-octahydropyrido[2,1-a][2]benzazepine-4-carboxylic acid); omapatrilat; RB-105 (N-[2(5)-(mercaptomethyl)-3 (R)-phenylbutyl]-L-alanine); sampatrilat; SA-898 ((2R, 4R)—N-[2-(2-hydroxyphenyl)-3-(3-mercaptopropionyl) thiazolidin-4-ylcarbonyl]-L-phenylalanine); Sch-50690 (N-[1(S)-carboxy-2-[N2-(methanesulfonyl)-L-lysylamino] ethyl]-L-valyl-L-tyrosine); and combinations thereof, may also be included. In one particular embodiment, the ACE/NEP inhibitor is selected from: AVE-7688, enalaprilat, fasidotril, fasidotrilate, omapatrilat, sampatrilat, and combinations thereof.

In one embodiment, the crystalline compounds are administered in combination with an angiotensin-converting enzyme 2 (ACE2) activator or stimulator.

In one embodiment, the crystalline compounds are administered in combination with an angiotensin-II vaccine, examples of which include, but are not limited to ATR12181 and CYT006-AngQb.

In one embodiment, the crystalline compounds are administered in combination with an anticoagulant, representative examples of which include, but are not limited to: coumarins such as warfarin; heparin; and direct thrombin inhibitors such as argatroban, bivalirudin, dabigatran, and lepirudin.

In yet another embodiment, the crystalline compounds are administered in combination with an anti-diabetic agent. Representative anti-diabetic agents include injectable drugs as well as orally effective drugs, and combinations thereof. Examples of injectable drugs include, but are not limited to, insulin and insulin derivatives. Examples of orally effective drugs include, but are not limited to: biguanides such as metformin; glucagon antagonists; α-glucosidase inhibitors such as acarbose and miglitol; dipeptidyl peptidase IV inhibitors (DPP-IV inhibitors) such as alogliptin, denagliptin, linagliptin, saxagliptin, sitagliptin, and vildagliptin; meglitinides such as repaglinide; oxadiazolidinediones; sulfonylureas such as chlorpropamide, glimepiride, glipizide, glyburide, and tolazamide; thiazolidinediones such as pioglitazone and rosiglitazone; and combinations thereof.

In another embodiment, the crystalline compounds are administered in combination with antidiarrheal treatments. Representative treatment options include, but are not limited to, oral rehydration solutions (ORS), loperamide, diphenoxylate, and bismuth sabsalicylate.

In yet another embodiment, the crystalline compounds are administered in combination with an anti-glaucoma agent. Representative anti-glaucoma agents include, but are not limited to: α-adrenergic agonists such as brimonidine; $β_1$-adrenergic receptor antagonists; topical $β_1$-blockers such as betaxolol, levobunolol, and timolol; carbonic anhydrase inhibitors such as acetazolamide, brinzolamide, or dorzolamide; cholinergic agonists such as cevimeline and DMXB-anabaseine; epinephrine compounds; miotics such as pilocarpine; and prostaglandin analogs.

In yet another embodiment, the crystalline compounds are administered in combination with an anti-lipid agent. Representative anti-lipid agents include, but are not limited to: cholesteryl ester transfer protein inhibitors (CETPs) such as anacetrapib, dalcetrapib, and torcetrapib; statins such as atorvastatin, fluvastatin, lovastatin, pravastatin, rosuvastatin and simvastatin; and combinations thereof.

In one embodiment, the crystalline compounds are administered in combination with an anti-thrombotic agent. Representative anti-thrombotic agents include, but are not limited to: aspirin; anti-platelet agents such as clopidogrel, prasugrel, and ticlopidine; heparin, and combinations thereof.

In one embodiment, the crystalline compounds are administered in combination with an $AT_1$ receptor antagonist, also known as angiotensin II type 1 receptor blockers (ARBs). Representative ARBs include, but are not limited to, abitesartan, azilsartan (e.g., azilsartan medoxomil), benzyllosartan, candesartan, candesartan cilexetil, elisartan, embusartan, enoltasosartan, eprosartan, EXP3174, fonsartan, forasartan, glycyllosartan, irbesartan, isoteoline, losartan, medoximil, milfasartan, olmesartan (e.g., olmesartan medoxomil), opomisartan, pratosartan, ripisartan, saprisartan, saralasin, sarmesin, TAK-591, tasosartan, telmisartan, valsartan, zolasartan, and combinations thereof. In a particular embodiment, the ARB is selected from azilsartan medoxomil, candesartan cilexetil, eprosartan, irbesartan, losartan, olmesartan medoxomil, irbesartan, saprisartan, tasosartan, telmisartan, valsartan, and combinations thereof. Exemplary salts and/or prodrugs include candesartan cilexetil, eprosartan mesylate, losartan potassium salt, and olmesartan medoxomil. Typically, the ARB will be administered in an amount sufficient to provide from about 4-600 mg per dose, with exemplary daily dosages ranging from 20-320 mg per day.

The crystalline compounds may also be administered in combination with a dual-acting agent, such as an $AT_1$ receptor antagonist/neprilysin inhibitor (ARB/NEP) inhibitor, examples of which include, but are not limited to, compounds described in U.S. Publication Nos. 2008/0269305 and 2009/0023228, both to Allegretti et al. filed on Apr. 23, 2008, such as the compound, 4'-{2-ethoxy-4-ethyl-5-[(S)-2-mercapto-4-methylpentanoylamino)methyl]imidazol-1-ylmethyl}-3'-fluorobiphenyl-2-carboxylic acid.

The crystalline compounds may also be administered in combination with multifunctional angiotensin receptor blockers as described in Kurtz & Klein (2009) *Hypertension Research* 32:826-834.

In one embodiment, the crystalline compounds are administered in combination with a bradykinin receptor antagonist, for example, icatibant (HOE-140). It is expected that this combination therapy may present the advantage of preventing angioedema or other unwanted consequences of elevated bradykinin levels.

In one embodiment, the crystalline compounds are administered in combination with a calcium channel blocker. Representative calcium channel blockers include, but are not limited to, amlodipine, anipamil, aranipine, barnidipine, bencyclane, benidipine, bepridil, clentiazem, cilnidipine, cinnarizine, diltiazem, efonidipine, elgodipine, etafenone, felodipine, fendiline, flunarizine, gallopamil, isradipine, lacidipine, lercanidipine, lidoflazine, lomerizine, manidipine, mibefradil, nicardipine, nifedipine, niguldipine, niludipine, nilvadipine, nimodipine, nisoldipine, nitrendipine, nivaldipine, perhexyline, prenylamine, ryosidine, semotiadil, terodiline, tiapamil, verapamil, and combinations thereof. In a particular embodiment, the calcium channel blocker is selected from amlodipine, bepridil, diltiazem, felodipine, isradipine, lacidipine, nicardipine, nifedipine, niguldipine, niludipine, nimodipine, nisoldipine, ryosidine, verapamil, and combinations thereof. Typically, the calcium channel blocker will be administered in an amount sufficient to provide from about 2-500 mg per dose.

In one embodiment, the crystalline compounds are administered in combination with a chymase inhibitor, such as TPC-806 and 2-(5-formylamino-6-oxo-2-phenyl-1,6-dihydropyrimidine-1-yl)-N-[{3,4-di oxo-1-phenyl-7-(2-pyridyloxy)}-2-heptyl]acetamide (NK3201).

In one embodiment, the crystalline compounds are administered in combination with a diuretic. Representative diuretics include, but are not limited to: carbonic anhydrase inhibitors such as acetazolamide and dichlorphenamide; loop diuretics, which include sulfonamide derivatives such as acetazolamide, ambuside, azosernide, bumetanide, butazolamide, chloraminophenamide, clofenamide, clopamide, clorexolone, disulfamide, ethoxolamide, furosemide, mefruside, methazolamide, piretanide, torsemide, tripamide, and xipamide, as well as non-sulfonamide diuretics such as ethacrynic acid and other phenoxyacetic acid compounds such as tienilic acid, indacrinone and quincarbate; osmotic diuretics such as mannitol; potassium-sparing diuretics, which include aldosterone antagonists such as spironolactone, and $Na^+$ channel inhibitors such as amiloride and triamterene; thiazide and thiazide-like diuretics such as althiazide, bendroflumethiazide, benzylhydrochlorothiazide, benzthiazide, buthiazide, chlorthalidone, chlorothiazide, cyclopenthiazide, cyclothiazide, epithiazide, ethiazide, fenquizone, flumethiazide, hydrochlorothiazide, hydroflumethiazide, indapamide, methylclothiazide, meticrane, metolazone, paraflutizide, polythiazide, quinethazone, teclothiazide, and trichloromethiazide; and combinations thereof. In a particular embodiment, the diuretic is selected from amiloride, bumetanide, chlorothiazide, chlorthalidone, dichlorphenamide, ethacrynic acid, furosemide, hydrochlorothiazide, hydroflumethiazide, indapamide, methylclothiazide, metolazone, torsemide, triamterene, and combinations thereof. The diuretic will be administered in an amount sufficient to provide from about 5-50 mg per day, more typically 6-25 mg per day, with common dosages being 6.25 mg, 12.5 mg or 25 mg per day.

The crystalline compounds may also be administered in combination with an endothelin converting enzyme (ECE) inhibitor, examples of which include, but are not limited to, phosphoramidon, CGS 26303, and combinations thereof.

In a particular embodiment, the crystalline compounds are administered in combination with an endothelin receptor antagonist. Representative endothelin receptor antagonists include, but are not limited to: selective endothelin receptor antagonists that affect endothelin A receptors, such as avosentan, ambrisentan, atrasentan, BQ-123, clazosentan, darusentan, sitaxentan, and zibotentan; and dual endothelin receptor antagonists that affect both endothelin A and B receptors, such as bosentan, macitentan, tezosentan).

In yet another embodiment, the crystalline compounds are administered in combination with one or more HMG-CoA reductase inhibitors, which are also known as statins. Representative statins include, but are not limited to, atorvastatin, fluvastatin, lovastatin, pitavastatin, pravastatin, rosuvastatin and simvastatin.

In one embodiment, the crystalline compounds are administered in combination with a monoamine reuptake inhibitor, examples of which include, by way of illustration and not limitation, norepinephrine reuptake inhibitors such as atomoxetine, buprorion and the buprorion metabolite hydroxy-buprorion, maprotiline, reboxetine, and viloxazine; selective serotonin reuptake inhibitors (SSRIs) such as citalopram and the citalopram metabolite desmethylcitalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline; dual serotonin-norepinephrine reuptake inhibitors (SNRIs) such as bicifadine, duloxetine, milnacipran, nefazodone, and venlafaxine; and combinations thereof.

In another embodiment, the crystalline compounds are administered in combination with a muscle relaxant, examples of which include, but are not limited to: carisoprodol, chlorzoxazone, cyclobenzaprine, diflunisal, metaxalone, methocarbamol, and combinations thereof.

In one embodiment, the crystalline compounds are administered in combination with a natriuretic peptide or analog, examples of which include but are not limited to: carperitide, CD-NP (Nile Therapeutics), CU-NP, nesiritide, PL-3994 (Palatin Technologies, Inc.), ularitide, cenderitide, and compounds described in Ogawa et al (2004) *J. Biol. Chem.* 279: 28625-31. These compounds are also referred to as natriuretic peptide receptor-A (NPR-A) agonists. In another embodiment, the crystalline compound is administered in combination with a natriuretic peptide clearance receptor (NPR-C) antagonist such as SC-46542, cANF (4-23), and AP-811 (Veale (2000) *Bioorg. Med. Chem. Lett.* 10:1949-52). For example, AP-811 has shown synergy when combined with the NEP inhibitor, thiorphan (Wegner (1995) *Clin. Exper. Hypert.* 17:861-876).

In another embodiment, the crystalline compounds are administered in combination with another neprilysin (NEP) inhibitor. Representative NEP inhibitors include, but are not limited to: AHU-377; candoxatril; candoxatrilat; dexecadotril ((+)-N-[2(R)-(acetylthiomethyl)-3-phenylpropionyl]glycine benzyl ester); CGS-24128 (3-[3-(biphenyl-4-yl)-2-(phosphonomethylamino)propionamido]propionic acid); CGS-24592 ((S)-3-[3-(biphenyl-4-yl)-2-(phosphonomethylamino)propionamido]propionic acid); CGS-25155 (N-[9(R)-(acetylthiomethyl)-10-oxo-1-azacyclodecan-2(S)-ylcarbonyl]-4(R)-hydroxy-L-proline benzyl ester); 3-(1-carbamoylcyclohexyl)propionic acid derivatives described in WO 2006/027680 to Hepworth et al. (Pfizer Inc.); JMV-390-1 (2(R)-benzyl-3-(N-hydroxycarbamoyl)propionyl-L-isoleucyl-L-leucine); ecadotril; phosphoramidon; retrothiorphan; RU-42827 (2-(mercaptomethyl)-N-(4-pyridinyl)benzenepropionamide); RU-44004 (N-(4-morpholinyl)-3-phenyl-2-(sulfanylmethyl)propionamide); SCH-32615 ((S)—N—[N-(1-carboxy-2-phenylethyl)-L-phenylalanyl]-β-alanine) and its prodrug SCH-34826 ((S)—N—[N-[1-[[(2,2-dimethyl-1,3-dioxolan-4-yl)methoxy]carbonyl]-2-phenylethyl]-L-phenylalanyl]-β-alanine); sialorphin; SCH-42495 (N-[2(S)-(acetylsulfanylmethyl)-3-(2-methylphenyl)propionyl]-L-methionine ethyl ester); spinorphin; SQ-28132 (N-[2-(mercaptomethyl)-1-oxo-3-phenylpropyl]leucine); SQ-28603 (N-[2-(mercaptomethyl)-1-oxo-3-phenylpropyl]-β-alanine); SQ-29072 (7-[[2-(mercaptomethyl)-1-oxo-3-phenylpropyl]amino]heptanoic acid); thiorphan and its prodrug racecadotril; UK-69578 (cis-4-[[[1-[2-carboxy-3-(2-methoxyethoxy)propyl]cyclopentyl]carbonyl]amino]cyclohexanecarboxylic acid); UK-447,841 (2-{1-[3-(4-chlorophenyl)propylcarbamoyl]-cyclopentylmethyl}-4-methoxybutyric acid); UK-505,749 ((R)-2-methyl-3-{1-[3-(2-methylbenzothiazol-6-yl)propylcarbamoyl]cyclopentyl}propionic acid); 5-biphenyl-4-yl-4-(3-carboxypropionylamino)-2-methylpentanoic acid and 5-biphenyl-4-yl-4-(3-carboxypropionylamino)-2-methylpentanoic acid ethyl ester (WO 2007/056546); daglutril [(3S, 2'R)-3-{1-[2'-(ethoxycarbonyl)-4'-phenylbutyl]-cyclopentan-1-carbonylamino}-2,3,4,5-tetrahydro-2-oxo-1H-1-benzazepine-1-acetic acid] described in WO 2007/106708 to Khder et al. (Novartis AG); and combinations thereof. In a particular embodiment, the NEP inhibitor is selected from AHU-377, candoxatril, candoxatrilat, CGS-24128, phosphoramidon, SCH-32615, SCH-34826, SQ-28603, thiorphan, and combinations thereof. In a particular embodiment, the NEP inhibitor is a compound such as daglutril or CGS-26303 ([N-[2-(biphenyl-4-yl)-1(S)-(1H-tetrazol-5-yl)ethyl]amino]methylphosphonic acid), which have activity both as inhibitors of the endothelin converting enzyme (ECE) and of NEP. Other dual acting ECE/NEP compounds can also be used. The NEP inhibitor will be administered in an amount sufficient to provide from about 20-800 mg per day, with typical daily dosages ranging from 50-700 mg per day, more commonly 100-600 or 100-300 mg per day.

In one embodiment, the crystalline compounds are administered in combination with a nitric oxide donor, examples of which include, but are not limited to nicorandil; organic nitrates such as pentaerythritol tetranitrate; and sydnonimines such as linsidomine and molsidomine.

In yet another embodiment, the crystalline compounds are administered in combination with a non-steroidal anti-inflammatory agent (NSAID). Representative NSAIDs include, but are not limited to: acemetacin, acetyl salicylic acid, alclofenac, alminoprofen, amfenac, amiprilose, amoxiprin, anirolac, apazone, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lornoxicam, meclofenamate, meclofenamic acid, mefenamic acid, meloxicam, mesalamine, miroprofen, mofebutazone, nabumetone, naproxen, niflumic acid, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof.

In one embodiment, the crystalline compounds are administered in combination with an N-methyl d-aspartate (NMDA) receptor antagonist, examples of which include, by way of illustration and not limitation, including amantadine, dextromethorphan, dextropropoxyphene, ketamine, ketobemidone, memantine, methadone, and so forth.

In still another embodiment, the crystalline compounds are administered in combination with an opioid receptor agonist (also referred to as opioid analgesics). Representative opioid receptor agonists include, but are not limited to: buprenorphine, butorphanol, codeine, dihydrocodeine, fentanyl, hydrocodone, hydromorphone, levallorphan, levorphanol, meperidine, methadone, morphine, nalbuphine, nalmefene, nalorphine, naloxone, naltrexone, nalorphine, oxycodone, oxymorphone, pentazocine, propoxyphene, tramadol, and combinations thereof. In certain embodiments, the opioid receptor agonist is selected from codeine, dihydrocodeine, hydrocodone, hydromorphone, morphine, oxycodone, oxymorphone, tramadol, and combinations thereof.

In a particular embodiment, the crystalline compounds are administered in combination with a phosphodiesterase (PDE) inhibitor, particularly a PDE-V inhibitor. Representative PDE-V inhibitors include, but are not limited to, avanafil, lodenafil, mirodenafil, sildenafil (Revatio®), tadalafil (Adcirca®), vardenafil (Levitra®), and udenafil.

In another embodiment, the crystalline compounds are administered in combination with a prostaglandin analog (also referred to as prostanoids or prostacyclin analogs). Representative prostaglandin analogs include, but are not limited to, beraprost sodium, bimatoprost, epoprostenol, iloprost, latanoprost, tafluprost, travoprost, and treprostinil, with bimatoprost, latanoprost, and tafluprost being of particular interest.

In yet another embodiment, the crystalline compounds are administered in combination with a prostaglandin receptor agonist, examples of which include, but are not limited to, bimatoprost, latanoprost, travoprost, and so forth.

The crystalline compounds may also be administered in combination with a renin inhibitor, examples of which include, but are not limited to, aliskiren, enalkiren, remikiren, and combinations thereof.

In another embodiment, the crystalline compounds are administered in combination with a selective serotonin reuptake inhibitor (SSRI). Representative SSRIs include, but are not limited to: citalopram and the citalopram metabolite desmethylcitalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline, and combinations thereof.

In one embodiment, the crystalline compounds are administered in combination with a 5-$HT_{1D}$ serotonin receptor agonist, examples of which include, by way of illustration and not limitation, triptans such as almotriptan, avitriptan, eletriptan, frovatriptan, naratriptan rizatriptan, sumatriptan, and zolmitriptan.

In one embodiment, the crystalline compounds are administered in combination with a sodium channel blocker, examples of which include, by way of illustration and not limitation, carbamazepine, fosphenyloin, lamotrignine, lidocaine, mexiletine, oxcarbazepine, phenyloin, and combinations thereof.

In one embodiment, the crystalline compounds are administered in combination with a soluble guanylate cyclase stimulator or activator, examples of which include, but are not limited to ataciguat, riociguat, and combinations thereof.

In one embodiment, the crystalline compounds are administered in combination with a tricyclic antidepressant (TCA), examples of which include, by way of illustration and not limitation, amitriptyline, amitriptylinoxide, butriptyline, clomipramine, demexiptiline, desipramine, dibenzepin, dimetacrine, dosulepin, doxepin, imipramine, imipraminoxide, lofepramine, melitracen, metapramine, nitroxazepine, nortriptyline, noxiptiline, pipofezine, propizepine, protriptyline, quinupramine, and combinations thereof.

In one embodiment, the crystalline compounds are administered in combination with a vasopressin receptor antagonist, examples of which include, by way of illustration and not limitation, conivaptan and tolvaptan.

Combined secondary therapeutic agents may also be helpful in further combination therapy with the crystalline compounds of the invention. For example, the crystalline compounds can be combined with a diuretic and an ARB, or a calcium channel blocker and an ARB, or a diuretic and an ACE inhibitor, or a calcium channel blocker and a statin. Specific examples include, a combination of the ACE inhibitor enalapril (in the maleate salt form) and the diuretic hydrochlorothiazide, which is sold under the mark Vaseretic®, or a combination of the calcium channel blocker amlodipine (in the besylate salt form) and the ARB olmesartan (in the medoxomil prodrug form), or a combination of a calcium channel blocker and a statin, all may also be used with the crystalline compound. Other therapeutic agents such as $\alpha_2$-adrenergic receptor agonists and vasopressin receptor antagonists may also be helpful in combination therapy. Exemplary $\alpha_2$-adrenergic receptor agonists include clonidine, dexmedetomidine, and guanfacine.

The following formulations illustrate representative pharmaceutical compositions comprising the crystalline compound of the invention.

Exemplary Hard Gelatin Capsules for Oral Administration

A crystalline compound (50 g), 440 g spray-dried lactose and 10 g magnesium stearate are thoroughly blended. The resulting composition is then loaded into hard gelatin capsules (500 mg of composition per capsule). Alternately, a crystalline compound (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Alternately, a crystalline compound (30 g), a secondary agent (20 g), 440 g spray-dried lactose and 10 g magnesium stearate are thoroughly blended, and processed as described above.

Exemplary Gelatin Capsule Formulation for Oral Administration

A crystalline compound (100 mg) is thoroughly blended with polyoxyethylene sorbitan monooleate (50 mg) and starch powder (250 mg). The mixture is then loaded into a gelatin capsule (400 mg of composition per capsule). Alternately, a crystalline compound (70 mg) and a secondary agent (30 mg) are thoroughly blended with polyoxyethylene sorbitan monooleate (50 mg) and starch powder (250 mg), and the resulting mixture loaded into a gelatin capsule (400 mg of composition per capsule).

Alternately, a crystalline compound (40 mg) is thoroughly blended with microcrystalline cellulose (Avicel PH 103; 259.2 mg) and magnesium stearate (0.8 mg). The mixture is then loaded into a gelatin capsule (Size #1, White, Opaque) (300 mg of composition per capsule).

Exemplary Tablet Formulation for Oral Administration

A crystalline compound (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, a crystalline compound (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, a crystalline compound (400 mg) is thoroughly blended with cornstarch (50 mg), croscarmellose sodium (25 mg), lactose (120 mg), and magnesium stearate (5 mg). The mixture is then compressed to form a single-scored tablet (600 mg of composition per tablet).

Alternately, a crystalline compound (100 mg) is thoroughly blended with cornstarch (100 mg) with an aqueous solution of gelatin (20 mg). The mixture is dried and ground to a fine powder. Microcrystalline cellulose (50 mg) and magnesium stearate (5 mg) are then admixed with the gelatin formulation, granulated and the resulting mixture compressed to form tablets (100 mg of the crystalline compound per tablet).

Exemplary Suspension Formulation for Oral Administration

The following ingredients are mixed to form a suspension containing 100 mg of the crystalline compound per 10 mL of suspension:

| Ingredients | Amount |
| --- | --- |
| Crystalline compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum ® K (magnesium aluminum silicate) | 1.0 g |
| Flavoring | 0.035 mL |
| Colorings | 0.5 mg |
| Distilled water | q.s. to 100 mL |

Exemplary Liquid Formulation for Oral Administration

A suitable liquid formulation is one with a carboxylic acid-based buffer such as citrate, lactate and maleate buffer solutions. For example, a crystalline compound (which may be pre-mixed with DMSO) is blended with a 100 mM ammonium citrate buffer and the pH adjusted to pH 5, or is blended with a 100 mM citric acid solution and the pH adjusted to pH 2. Such solutions may also include a solubilizing excipient such as a cyclodextrin, for example the solution may include 10 wt % hydroxypropyl-β-cyclodextrin.

Other suitable formulations include a 5% $NaHCO_3$ solution, with or without cyclodextrin.

Exemplary Injectable Formulation for Administration by Injection

A crystalline compound (0.2 g) is blended with 0.4 M sodium acetate buffer solution (2.0 mL). The pH of the resulting solution is adjusted to pH 4 using 0.5; N aqueous hydrochloric acid or 0.5; N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Exemplary Compositions for Administration by Inhalation

A crystalline compound (0.2 mg) is micronized and then blended with lactose (25 mg). This blended mixture is then loaded into a gelatin inhalation cartridge. The contents of the cartridge are administered using a dry powder inhaler, for example.

Alternately, a micronized crystalline compound (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 µm. The micronized composition is then loaded into metered-dose inhaler cartridges containing pressurized 1,1,1,2-tetrafluoroethane in an amount sufficient to provide about 10 µg to about 500 µg of the crystalline compound per dose when administered by the inhaler.

Alternately, a crystalline compound (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1N NaOH. The solution is administered using a nebulizer device that provides about 10 µg to about 500 µg of the compound per dose.

EXAMPLES

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard, generally accepted meaning:

AcOH acetic acid
BOC t-butoxycarbonyl
CPME cyclopentyl methyl ether
DCM dichloromethane or methylene chloride
DIPE Diisopropyl ether
DIPEA N,N-diisopropylethylamine
DMF N,N-dimethylformamide
$Et_3N$ triethylamine
EtOAc ethyl acetate
EtOH ethanol
HATU N,N,N',N'-tetramethyl-O-(7-azabenzotriazol-1-yl) uronium hexafluorophosphate
IPA isopropanol
MeCN acetonitrile
MeOH methanol
MeTHF 2-methyltetrahydrofuran
PMB p-methoxybenzyl
PyBOP benzotriazol-1-yloxytris(pyrrolidino)phosphonium hexafluorophosphate
TFA trifluoroacetic acid
THF tetrahydrofuran Unless noted otherwise, all materials, such as reagents, starting materials and solvents, were purchased from commercial suppliers (such as Sigma-Aldrich, Fluka Riedel-de Haën, and the like) and were used without further purification.

Reactions were run under nitrogen atmosphere, unless noted otherwise. The progress of reactions were monitored by thin layer chromatography (TLC), analytical high performance liquid chromatography (anal. HPLC), and mass spectrometry, the details of which are given in specific examples. Solvents used in analytical HPLC were as follows: solvent A was 98% $H_2O$/2% MeCN/1.0 mL/L TFA; solvent B was 90% MeCN/10% $H_2O$/1.0 mL/L TFA.

Reactions were worked up as described specifically in each preparation for example; commonly reaction mixtures were purified by extraction and other purification methods such as temperature-, and solvent-dependent crystallization, and precipitation. In addition, reaction mixtures were routinely purified by preparative HPLC, typically using Microsorb C18 and Microsorb BDS column packings and conventional eluents. Progress of reactions was typically measured by liquid chromatography mass spectrometry (LCMS). Characterization of isomers were done by Nuclear Overhauser effect spectroscopy (NOE). Characterization of reaction products was routinely carried out by mass and $^1$H-NMR spectrometry. For NMR measurement, samples were dissolved in deuterated solvent ($CD_3OD$, $CDCl_3$, or DMSO-$d_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

Preparation 1

N'-(3'-Chlorobiphenyl-4-ylmethyl)hydrazinecarboxylic acid t-Butyl Ester

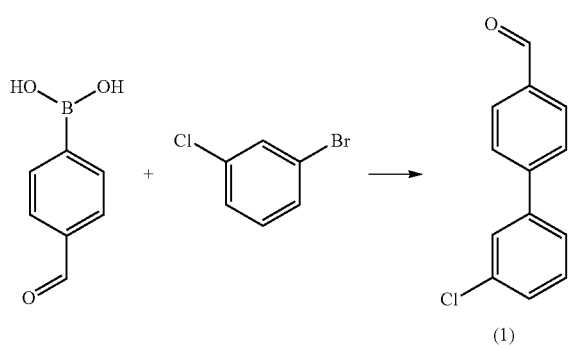 [SMILES: O=Cc1ccc(B(O)O)cc1 ; Clc1cccc(Br)c1 ; O=Cc1ccc(-c2cccc(Cl)c2)cc1]

(1)

4-Formylphenylboronic acid (18 g, 120 mmol) was combined with MeTHF (300 mL), 3-chlorobromobenzene (14.1 mL, 120 mmol) and 1M aqueous $Na_2CO_3$ (120 mL). The mixture was flushed with nitrogen three times and 1,1'-bis(di-t-butylphosphino)ferrocene palladium dichloride (540 mg, 840 mmol) was added. The mixture was again flushed with nitrogen three times, then stirred for 30 minutes while increasing the temperature to 30° C. The mixture was then heated to 50° C. until the reaction was complete (~2 hours). The mixture was cooled to room temperature, 1M aqueous $Na_2CO_3$ (120 mL) was added, and the mixture was stirred overnight at room temperature. The layers were separated and the organic layer was collected, dried over $NaSO_4$ and filtered. It was partially concentrated (to a 150 mL volume). To the solution was added Si—SH (mercaptan modified silica gel, ~2 g). The mixture was stirred at room temperature for 2 hours then filtered through Celite®. The cake was washed with MeTHF (100 mL) to yield Compound 1 (25 g), which was used without further purification.

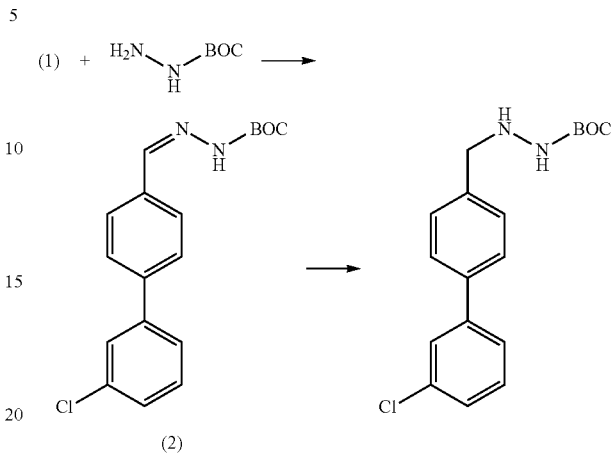

Compound 1 (25.0 g, 115.4 mmol) was combined with MeTHF (150 mL) and t-butyl carbazate (15.6 g, 118.0 mmol), and stirred at room temperature for one hour. AcOH (5 mL) was added and the resulting mixture was stirred for one hour, yielding Compound 2, which was allowed to sit overnight.

A mixture of Compound 2 in MeTHF (250 mL) and AcOH (20.0 mL) was flushed with nitrogen and cooled with an ice bath to 0° C. After stirring for 30 minutes, sodium cyanoborohydride (8.7 g, 138 mmol) was added over 5 minutes. The resulting mixture was stirred at 0° C. for one hour, slowly warmed to room temperature and stirred until completion (~20 hours). The mixture was cooled with an ice bath and 1M aqueous NaOH (346.2 mL, 346.2 mmol) was added. MeTHF (100 mL, 1.0 mol) was then added and the mixture was allowed to warm to room temperature. The layers were separated and the organic layer was washed with 1M aqueous NaOH (150 mL, 150 mmol). The layers were separated and the organic layer was dried over $Na_2SO_4$, filtered, and concentrated to yield an oil, which was dissolved in ether (250 mL, 2.4 mol) and stirred overnight. The mixture was concentrated to yield the title compound (35 g), which was used without further purification.

Preparation 2

(R)-3-{N-(3'-Chlorobiphenyl-4-ylmethyl)-N'-[3-(4-methoxybenzyloxy)isoxazole-5-carbonyl]hydrazino}-2-hydroxypropionic Acid Isopropyl Ester

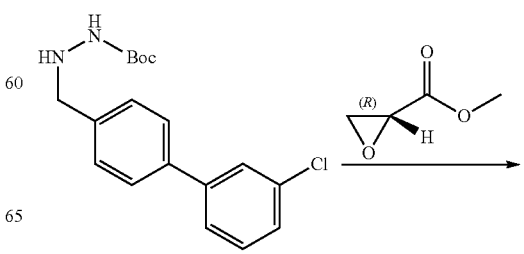

-continued

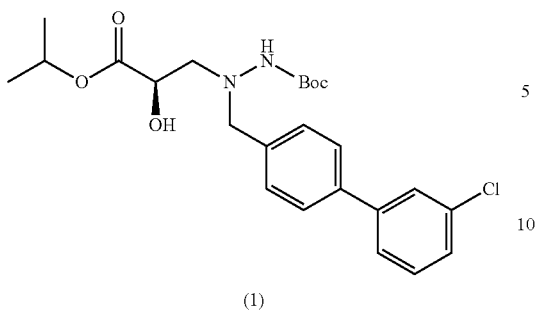

(1)

N'-(3'-Chlorobiphenyl-4-ylmethyl)hydrazinecarboxylic acid t-butyl ester (400.0 g, 1.2 mol) was combined with IPA (7.0 L, 91 mol) and (R)-oxirane-2-carboxylic acid methyl ester (105.2 mL, 1.2 mol) under nitrogen. The mixture was heated at 83° C. for 51 hours. Additional (R)-oxirane-2-carboxylic acid methyl ester (52.61 mL, 600.9 mmol) was added and the mixture was heated at 84° C. for 48 hours. Sodium cyanoborohydride (1.0 g, 16 mmol) was added and the mixture was heated at 80° C. and the reaction monitored (≈48 hours). Additional sodium cyanoborohydride (1 g) was added and the mixture was heated at reflux (≈3 days). The mixture was then cooled slowly at 15° C.; filtered, and dried to yield Compound 1 (470 g).

(1) ⟶

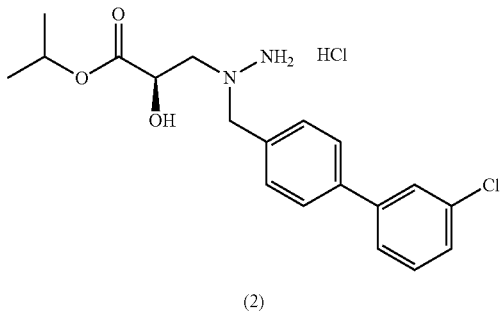

(2)

Compound 1 (880 mg, 1.9 mmol) was combined with 3 M HCl in CPME (7 mL, 20 mmol). The mixture was then stirred on an ice bath and the reaction monitored for completion (≈2.5 hours). The solids were collected, washed with CPME (0.5 mL), and dried to yield a white powder (0.6 g; HCl salt). The powder was then dissolved in IPA (15 mL) and heated to reflux. The resulting slurry was allowed to cooled to room temperature and stirred for 1 hour. The solids were collected to yield Compound 2 as a white solid.

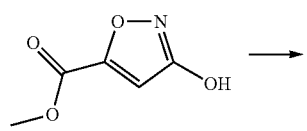 ⟶

-continued

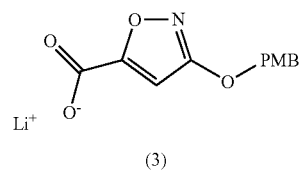

(3)

To a stirred solution of methyl 3-hydroxyisoxazole-5-carboxylate (5.0 g, 35 mmol) in DMF (20 mL, 300 mmol) at 0° C. was added $K_2CO_3$ (5.4 g, 39.4 mmol). After 10 minutes at room temperature p-methoxybenzyl chloride (5.5 mL, 40.2 mmol) was added in one portion. The resulting mixture was heated at 60° C. for 2 hours and then cooled to room temperature and stirred overnight. 1.0 M HCl in water (150 mL) and EtOAc (150 mL) were added and the phases were separated. The organic layer was washed with saturated aqueous NaCl (10 mL), dried over $Na_2SO_4$, and the solvent removed by rotary evaporation to yield a thick oil. The oil was dissolved in THF (35 mL) and MeOH (35 mL), followed by addition of LiOH monohydrate (2.9 g, 69.9 mmol) dissolved in water (35 mL). The resulting mixture was stirred at room temperature and the reaction monitored for completion (≈3 hours). Solvent was removed by rotary evaporation at 30° C. to yield a pasty solid. Toluene (100 mL) was added and the volume was reduced (to ~50 mL). EtOAc (200 mL) was added and the volume was reduced (to ~50 mL). Filtration and drying yielded a solid (10 g), which was dissolved in water (200 mL), and the pH was adjusted slowly with concentrated HCl to ≈2. EtOAc (200 mL) was added and the phases were separated. The aqueous layer was back extracted with EtOAc (200 mL). The combined organic layers were dried over $Na_2SO_4$, followed by solvent removal. The product was reslurried in EtOAc:hexanes (1:1) followed by filtration to yield Compound 3 (>99% purity).

(2) + (3) ⟶

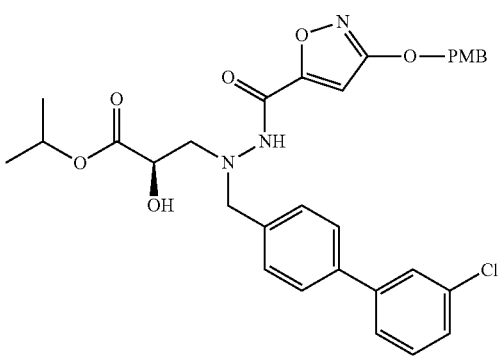

Compound 2 (18.0 g, 26.8 mmol) in DMF (90 mL) was combined with Compound 3 (7.3 g, 29 mmol) in DIPEA (12 mL, 67 mmol). The mixture was cooled at 0° C. followed by the portion-wise addition of PyBOP (18 g, 35 mmol) and the reaction monitored for completion (≈30 minutes at 0° C.). Water (540 mL) and EtOAc (540 mL) were added and the phases were separated. The organic layer was washed with saturated aqueous NaCl (500 mL) and dried over $Na_2SO_4$, followed by solvent removal. The crude product was purified (SiG chromatography; 300 g column, 10-30-50% EtOAc/hexanes) to yield the title compound (9 g; >98% purity).

Preparation 3

(R)-3-[N-(3'-Chlorobiphenyl-4-ylmethyl)hydrazino]-2-hydroxypropionic Acid Ethyl Ester

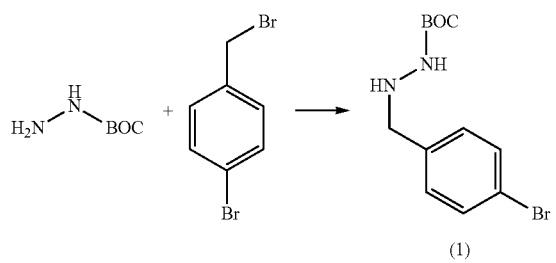 [SMILES: CC(C)(C)OC(=O)NN ; BrCc1ccc(Br)cc1 ; CC(C)(C)OC(=O)NNCc1ccc(Br)cc1]

(1)

4-Bromobenzyl bromide (5.0 g, 20 mmol) and DIPEA (3.48 mL, 20.0 mmol) were dissolved in DMF (20 mL). t-Butyl carbazate (7.9 g, 60.0 mmol) was added and the mixture was stirred at room temperature until the reaction was complete. The mixture was partially concentrated, and the residue was partitioned between EtOAc and a saturated aqueous NaHCO₃ solution. The EtOAc layer was then dried over Na₂SO₄ and concentrated. The crude product was purified by flash chromatography to yield Compound 1 (3.8 g).

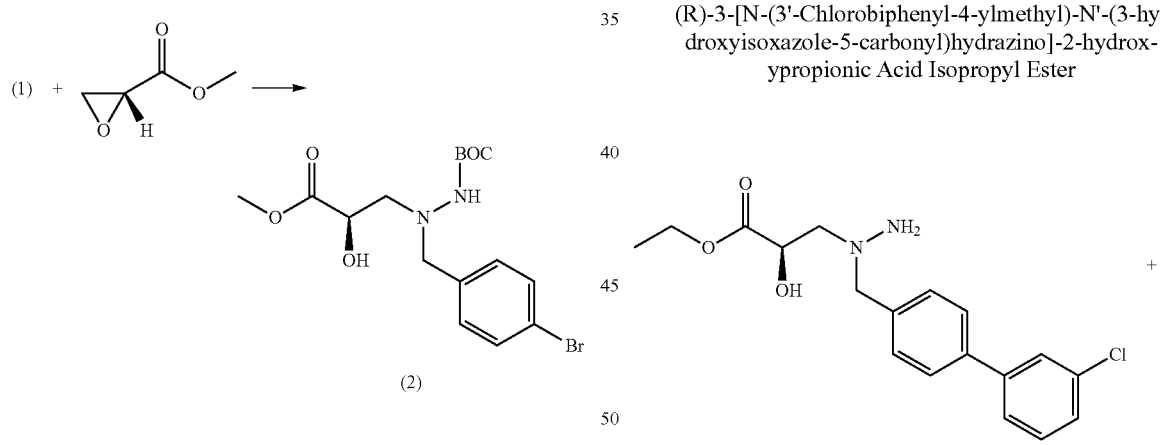

(2)

Compound 1 (1.9 g, 6.3 mmol) was dissolved in IPA (26.4 mL). Methyl (2R)-glycidate (1.1 mL, 12.6 mmol) was added and the mixture was heated at 90° C. until the reaction was complete (~4 days). The mixture was cooled to room temperature and concentrated to yield Compound 2 (2.5 g) as a white solid.

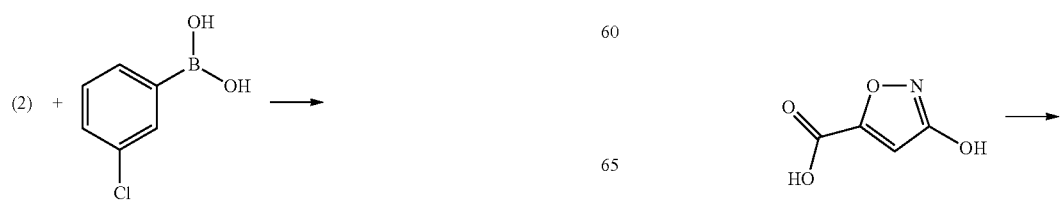

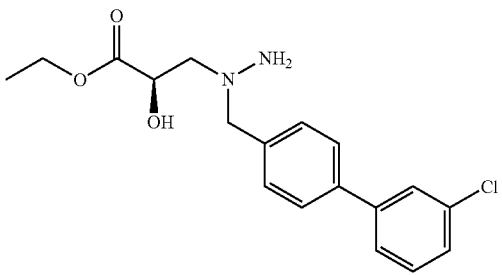

(3)

Compound 2 (600 mg, 1 mmol), 3-chlorophenylboronic acid (419 mg, 2.7 mmol), and K₂CO₃ (617 mg, 4.5 mmol) were combined in EtOH (5 mL) and water (1 mL), followed by the addition of SilicaCat®Pd(0) (0.09 mmol/g loading, 1160 mg, 104 mmol). The mixture was heated at 120° C. until the reaction was complete (≈30 minutes). The mixture was filtered and concentrated. The residue was dissolved into MeN/AcOH and purified by reverse phase chromatography (55 g column; gradient 30-95% MeCN in water with 0.1% TFA). The clean fractions were collected, concentrated and then dissolved in 4M HCl in dioxane (6 mL) and EtOH (6 mL). The mixture was stirred at room temperature overnight, then concentrated to yield the title compound (250 mg), which was used without further purification.

Preparation 4

(R)-3-[N-(3'-Chlorobiphenyl-4-ylmethyl)-N'-(3-hydroxyisoxazole-5-carbonyl)hydrazino]-2-hydroxypropionic Acid Isopropyl Ester -continued

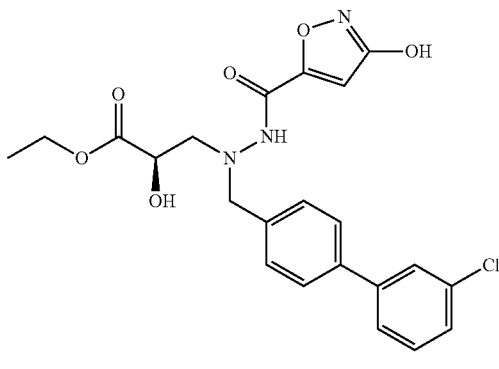

(1)

3-Hydroxyisoxazole-5-carboxylic acid (888 mg, 6.9 mmol), HATU (2.6 g, 6.9 mmol) and DMF were combined and the resulting mixture was stirred for 5 minutes at room temperature. DIPEA (2.3 mL, 13.2 mmol) and (R)-3-[N-(3'-chlorobiphenyl-4-ylmethyl)-hydrazino]-2-hydroxy-propionic acid ethyl ester (2.0 g, 5.7 mmol) were added and the resulting mixture was stirred until the reaction was complete (20 minutes). The reaction was quenched with water, the mixture was diluted with EtOAc, then washed with water and saturated aqueous NaCl. The organic layer was dried, concentrated, and purified by flash chromatography (50-90% EtOAc in hexanes with 0.1% Et$_3$N). The clean fractions were collected and concentrated. The organic layer, was dissolved into DCM, and the precipitate was filtered and rinsed with DCM to yield Compound 1 as a TFA salt (1.3 g; purity 96%). MS m/z [M+H]$^+$ calc'd for $C_{22}H_{22}ClN_3O_6$, 460.12. found 460.4.

(1) ⟶

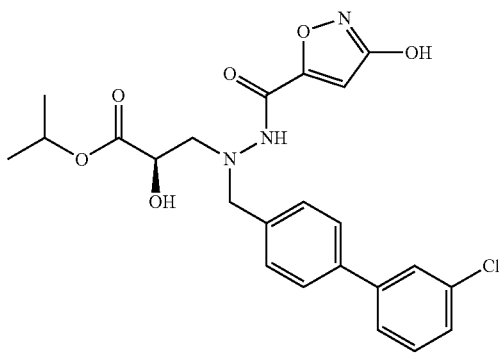

Compound 1 (1.4 g, 3.0 mmol) was dissolved in IPA (20 mL, 0.2 mol) and 4 M HCl in dioxane (9 mL, 40 mmol) was added. The mixture was stirred at room temperature overnight (18 hours). The mixture was warmed to 60° C. for 1 hour, then cooled back to room temperature and stirred for 2 hours. The mixture was concentrated and purified (Interchim C18 reverse phase chromatography column, 30-90% MeCN in water for 22 minutes). The clean fractions were combined and lyophilized to yield the title compound (110 mg; purity 98%). MS m/z [M+H]$^+$ calc'd for $C_{23}H_{24}ClN_3O_6$, 474.14. found 474.2.

Example 1

Crystalline Neutral Monohydrate Form 1

(R)-3-[N-(3'-Chlorobiphenyl-4-ylmethyl)-N'-(3-hydroxy-isoxazole-5-carbonyl)hydrazino]-2-hydroxypropionic acid isopropyl ester (1.0 g, 2.1 mmol) was dissolved in MeOH (5.0 mL, 120 mmol). Water (10 mL) was added and a milky suspension was formed. The suspension was heated until a free-flowing slurry developed (30 minutes at 70° C.), yielding very small particles, which were filtered and dried (850 g). This product was then analyzed by PXRD, DSC, and TGA, as described in the examples below, and was designated crystalline neutral monohydrate Form 1.

Example 2

Crystalline Neutral Monohydrate Form 1

Crystalline neutral Form 2 (2.0 g, 4.2 mmol) was dissolved in MeOH (10 mL, 200 mmol). Water (20 mL) was added dropwise and a thick slurry was formed. The slurry was heated at 60° C. for 30 minutes (remained a slurry), followed by slow cooling and stirring at room temperature overnight. Filtration and drying yielded a white solid (1.9 g).

This product was then analyzed by PXRD, DSC, and TGA, as described in the examples below, and was found to be the crystalline neutral monohydrate Form 1. This data is presented in FIGS. 1-5.

Example 3

Crystalline Neutral Monohydrate Form 1

(R)-3-[N-(3'-Chlorobiphenyl-4-ylmethyl)-N'-(3-hydroxy-isoxazole-5-carbonyl)hydrazino]-2-hydroxypropionic acid isopropyl ester (200 mg) was dissolved in MeCN (3 mL) in a reaction vessel, by immersing the vessel in warm water and sonicating the contents for 3 minutes. The resultant clear solution was transferred to a clean vessel and allowed to evaporate at room temperature over a period of 16 hours. Crystalline particles appeared in solution and were collected by filtration and dried under vacuum. The dried solid was then analyzed by PXRD, DSC, and TGA, as described in the examples below, and was found to be the crystalline neutral monohydrate Form 1.

Example 4

Crystalline Neutral Form 2

Preparation of seed crystals: A small amount of crude (R)-3-[N-(3'-chlorobiphenyl-4-ylmethyl)-N'-(3-hydroxy-isoxazole-5-carbonyl)-hydrazino]-2-hydroxypropionic acid isopropyl ester was partitioned between 20% aqueous NH$_4$Cl and DCM. The phases were separated. After 15 minutes solids formed in the DCM solution. There was no significant loss of product to the water layer.

(R)-3-[N-(3'-chlorobiphenyl-4-ylmethyl)-N'-(3-hydroxy-isoxazole-5-carbonyl)-hydrazino]-2-hydroxypropionic acid isopropyl ester (2.2 g) was combined with DCM (30 mL) and 20% aqueous NH$_4$Cl (30 mL). Seeds were added and the resulting mixture was stirred at room temperature for 4 hours, forming a white slurry. The slurry was filtered, air dried for 1 hour, then dried in vacuo overnight at room temperature to yield a solid (2 g; purity ~98%). This product was then analyzed by PXRD, DSC, and TGA, as described in the examples below, and was designated crystalline neutral Form 2. The DSC and TGA is data is presented in FIGS. 9 and 10.

Example 5

Crystalline Neutral Form 2

Crude (R)-3-[N-(3'-Chlorobiphenyl-4-ylmethyl)-N'-(3-hydroxyisoxazole-5-carbonyl)-hydrazino]-2-hydroxypropionic acid isopropyl ester (2.4 g) was combined with DCM (30 mL) and 20% aqueous $NH_4Cl$ (30 mL). Seeds (Form 2) were added and the resulting mixture was stirred at room temperature overnight. The material was then reslurried in DCM (30 mL) for ≈48 hours to yield an off-white solid (2.2 g) after drying in vacuo. This product was then analyzed by PXRD, DSC, and TGA, as described in the examples below, and was found to be the crystalline neutral Form 2. The PXRD data is presented in FIG. 8.

Example 6

Crystalline Neutral Form 2

Several lots of crystalline neutral Form 2 (16.5 g) were combined and reslurried in 10 volumes of DCM at 35° C. to yield 16.2 g of 98.5% pure material after drying. This product was then analyzed by PXRD, DSC, and TGA, as described in the examples below, and was found to be the crystalline neutral Form 2.

Example 7

Crystalline Neutral Form 2

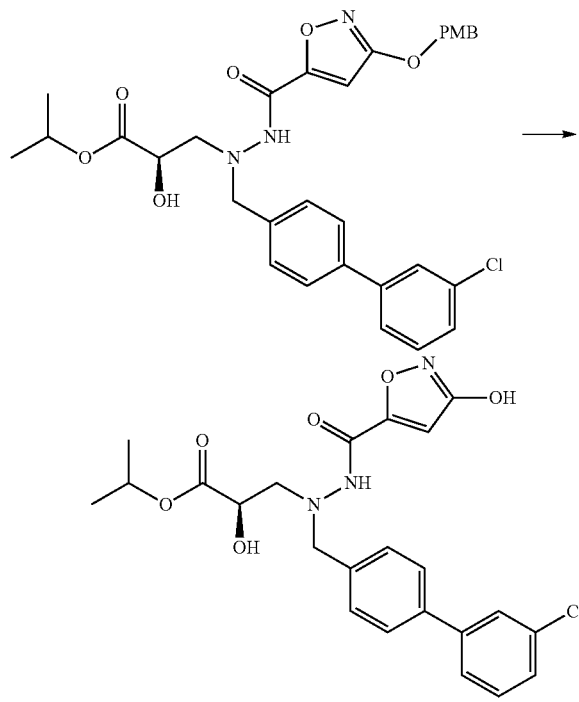

(R)-3-{N-(3'-Chlorobiphenyl-4-ylmethyl)-N'-[3-(4-methoxybenzyloxy)isoxazole-5-carbonyl]hydrazino}-2-hydroxypropionic acid isopropyl ester (10.0 g, 16.8 mmol) was dissolved in DCM (50 mL). Anisole (9.2 mL, 84.2 mmol) and TFA (6.5 mL, 84.2 mmol) were added via syringe and the resulting mixture was stirred at room temperature until the reaction was complete (≈3 hours). DIPE (50 mL, 400 mmol) and seeds (Form 2) were added, forming a slurry. The slurry was stirred at room temperature for 1 hour, then filtered. The flask and filter cake were washed with DCM (20 mL) to yield 6.3 g of 97% pure material after drying. This product was then analyzed by PXRD, DSC, and TGA, as described in the examples below, and was found to be the crystalline neutral Form 2.

Example 8

Crystalline Neutral Solvated Form 2'

(R)-3-[N-(3'-chlorobiphenyl-4-ylmethyl)-N'-(3-hydroxyisoxazole-5-carbonyl)hydrazino]-2-hydroxypropionic acid isopropyl ester (200 mg) was suspended in EtOAc (2 mL). Hexanes (2 mL) were added and the resulting mixture was heated at 60° C. for 1 hour, yielding a thin slurry. The slurry was slowly cooled to room temperature, filtered and dried to yield a solid product.

This product was then analyzed by PXRD, DSC, and TGA, as described in the examples below, and was designated crystalline neutral solvated Form 2'. This data is presented in FIGS. 17, 19, and 21.

Example 9

Crystalline Neutral Solvated Form 2'

(R)-3-[N-(3'-chlorobiphenyl-4-ylmethyl)-N'-(3-hydroxyisoxazole-5-carbonyl)hydrazino]-2-hydroxypropionic acid isopropyl ester (400 mg) was recrystallized twice from 10 volumes of EtOAc. The resulting mixture was heated to 70° C. then cooled to room temperature, filtered and dried to yield a solid product.

Figure 18:
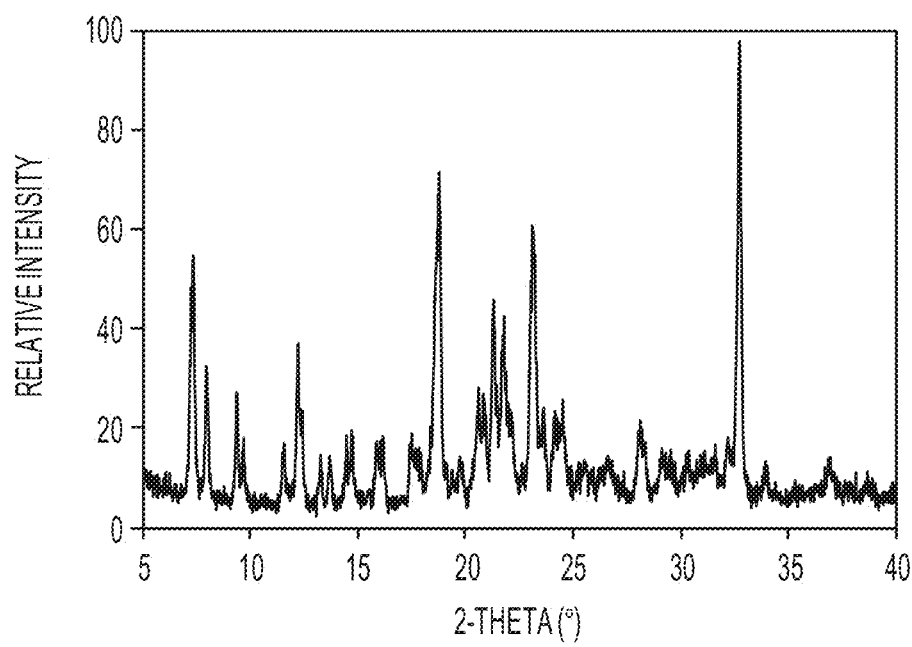

This product was then analyzed by PXRD, DSC, and TGA, as described in the examples below, and was found to be the crystalline neutral solvated Form 2'. This data is presented in FIGS. 18, 20, and 22.

Example 10

Crystalline Neutral Anhydrous Form 3

Crystalline neutral Form 2 (≈20 mg; prepared as described in Example 4) was loaded onto a TGA pan and subjected to heating at the rate of 10° C./min to 100° C. The sample was kept at this temperature for 3 minutes and then was heated up to 110° C. (at the rate of 10° C./min) and maintained at this temperature for 10 minutes. The sample was further heated up to 120° C. (at the rate of 10° C./min) and maintained at this temperature for 5 minutes. The sample was allowed to cool under ambient conditions to room temperature and subjected to analysis. This heat-cooled sample was then analyzed by PXRD, DSC, and TGA, as described in the examples below, and was designated crystalline neutral anhydrous Form 3. This data is presented in FIGS. 29 and 30.

Example 11

Crystalline Neutral Anhydrous Form 3

Crystalline neutral Form 2 (≈600 mg; prepared as described in Example 4) of TR-53150 (lot MR-10583-30-1)

was placed in a 20 mL glass vial and immersed in sandbath that was heated to 105-110° C. over a period of three hours. The sample was maintained at this temperature for 16 hours and then allowed to cool to room temperature under ambient conditions. This heat-cooled sample was then analyzed by PXRD, DSC, and TGA, as described in the examples below, and was found to be the crystalline neutral anhydrous Form 3. This data is presented in FIGS. 25-28.

Example 12

Crystalline Neutral Anhydrous Form 4

Crystalline neutral monohydrate Form 1 (lot JN-2413-06) (≈30 mg; prepared as described in Example 3)) was loaded onto a TGA pan and subjected to heating at the rate of 10° C./min to 120° C. The sample was maintained at this temperature for 5 minutes and then allowed to cool under ambient conditions to room temperature. This heat-cooled sample was then analyzed by PXRD, DSC, and TGA, as described in the examples below, and was designated crystalline neutral anhydrous Form 4. This data is presented in FIGS. 33-36.

Example 13

Crystalline Neutral Anhydrous Form 4

Figure 38:
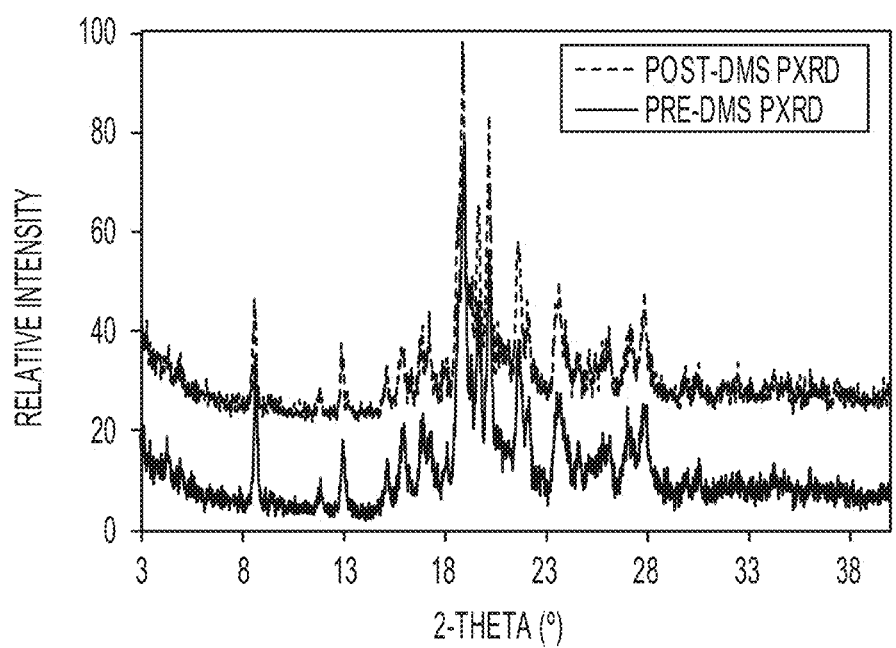
FIG. 38 shows the overlay of the PXRD patterns of the sample before and after being subjected to the moisture sorption-desorption experiment for this form.

Crystalline neutral monohydrate Form 1 (lot MR-10616-15) (≈25 mg; prepared as described in Example 2) was loaded onto a TGA pan and subjected to heating at the rate of 10° C./min to 120° C. The sample was maintained at this temperature for 5 minutes and then allowed to cool under ambient conditions to room temperature. This heat-cooled sample was then analyzed by PXRD, DSC, and TGA, as described in the examples below, and was found to be the crystalline neutral anhydrous Form 4. This data is presented in FIGS. 37 and 38.

Example 14

Crystalline Tromethamine Salt (R)-3-[N-(3'-Chlorobiphenyl-4-ylmethyl)-N'-(3-hydroxy-isoxazole-5-carbonyl)hydrazino]-2-hydroxypropionic acid isopropyl ester (50.1 mg) was dissolved in EtOH (0.5 mL). Tromethamine (26 mg) was dissolved in EtOH (1 mL) in a separate reaction vessel, by immersing the vessel in warm water and sonicating the contents. The two solutions were then mixed and subjected to intermittent heating (to 50° C.) and sonication for 3 minutes. The resultant clear solution was transferred to a clean vessel and allowed to evaporate at room temperature over a period of two days. Crystalline particles appeared at the bottom of the vessel, and were collected by filtration, washed with DIPE, and dried under vacuum to yield a solid product (82% yield).

This product was then analyzed by PXRD, DSC, and TGA, as described in the examples below, and was designated crystalline tromethamine salt. This data is presented in FIGS. 41-44.

Example 15

Crystalline L-Lysine Salt (R)-3-[N-(3'-Chlorobiphenyl-4-ylmethyl)-N'-(3-hydroxy-isoxazole-5-carbonyl)hydrazino]-2-hydroxypropionic acid isopropyl ester (101.1 mg) was dissolved in EtOH (1 mL). L-lysine (31.2 mg) was dissolved in 80:20 EtOH:water (2 mL) in a separate reaction vessel, by immersing the vessel in warm water and sonicating the contents. The two solutions were then mixed and subjected to intermittent heating (to 50° C.) and sonication for 10 minutes. The resultant clear solution was transferred to a clean vessel and allowed to evaporate at room temperature over a period of four days. Crystalline particles appeared in the vessel, and were collected by filtration, washed with DIPE, and dried under vacuum to yield a solid product (90% yield).

This product was then analyzed by PXRD, DSC, and TGA, as described in the examples below, and was designated crystalline L-lysine salt. This data is presented in FIGS. 46-48.

Example 16

Crystalline Meglumine Salt (R)-3-[N-(3'-Chlorobiphenyl-4-ylmethyl)-N'-(3-hydroxy-isoxazole-5-carbonyl)hydrazino]-2-hydroxypropionic acid isopropyl ester (100.2 mg) was dissolved in EtOH (1 mL). Meglumine (N-methyl-D-glucamine) (41.3 mg) was dissolved in EtOH (1 mL) in a separate reaction vessel, by swirling the vessel and sonicating the contents. The two solutions were then mixed and subjected to intermittent heating (to 50° C.) and sonication for 5 minutes. The resultant clear solution was transferred to a clean vessel and allowed to evaporate at room temperature over a period of three days. The resultant solid showed some birefringent particles in mass of amorphous, gummy material. This solid was dissolved in 1:1 EtOH:acetone (3 ml) by gentle warming (40° C.) and sonication. The resultant solid contained a greater amount of crystalline particles and small amount of amorphous material. This solid was washed with DIPE, and dried under vacuum to yield a solid product (60% yield).

This product was then analyzed by PXRD, DSC, and TGA, as described in the examples below, and was designated crystalline meglumine salt. This data is presented in FIGS. 50-51.

Powder X-Ray Diffraction

Powder X-ray diffraction analysis of the crystalline compounds was performed using a Thermo ARL X'Tra diffractometer. The X-ray source was Cu—Kα radiation ($\lambda$=1.54051 Å) with output voltage of 40 kV and current of 45 mA. The instrument was operated in Bragg-Brentano geometry with incident, divergence, and scattering slits set to maximize the intensity at the sample. For measurements, a small amount of each crystalline compound (5-25 mg) was gently pressed onto the pitted sample holder to form a smooth surface and subjected to X-ray exposure. The samples were scanned in 2θ-θ mode from 2° to 40° in 2θ with a step size of 0.02° or 0.03° and a scan speed of 2.0° per minute or 1-4 seconds exposure per step. The data acquisition was controlled by Thermo ARL Measurement software and analyzed by Jade software (version 7.5.1).

It should be kept in mind that the Bragg-Brentano geometry used in the data collection is prone to preferred orientation. Under these conditions it is possible that the relative intensities of the diffraction peaks may not represent the true relative intensities that would be obtained from an idealized distribution of spherical particles or from a diffraction pattern simulated from a single crystal data. It is also possible that some peaks are not seen in some diffraction patterns due to the extensive preferred orientation.

Differential Scanning Calorimetry

The crystalline compounds were subjected to temperature scan using a TA Instruments Q100 differential scanning calorimeter equipped with a refrigerated cooling system. Samples were loaded into aluminum pans with crimped lids. In most cases, the samples were heated to 250° C. at a rate of 10° C. per minute under a purge of nitrogen gas. The data acquisition was controlled by Thermal Advantage software Release 5.1.2 and the data were analyzed with Universal Analysis 2000 software (version 4.7A).

Thermogravimetric Analysis

The crystalline compounds were subjected to temperature scan using a TA Instruments Q500 thermal gravimetric analyzer. Samples were loaded into platinum pans and heated to 250° C. at a rate of 10° C. per minute under a purge of nitrogen gas. The data acquisition was controlled by Thermal Advantage software Release 5.1.2 and the data were analyzed with Universal Analysis 2000 software (version 4.7A).

Polarized Light Microscopy

For polarized light microscopy (PLM) studies, samples were examined under an optical microscope (Olympus BX51) with cross-polarized light filter. Images were collected with a PaxCam camera controlled by PaxIt Imaging Software (version 6.4). Samples were prepared on glass slides with light mineral oil as immersion medium. Depending on the size of the particles, a 4×, a 10× or a 20× objective lens was used for magnification.

Dynamic Moisture Sorption Assessment

Moisture sorption and desorption data on the crystalline compounds were collected on a VTI SGA-100 Vapor Sorption Analyzer. Sorption and desorption data were collected over a range of 5% to 90% relative humidity (RH) at 5% RH intervals. Equilibrium criteria used for analysis were less than 0.01% weight change in 5 minutes, with a maximum equilibration time of three hours if the weight criterion was not met. Samples were subjected to initial drying or desorption steps to 5% RH followed by the sorption-desorption cycle. Data were collected at a time interval of two minutes or 0.01% change in weight.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents, and patent applications cited herein are hereby incorporated by reference in their entirety to the same extent as if each document had been individually incorporated by reference herein.

What is claimed is:

1. A crystalline (R)-3-[N-(3'-chlorobiphenyl-4-ylmethyl)-N'-(3-hydroxyisoxazole-5-carbonyl)hydrazino]-2-hydroxypropionic acid isopropyl ester, selected from:

a neutral monohydrate Form 1 characterized by a powder x-ray diffraction pattern comprising diffraction peaks at 2θ values of 8.26±0.20, 14.68±0.20, 15.64±0.20, 16.36±0.20, 18.52±0.20, 20.40±0.20, 21.08±0.20, 21.48±0.20, 21.68±0.20, 23.18±0.20, 24.50±0.20, 24.80±0.20, 25.34±0.20, and 26.56±0.20;

a neutral Form 2 characterized by a powder x-ray diffraction pattern comprising diffraction peaks at 2θ values of 7.48±0.20, 8.02±0.20, 9.38±0.20, 12.24±0.20, 14.86±0.20, 18.72±0.20, 20.94±0.20, 21.34±0.20, 22.32±0.20, and 24.68±0.20;

a neutral solvated Form 2' characterized by a powder x-ray diffraction pattern comprising diffraction peaks at 2θ values of 7.26±0.20, 8.05±0.20, 12.20±0.20, 14.48±0.20, 15.84±0.20, 16.22±0.20, 18.78±0.20, 20.60±0.20, 21.29±0.20, 21.74±0.20, 23.10±0.20, 24.16±0.20, and 24.44±0.20;

a neutral anhydrous Form 3 characterized by a powder x-ray diffraction pattern comprising diffraction peaks at 2θ values of 8.12±0.20, 8.86±0.20, 11.92±0.20, 13.68±0.20, 16.10±0.20, 18.12±0.20, 18.46±0.20, 19.06±0.20, 19.48±0.20, 20.60±0.20, 21.28±0.20, 24.46±0.20, 25.94±0.20, and 26.40±0.20;

a neutral anhydrous Form 4 characterized by a powder x-ray diffraction pattern comprising diffraction peaks at 2θ values of 8.70±0.20, 13.00±0.20, 16.00±0.20, 16.94±0.20, 17.36±0.20, 18.72±0.20, 19.00±0.20, 19.78±0.20, 20.24±0.20, 21.70±0.20, 23.68±0.20, and 27.94±0.20;

a tromethamine salt characterized by a powder x-ray diffraction pattern comprising diffraction peaks at 2θ values of 6.94±0.20, 9.00±0.20, 12.36±0.20, 13.74±0.20, 16.58±0.20, 17.12±0.20, 18.32±0.20, 19.86±0.20, 20.28±0.20, 21.36±0.20, 23.82±0.20, and 27.00±0.20;

an L-lysine salt characterized by a powder x-ray diffraction pattern comprising diffraction peaks at 2θ values of 3.10±0.20, 9.13±0.20, 10.12±0.20, 12.14±0.20, 18.33±0.20, 18.54±0.20, 20.14±0.20, 20.88±0.20, 21.72±0.20, 23.12±0.20, and 24.58±0.20; and a meglumine salt characterized by a powder x-ray diffraction pattern comprising diffraction peaks at 2θ values of 6.10±0.20, 8.72±0.20, 10.20±0.20, 12.24±0.20, 15.32±0.20, 17.04±0.20, 18.46±0.20, 19.40±0.20, 20.46±0.20, 21.12±0.20, 23.12±0.20, and 25.96±0.20.

2. The crystalline neutral monohydrate Form 1 of claim 1, which is characterized by having one or more additional diffraction peaks at 2θ values selected from 9.26±0.20, 9.82±0.20, 18.06±0.20, 22.58±0.20, 23.61±0.20, 28.36±0.20, 29.42±0.20, 32.28±0.20, and 34.76±0.20.

3. The crystalline neutral monohydrate Form 1 of claim 1, which is characterized by a powder x-ray diffraction pattern in which the peak positions are substantially in accordance with the peak positions of the pattern shown in FIG. 1.

4. The crystalline neutral monohydrate Form 1 of claim 1, which is characterized by a differential scanning calorimetry thermogram which has a melting point within the range of about 160-166° C.

5. The crystalline neutral monohydrate Form 1 of claim 1, which is characterized by a differential scanning calorimetry thermogram substantially in accordance with that shown in FIG. 2.

6. The crystalline neutral Form 2 of claim 1, which is characterized by having one or more additional diffraction peaks at 2θ values selected from 9.74±0.20, 11.66±0.20, 12.00±0.20, 13.26±0.20, 15.50±0.20, 16.14±0.20, 17.64±0.20, 17.98±0.20, 19.78±0.20, 21.82±0.20, 23.34±0.20, 23.66±0.20, 26.62±0.20, and 28.46±0.20.

7. The crystalline neutral Form 2 of claim 1, which is characterized by a powder x-ray diffraction pattern in which the peak positions are substantially in accordance with the peak positions of the pattern shown in FIG. 8.

8. The crystalline neutral Form 2 of claim 1, which is characterized by a differential scanning calorimetry thermogram which has a melting point within the range of about 158-162° C.

9. The crystalline neutral Form 2 of claim 1, which is characterized by a differential scanning calorimetry thermogram substantially in accordance with that shown in FIG. 9.

10. The crystalline neutral solvated Form 2' of claim 1, which is characterized by having one or more additional diffraction peaks at 2θ values selected from 2.20±0.20, 9.41±0.20, 9.66±0.20, 13.25±0.20, 13.72±0.20, 17.42±0.20, 19.75±0.20, 23.60±0.20, 26.56±0.20, 28.06±0.20, 31.54±0.20, 32.75±0.20, and 36.86±0.20.

11. The crystalline neutral solvated Form 2' of claim 1, which is characterized by a powder x-ray diffraction pattern in which the peak positions are substantially in accordance with the peak positions of the pattern shown in FIG. 17 or FIG. 18.

12. The crystalline neutral solvated Form 2' of claim 1, which is characterized by a differential scanning calorimetry thermogram which has a melting point within the range of about 157-161° C.

13. The crystalline neutral solvated Form 2' of claim 1, which is characterized by a differential scanning calorimetry thermogram substantially in accordance with that shown in FIG. 19 or FIG. 20.

14. The crystalline neutral anhydrous Form 3 of claim 1, which is characterized by having one or more additional diffraction peaks at 2θ values selected from 11.06±0.20, 12.94±0.20, 13.94±0.20, 22.12±0.20, 23.58±0.20, 27.32±0.20, 32.40±0.20, 33.46±0.20, and 37.24±0.20.

15. The crystalline neutral anhydrous Form 3 of claim 1, which is characterized by a powder x-ray diffraction pattern in which the peak positions are substantially in accordance with the peak positions of the pattern shown in FIG. 25.

16. The crystalline neutral anhydrous Form 3 of claim 1, which is characterized by a differential scanning calorimetry thermogram which has a melting point within the range of about 157-161° C.

17. The crystalline neutral anhydrous Form 3 of claim 1, which is characterized by a differential scanning calorimetry thermogram substantially in accordance with that shown in FIG. 27.

18. The crystalline neutral anhydrous Form 4 of claim 1, which is characterized by having one or more additional diffraction peaks at 2θ values selected from 4.44±0.20, 11.90±0.20, 15.18±0.20, 16.34±0.20, 18.14±0.20, 20.77±0.20, 21.20±0.20, 22.20±0.20, 24.10±0.20, 24.62±0.20, 25.66±0.20, 26.18±0.20, 27.08±0.20, 30.54±0.20, 32.74±0.20, and 34.40±0.20.

19. The crystalline neutral anhydrous Form 4 of claim 1, which is characterized by a powder x-ray diffraction pattern in which the peak positions are substantially in accordance with the peak positions of the pattern shown in FIG. 33.

20. The crystalline neutral anhydrous Form 4 of claim 1, which is characterized by a differential scanning calorimetry thermogram which has a melting point within the range of about 161-164° C.

21. The crystalline neutral anhydrous Form 4 of claim 1, which is characterized by a differential scanning calorimetry thermogram substantially in accordance with that shown in FIG. 35.

22. The crystalline tromethamine salt of claim 1, which is characterized by having one or more additional diffraction peaks at 2θ values selected from 14.32±0.20, 18.86±0.20, 20.66±0.20, 21.76±0.20, 22.64±0.20, 25.20±0.20, 25.70±0.20, 26.54±0.20, 28.42±0.20, 30.70±0.20, 34.12±0.20, and 38.58±0.20.

23. The crystalline tromethamine salt of claim 1, which is characterized by a powder x-ray diffraction pattern in which the peak positions are substantially in accordance with the peak positions of the pattern shown in FIG. 41.

24. The crystalline tromethamine salt of claim 1, which is characterized by a differential scanning calorimetry thermogram which has a melting point of about 114-115° C.

25. The crystalline tromethamine salt of claim 1, which is characterized by a differential scanning calorimetry thermogram substantially in accordance with that shown in FIG. 42.

26. The crystalline L-lysine salt of claim 1, which is characterized by having one or more additional diffraction peaks at 2θ values selected from 12.84±0.20, 17.14±0.20, 17.62±0.20, 19.36±0.20, 22.34±0.20, 22.78±0.20, 23.98±0.20, 25.74±0.20, 25.98±0.20, 27.28±0.20, 27.94±0.20, 29.25±0.20, 30.42±0.20, and 35.64±0.20.

27. The crystalline L-lysine salt of claim 1, which is characterized by a powder x-ray diffraction pattern in which the peak positions are substantially in accordance with the peak positions of the pattern shown in FIG. 46.

28. The crystalline L-lysine salt of claim 1, which is characterized by a differential scanning calorimetry thermogram which has a melting point of about 178-179° C.

29. The crystalline L-lysine salt of claim 1, characterized by a differential scanning calorimetry thermogram substantially in accordance with that shown in FIG. 47.

30. The crystalline meglumine salt of claim 1, which is characterized by having one or more additional diffraction peaks at 2θ values selected from 12.00±0.20, 16.31±0.20, 17.24±0.20, 18.98±0.20, 19.89±0.20, 21.46±0.20, 23.96±0.20, 24.52±0.20, 26.36±0.20, 26.70±0.20, 27.58±0.20, and 34.46±0.20.

31. The crystalline meglumine salt of claim 1, which is characterized by a powder x-ray diffraction pattern in which the peak positions are substantially in accordance with the peak positions of the pattern shown in FIG. 50.

32. The crystalline meglumine salt of claim 1, which is characterized by a differential scanning calorimetry thermogram which has a melting point of about 104-105° C.

33. The crystalline meglumine salt of claim 1, which is characterized by a differential scanning calorimetry thermogram substantially in accordance with that shown in FIG. 51.

34. A process for preparing the crystalline neutral monohydrate Form 1 of claim 1, comprising the steps of:
(a) treating (R)-3-[N-(3'-chlorobiphenyl-4-ylmethyl)-N'-(3-hydroxyisoxazole-5-carbonyl)hydrazino]-2-hydroxypropionic acid isopropyl ester with methanol and water or acetonitrile and water; (b) heating then cooling the resulting slurry; (c) optionally stirring or sonicating to complete dissolution; or
(a') exposing the crystalline neutral Form 2 to about >75% relative humidity; or
(a") reslurrying the crystalline neutral Form 2 in water or an aqueous solution; (b") heating then cooling the resulting slurry; (c") optionally stirring or sonicating to complete dissolution; and
allowing solids to form and isolating the solids to yield the crystalline neutral monohydrate Form 1.

35. A process for preparing the crystalline neutral Form 2 of claim 1, comprising the steps of:
(a) treating (R)-3-[N-(3'-chlorobiphenyl-4-ylmethyl)-N'-(3-hydroxyisoxazole-5-carbonyl)hydrazino]-2-hydroxypropionic acid isopropyl ester with methylene chloride and an aqueous $NH_4Cl$ solution; (b) optionally stirring or sonicating to complete dissolution; or
(a') reacting (R)-3-{N-(3'-chlorobiphenyl-4-ylmethyl)-N'-[3-(4-methoxybenzyloxy)isoxazole-5-carbonyl]hydrazino}-2-hydroxypropionic acid isopropyl ester with anisole and trifluoroacetic acid in a suitable solvent; (b')

optionally stirring or sonicating to complete dissolution; (c') adding an inert diluent and seed crystals of Form 2; and allowing solids to form and isolating the solids to yield the crystalline neutral Form 2.

36. A process for preparing the crystalline neutral solvated Form 2' of claim 1, comprising the steps of:
    (a) treating amorphous (R)-3-[N-(3'-chlorobiphenyl-4-ylmethyl)-N'-(3-hydroxyisoxazole-5-carbonyl)hydrazino]-2-hydroxypropionic acid isopropyl ester with ethyl acetate, alone or in combination with hexanes; (b) heating then cooling the resulting slurry; (c) optionally stirring or sonicating to complete dissolution; and (d) allowing solids to form and isolating the solids to yield the crystalline neutral solvated Form 2'.

37. A process for preparing the crystalline neutral anhydrous Form 3 of claim 1, comprising the steps of: (a) heating the crystalline neutral anhydrous Form 2 to about 105-120° C.; (b) cooling to about room temperature; and (c) isolating the solids to yield the crystalline neutral anhydrous Form 3.

38. A process for preparing the crystalline neutral anhydrous Form 4 of claim 1, comprising the steps of: (a) heating the crystalline neutral monohydrate Form 1 to about 120° C.; (b) cooling to about room temperature; and (c) isolating the solids to yield the crystalline neutral anhydrous Form 4.

39. A process for preparing the crystalline tromethamine salt of claim 1, comprising the steps of: (a) treating (R)-3-[N-(3'-chlorobiphenyl-4-ylmethyl)-N'-(3-hydroxyisoxazole-5-carbonyl)hydrazino]-2-hydroxypropionic acid isopropyl ester with tromethamine in an inert diluent; (b) optionally heating, stirring, and/or sonicating to complete dissolution; and (c) allowing solids to form and isolating the solids to yield the crystalline compound.

40. A process for preparing the crystalline L-lysine salt of claim 1, comprising the steps of: (a) treating (R)-3-[N-(3'-chlorobiphenyl-4-ylmethyl)-N'-(3-hydroxyisoxazole-5-carbonyl)hydrazino]-2-hydroxypropionic acid isopropyl ester with L-lysine in an inert diluent; (b) optionally heating, stirring, and/or sonicating to complete dissolution; and (c) allowing solids to form and isolating the solids to yield the crystalline compound.

41. A process for preparing the crystalline meglumine salt of claim 1, comprising the steps of: (a) treating (R)-3-[N-(3'-chlorobiphenyl-4-ylmethyl)-N'-(3-hydroxyisoxazole-5-carbonyl)hydrazino]-2-hydroxypropionic acid isopropyl ester with meglumine in an inert diluent; (b) optionally heating, stirring, and/or sonicating to complete dissolution; and (c) allowing solids to form and isolating the solids to yield the crystalline compound.

42. A process for purifying (R)-3-[N-(3'-chlorobiphenyl-4-ylmethyl)-N'-(3-hydroxyisoxazole-5-carbonyl)hydrazino]-2-hydroxypropionic acid isopropyl ester comprising forming the crystalline compound of claim 1.

43. A pharmaceutical composition comprising a pharmaceutically acceptable carrier and the crystalline compound of claim 1.

44. The pharmaceutical composition of claim 43, further comprising a therapeutic agent selected from adenosine receptor antagonists, α-adrenergic receptor antagonists, $β_1$-adrenergic receptor antagonists, $β_2$-adrenergic receptor agonists, dual-acting β-adrenergic receptor antagonist/$α_1$-receptor antagonists, advanced glycation end product breakers, aldosterone antagonists, aldosterone synthase inhibitors, aminopeptidase N inhibitors, androgens, angiotensin-converting enzyme inhibitors and dual-acting angiotensin-converting enzyme/neprilysin inhibitors, angiotensin-converting enzyme 2 activators and stimulators, angiotensin-II vaccines, anticoagulants, anti-diabetic agents, antidiarrheal agents, anti-glaucoma agents, anti-lipid agents, antinociceptive agents, anti-thrombotic agents, $AT_1$ receptor antagonists and dual-acting $AT_1$ receptor antagonist/neprilysin inhibitors and multifunctional angiotensin receptor blockers, bradykinin receptor antagonists, calcium channel blockers, chymase inhibitors, digoxin, diuretics, dopamine agonists, endothelin converting enzyme inhibitors, endothelin receptor antagonists, HMG-CoA reductase inhibitors, estrogens, estrogen receptor agonists and/or antagonists, monoamine reuptake inhibitors, muscle relaxants, natriuretic peptides and their analogs, natriuretic peptide clearance receptor antagonists, neprilysin inhibitors, nitric oxide donors, non-steroidal anti-inflammatory agents, N-methyl d-aspartate receptor antagonists, opioid receptor agonists, phosphodiesterase inhibitors, prostaglandin analogs, prostaglandin receptor agonists, renin inhibitors, selective serotonin reuptake inhibitors, sodium channel blocker, soluble guanylate cyclase stimulators and activators, tricyclic antidepressants, vasopressin receptor antagonists, and combinations thereof.

45. The pharmaceutical composition of claim 44, wherein the therapeutic agent is an $AT_1$ receptor antagonist.

46. A method for treating hypertension, heart failure, or renal disease, comprising administering to a patient in need thereof a therapeutically effective amount of the crystalline compound of claim 1.

* * * * *